US010610236B2

(12) United States Patent
Baril

(10) Patent No.: US 10,610,236 B2
(45) Date of Patent: Apr. 7, 2020

(54) ENDOSCOPIC REPOSABLE SURGICAL CLIP APPLIER

(71) Applicant: Covidien LP, Mansfield, MA (US)

(72) Inventor: Jacob Baril, White Plains, NY (US)

(73) Assignee: COVIDIEN LP, Mansfield, MA (US)

(*) Notice: Subject to any disclaimer, the term of this patent is extended or adjusted under 35 U.S.C. 154(b) by 379 days.

(21) Appl. No.: 15/705,300

(22) Filed: Sep. 15, 2017

(65) Prior Publication Data

US 2018/0116674 A1    May 3, 2018

Related U.S. Application Data

(60) Provisional application No. 62/415,573, filed on Nov. 1, 2016.

(51) Int. Cl.
*A61B 17/128* (2006.01)
*A61B 17/00* (2006.01)
(Continued)

(52) U.S. Cl.
CPC .... *A61B 17/1285* (2013.01); *A61B 17/00234* (2013.01); *A61B 17/105* (2013.01);
(Continued)

(58) Field of Classification Search
CPC ............ A61B 17/1285; A61B 17/2909; A61B 17/3201; A61B 17/44; A61B 17/22031;
(Continued)

(56) References Cited

U.S. PATENT DOCUMENTS 3,120,230 A    2/1964   Skold
3,363,628 A    1/1968   Wood
(Continued)

FOREIGN PATENT DOCUMENTS

AU    2013254887 A1    11/2013
CA       1163889 A      3/1984
(Continued)

OTHER PUBLICATIONS

European Search Report corresponding to Patent Application EP 18154617.7 dated Jun. 25, 2018.
(Continued)

*Primary Examiner* — Tan-Uyen T Ho
*Assistant Examiner* — Chima U Igboko

(57) ABSTRACT

A hub assembly for use with an endoscopic assembly of a reposable surgical clip applier includes an outer housing and a drive assembly supported within the outer housing. The drive assembly includes a cartridge cylinder slidably supported within the outer housing, a plunger translatably supported within the outer housing and slidably coupled to the cartridge cylinder, a first biasing element interposed between the cartridge cylinder and the outer housing, and a second biasing element interposed between the cartridge cylinder and the plunger. The first biasing element includes a first threshold and the second biasing element includes a second threshold that is greater than the first threshold. A force exceeding the first threshold causes the cartridge cylinder and plunger to translate simultaneously and a force exceeding the second threshold causes the cartridge cylinder to translate relative to the plunger.

20 Claims, 28 Drawing Sheets

(51) Int. Cl.
*A61B 17/10* (2006.01)
*A61B 17/29* (2006.01)

(52) U.S. Cl.
CPC .............. *A61B 2017/0046* (2013.01); *A61B 2017/00407* (2013.01); *A61B 2017/00477* (2013.01); *A61B 2017/2923* (2013.01); *A61B 2017/2929* (2013.01); *A61B 2017/2946* (2013.01)

(58) Field of Classification Search
CPC ........ A61B 17/22034; A61B 17/22035; A61B 17/28; A61B 17/2841; A61B 2017/0046; A61B 2017/00477; A61B 2017/2901; A61B 2017/2902; A61B 2017/2903; A61B 2017/2904; A61B 2017/2905; A61B 2017/2912; A61B 2017/2913; A61B 2017/2915; A61B 2017/2916; A61B 2017/2917; A61B 2017/2923; A61B 2017/00367; A61B 2017/00371; A61B 2017/00376; A61B 2017/0038; A61B 2017/00384; A61B 2017/2845; A61B 2017/07271; A61B 10/02; A61B 10/0291; A61B 10/06; A61B 2010/0208
See application file for complete search history.

(56) References Cited

U.S. PATENT DOCUMENTS

| | | | |
|---|---|---|---|
| 3,638,847 A | 2/1972 | Noiles et al. | |
| 3,675,688 A * | 7/1972 | Bryan | A61B 17/128 140/93 D |
| 3,735,762 A | 5/1973 | Bryan et al. | |
| 3,867,944 A | 2/1975 | Samuels | |
| 4,242,902 A | 1/1981 | Green | |
| 4,296,751 A | 10/1981 | Blake, III et al. | |
| 4,372,316 A | 2/1983 | Blake, III et al. | |
| 4,408,603 A | 10/1983 | Blake, III et al. | |
| 4,412,539 A | 11/1983 | Jarvik | |
| 4,418,694 A | 12/1983 | Beroff et al. | |
| 4,471,780 A | 9/1984 | Menges et al. | |
| 4,480,640 A | 11/1984 | Becht | |
| 4,480,641 A | 11/1984 | Failla et al. | |
| 4,487,204 A | 12/1984 | Hrouda | |
| 4,487,205 A | 12/1984 | Di Giovanni et al. | |
| 4,491,133 A | 1/1985 | Menges et al. | |
| 4,492,232 A | 1/1985 | Green | |
| 4,498,476 A | 2/1985 | Cerwin et al. | |
| 4,500,024 A | 2/1985 | DiGiovanni et al. | |
| 4,509,518 A | 4/1985 | McGarry et al. | |
| 4,512,345 A | 4/1985 | Green | |
| 4,522,207 A | 6/1985 | Klieman et al. | |
| 4,532,925 A | 8/1985 | Blake, III | |
| 4,534,351 A | 8/1985 | Rothfuss et al. | |
| 4,545,377 A | 10/1985 | Cerwin et al. | |
| 4,549,544 A | 10/1985 | Favaron | |
| 4,556,058 A | 12/1985 | Green | |
| 4,557,263 A | 12/1985 | Green | |
| 4,562,839 A | 1/1986 | Blake, III et al. | |
| 4,572,183 A | 2/1986 | Juska | |
| 4,576,165 A | 3/1986 | Green et al. | |
| 4,576,166 A | 3/1986 | Montgomery et al. | |
| 4,590,937 A | 5/1986 | Deniega | |
| 4,598,711 A | 7/1986 | Deniega | |
| 4,602,631 A | 7/1986 | Funatsu | |
| 4,611,595 A | 9/1986 | Klieman et al. | |
| 4,612,932 A | 9/1986 | Caspar et al. | |
| 4,616,650 A | 10/1986 | Green et al. | |
| 4,616,651 A | 10/1986 | Golden | |
| 4,624,254 A | 11/1986 | McGarry et al. | |
| 4,637,395 A | 1/1987 | Caspar et al. | |
| 4,646,740 A | 3/1987 | Peters et al. | |
| 4,647,504 A | 3/1987 | Kimimura et al. | |
| 4,658,822 A | 4/1987 | Kees, Jr. | |
| 4,660,558 A | 4/1987 | Kees, Jr. | |
| 4,662,373 A | 5/1987 | Montgomery et al. | |
| 4,662,374 A | 5/1987 | Blake, III | |
| 4,671,278 A | 6/1987 | Chin | |
| 4,671,282 A | 6/1987 | Tretbar | |
| 4,674,504 A | 6/1987 | Klieman et al. | |
| 4,681,107 A | 7/1987 | Kees, Jr. | |
| 4,696,396 A | 9/1987 | Samuels | |
| 4,702,247 A | 10/1987 | Blake, III et al. | |
| 4,706,668 A | 11/1987 | Backer | |
| 4,712,549 A | 12/1987 | Peters et al. | |
| 4,733,666 A | 3/1988 | Mercer, Jr. | |
| 4,759,364 A | 7/1988 | Boebel | |
| 4,765,335 A | 8/1988 | Schmidt et al. | |
| 4,777,949 A | 10/1988 | Perlin | |
| 4,796,625 A | 1/1989 | Kees, Jr. | |
| 4,799,481 A | 1/1989 | Transue et al. | |
| 4,815,466 A | 3/1989 | Perlin | |
| 4,821,721 A | 4/1989 | Chin et al. | |
| 4,822,348 A | 4/1989 | Casey | |
| 4,834,096 A | 5/1989 | Oh et al. | |
| 4,850,355 A | 7/1989 | Brooks et al. | |
| 4,854,317 A | 8/1989 | Braun | |
| 4,856,517 A | 8/1989 | Collins et al. | |
| 4,929,239 A | 5/1990 | Braun | |
| 4,931,058 A | 6/1990 | Cooper | |
| 4,934,364 A | 6/1990 | Green | |
| 4,957,500 A | 9/1990 | Liang et al. | |
| 4,966,603 A | 10/1990 | Focelle et al. | |
| 4,967,949 A | 11/1990 | Sandhaus | |
| 4,983,176 A | 1/1991 | Cushman et al. | |
| 4,988,355 A | 1/1991 | Leveen et al. | |
| 5,002,552 A | 3/1991 | Casey | |
| 5,026,379 A | 6/1991 | Yoon | |
| 5,030,224 A | 7/1991 | Wright et al. | |
| 5,030,226 A | 7/1991 | Green et al. | |
| 5,032,127 A | 7/1991 | Frazee et al. | |
| 5,035,692 A | 7/1991 | Lyon et al. | |
| 5,047,038 A | 9/1991 | Peters et al. | |
| 5,049,152 A | 9/1991 | Simon et al. | |
| 5,049,153 A | 9/1991 | Nakao et al. | |
| 5,053,045 A | 10/1991 | Schmidt et al. | |
| 5,059,202 A | 10/1991 | Liang et al. | |
| 5,062,563 A | 11/1991 | Green et al. | |
| 5,062,846 A | 11/1991 | Oh et al. | |
| 5,078,731 A | 1/1992 | Hayhurst | |
| 5,084,057 A | 1/1992 | Green et al. | |
| 5,100,416 A | 3/1992 | Oh et al. | |
| 5,100,420 A | 3/1992 | Green et al. | |
| 5,104,394 A | 4/1992 | Knoepfler | |
| 5,104,395 A | 4/1992 | Thornton et al. | |
| 5,112,343 A | 5/1992 | Thornton | |
| 5,122,150 A | 6/1992 | Puig | |
| 5,127,915 A | 7/1992 | Mattson | |
| 5,129,885 A | 7/1992 | Green et al. | |
| 5,156,608 A | 10/1992 | Troidl et al. | |
| 5,160,339 A | 11/1992 | Chen et al. | |
| 5,163,945 A | 11/1992 | Ortiz et al. | |
| 5,171,247 A | 12/1992 | Hughett et al. | |
| 5,171,249 A | 12/1992 | Stefanchik et al. | |
| 5,171,250 A | 12/1992 | Yoon | |
| 5,171,251 A | 12/1992 | Bregen et al. | |
| 5,171,252 A | 12/1992 | Friedland | |
| 5,171,253 A | 12/1992 | Klieman | |
| 5,192,288 A | 3/1993 | Thompson et al. | |
| 5,197,970 A | 3/1993 | Green et al. | |
| 5,199,566 A | 4/1993 | Ortiz et al. | |
| 5,201,746 A | 4/1993 | Shichman | |
| 5,201,900 A | 4/1993 | Nardella | |
| 5,207,691 A | 5/1993 | Nardella | |
| 5,207,692 A | 5/1993 | Kraus et al. | |
| 5,217,473 A | 6/1993 | Yoon | |
| 5,219,353 A | 6/1993 | Garvey, III et al. | |
| 5,246,450 A | 9/1993 | Thornton et al. | |
| 5,269,792 A | 12/1993 | Kovac et al. | |
| 5,281,228 A | 1/1994 | Wolfson | |
| 5,282,807 A | 2/1994 | Knoepfler | |
| 5,282,808 A | 2/1994 | Kovac et al. | |

(56) References Cited

U.S. PATENT DOCUMENTS

| | | |
|---|---|---|
| 5,282,832 A | 2/1994 | Toso et al. |
| 5,289,963 A | 3/1994 | McGarry et al. |
| 5,290,299 A | 3/1994 | Fain et al. |
| 5,300,081 A | 4/1994 | Young et al. |
| 5,304,183 A | 4/1994 | Gourlay et al. |
| 5,306,280 A | 4/1994 | Bregen et al. |
| 5,306,283 A | 4/1994 | Conners |
| 5,312,426 A | 5/1994 | Segawa et al. |
| 5,330,442 A | 7/1994 | Green et al. |
| 5,330,487 A | 7/1994 | Thornton et al. |
| 5,340,360 A | 8/1994 | Stefanchik |
| 5,342,373 A | 8/1994 | Stefanchik et al. |
| 5,354,304 A | 10/1994 | Allen et al. |
| 5,354,306 A | 10/1994 | Garvey, III et al. |
| 5,356,064 A | 10/1994 | Green et al. |
| 5,366,458 A | 11/1994 | Korthoff et al. |
| 5,366,459 A | 11/1994 | Yoon |
| 5,368,600 A | 11/1994 | Failla et al. |
| 5,381,943 A | 1/1995 | Allen et al. |
| 5,382,253 A | 1/1995 | Hogendijk |
| 5,382,254 A | 1/1995 | McGarry et al. |
| 5,382,255 A | 1/1995 | Castro et al. |
| 5,383,880 A | 1/1995 | Hooven |
| 5,383,881 A | 1/1995 | Green et al. |
| 5,395,375 A | 3/1995 | Turkel et al. |
| 5,395,381 A | 3/1995 | Green et al. |
| 5,403,327 A | 4/1995 | Thornton et al. |
| 5,409,498 A | 4/1995 | Braddock et al. |
| 5,413,584 A | 5/1995 | Schulze |
| 5,423,835 A | 6/1995 | Green et al. |
| 5,425,740 A | 6/1995 | Hutchinson, Jr. |
| 5,431,667 A | 7/1995 | Thompson et al. |
| 5,431,668 A | 7/1995 | Burbank, III et al. |
| 5,431,669 A | 7/1995 | Thompson et al. |
| 5,439,468 A | 8/1995 | Schulze et al. |
| 5,441,509 A | 8/1995 | Vidal et al. |
| 5,447,513 A | 9/1995 | Davison et al. |
| 5,449,365 A | 9/1995 | Green et al. |
| 5,462,555 A | 10/1995 | Bolanos et al. |
| 5,462,558 A | 10/1995 | Kolesa et al. |
| 5,464,416 A | 11/1995 | Steckel |
| 5,474,566 A | 12/1995 | Alesi et al. |
| 5,474,567 A | 12/1995 | Stefanchik et al. |
| 5,474,572 A | 12/1995 | Hayhurst |
| 5,487,499 A | 1/1996 | Sorrentino et al. |
| 5,487,746 A | 1/1996 | Yu et al. |
| 5,501,693 A | 3/1996 | Gravener |
| 5,509,920 A | 4/1996 | Phillips et al. |
| 5,514,149 A | 5/1996 | Green et al. |
| 5,520,701 A | 5/1996 | Lerch |
| 5,527,318 A | 6/1996 | McGarry |
| 5,527,319 A | 6/1996 | Green et al. |
| 5,527,320 A | 6/1996 | Carruthers et al. |
| 5,542,949 A | 8/1996 | Yoon |
| 5,547,474 A | 8/1996 | Kloeckl et al. |
| 5,569,274 A | 10/1996 | Rapacki et al. |
| 5,571,121 A | 11/1996 | Heifetz |
| 5,575,802 A | 11/1996 | McQuilkin et al. |
| 5,582,615 A | 12/1996 | Foshee et al. |
| 5,584,840 A | 12/1996 | Ramsey et al. |
| 5,591,178 A | 1/1997 | Green et al. |
| 5,593,414 A | 1/1997 | Shipp et al. |
| 5,593,421 A | 1/1997 | Bauer |
| 5,601,573 A * | 2/1997 | Fogelberg .......... A61B 17/1227 227/901 |
| 5,601,574 A | 2/1997 | Stefanchik et al. |
| 5,607,436 A | 3/1997 | Pratt et al. |
| 5,618,291 A | 4/1997 | Thompson et al. |
| 5,618,306 A | 4/1997 | Roth et al. |
| 5,620,452 A | 4/1997 | Yoon |
| 5,626,585 A | 5/1997 | Mittelstadt et al. |
| 5,626,586 A | 5/1997 | Pistl et al. |
| 5,626,587 A | 5/1997 | Bishop et al. |
| 5,626,592 A | 5/1997 | Phillips et al. |
| RE35,525 E | 6/1997 | Stefanchik et al. |
| 5,634,930 A | 6/1997 | Thornton et al. |
| 5,643,291 A | 7/1997 | Pier et al. |
| 5,645,551 A | 7/1997 | Green et al. |
| 5,645,553 A | 7/1997 | Kolesa et al. |
| 5,649,937 A | 7/1997 | Bito et al. |
| 5,653,720 A | 8/1997 | Johnson et al. |
| 5,662,662 A | 9/1997 | Bishop et al. |
| 5,662,676 A | 9/1997 | Koninckx |
| 5,662,679 A | 9/1997 | Voss et al. |
| 5,665,097 A | 9/1997 | Baker et al. |
| 5,676,676 A | 10/1997 | Porter |
| 5,681,330 A | 10/1997 | Hughett et al. |
| 5,683,405 A | 11/1997 | Yacoubian et al. |
| 5,695,502 A | 12/1997 | Pier et al. |
| 5,695,505 A | 12/1997 | Yoon |
| 5,697,938 A | 12/1997 | Jensen et al. |
| 5,697,942 A | 12/1997 | Palti |
| 5,700,270 A | 12/1997 | Peyser et al. |
| 5,700,271 A | 12/1997 | Whitfield et al. |
| 5,702,048 A | 12/1997 | Eberlin |
| 5,709,706 A | 1/1998 | Kienzle et al. |
| 5,713,911 A | 2/1998 | Racenet et al. |
| 5,713,912 A | 2/1998 | Porter |
| 5,720,756 A | 2/1998 | Green et al. |
| 5,722,982 A | 3/1998 | Ferreira et al. |
| 5,725,537 A | 3/1998 | Green et al. |
| 5,725,538 A | 3/1998 | Green et al. |
| 5,725,542 A | 3/1998 | Yoon |
| 5,733,295 A | 3/1998 | Back et al. |
| 5,749,881 A | 5/1998 | Sackier et al. |
| 5,755,726 A | 5/1998 | Pratt et al. |
| 5,766,189 A | 6/1998 | Matsuno |
| 5,769,857 A | 6/1998 | Reztzov et al. |
| 5,772,673 A | 6/1998 | Cuny et al. |
| 5,776,146 A | 7/1998 | Sackier et al. |
| 5,776,147 A | 7/1998 | Dolendo |
| 5,779,718 A | 7/1998 | Green et al. |
| 5,779,720 A | 7/1998 | Walder-Utz et al. |
| 5,782,844 A | 7/1998 | Yoon et al. |
| 5,788,698 A | 8/1998 | Savornin |
| 5,792,149 A | 8/1998 | Sherts et al. |
| 5,792,150 A | 8/1998 | Pratt et al. |
| 5,797,922 A | 8/1998 | Hessel et al. |
| 5,810,853 A | 9/1998 | Yoon |
| 5,817,116 A | 10/1998 | Takahashi et al. |
| 5,827,306 A | 10/1998 | Yoon |
| 5,827,323 A | 10/1998 | Klieman et al. |
| 5,833,695 A | 11/1998 | Yoon |
| 5,833,696 A | 11/1998 | Whitfield et al. |
| 5,833,700 A | 11/1998 | Fogelberg et al. |
| 5,835,199 A | 11/1998 | Phillips et al. |
| 5,843,097 A | 12/1998 | Mayenberger et al. |
| 5,843,101 A | 12/1998 | Fry |
| 5,846,255 A | 12/1998 | Casey |
| 5,849,019 A | 12/1998 | Yoon |
| 5,858,018 A | 1/1999 | Shipp et al. |
| 5,861,005 A | 1/1999 | Kontos |
| 5,868,759 A | 2/1999 | Peyser et al. |
| 5,868,761 A | 2/1999 | Nicholas et al. |
| 5,876,410 A | 3/1999 | Petillo |
| 5,895,394 A | 4/1999 | Kienzle et al. |
| 5,897,565 A | 4/1999 | Foster |
| 5,904,693 A | 5/1999 | Dicesare et al. |
| 5,906,625 A | 5/1999 | Bito et al. |
| 5,913,862 A | 6/1999 | Ramsey et al. |
| 5,913,876 A | 6/1999 | Taylor et al. |
| 5,918,791 A | 7/1999 | Sorrentino et al. |
| 5,921,996 A | 7/1999 | Sherman |
| 5,921,997 A | 7/1999 | Fogelberg et al. |
| 5,928,251 A | 7/1999 | Aranyi et al. |
| 5,938,667 A | 8/1999 | Peyser et al. |
| 5,951,574 A | 9/1999 | Stefanchik et al. |
| 5,972,003 A | 10/1999 | Rousseau et al. |
| 5,976,159 A | 11/1999 | Bolduc et al. |
| 5,993,465 A | 11/1999 | Shipp et al. |
| 6,004,335 A | 12/1999 | Vaitekunas et al. |
| 6,009,551 A | 12/1999 | Sheynblat |
| 6,017,358 A | 1/2000 | Yoon et al. |
| 6,045,560 A | 4/2000 | McKean et al. |

(56) References Cited

U.S. PATENT DOCUMENTS

| | | |
|---|---|---|
| 6,053,908 A | 4/2000 | Crainich et al. |
| RE36,720 E | 5/2000 | Green et al. |
| 6,059,799 A | 5/2000 | Aranyi et al. |
| 6,099,536 A | 8/2000 | Petillo |
| 6,099,537 A * | 8/2000 | Sugai ............... A61B 17/0684 |
| | | 606/143 |
| 6,139,555 A | 10/2000 | Hart et al. |
| 6,210,418 B1 | 4/2001 | Storz et al. |
| 6,217,590 B1 | 4/2001 | Levinson |
| 6,228,097 B1 | 5/2001 | Levinson et al. |
| 6,241,740 B1 | 6/2001 | Davis et al. |
| 6,258,105 B1 | 7/2001 | Hart et al. |
| 6,261,302 B1 | 7/2001 | Voegele et al. |
| 6,273,898 B1 | 8/2001 | Kienzle et al. |
| 6,277,131 B1 | 8/2001 | Kalikow |
| 6,306,149 B1 | 10/2001 | Meade |
| 6,318,619 B1 | 11/2001 | Lee |
| 6,322,571 B1 | 11/2001 | Adams |
| 6,350,269 B1 | 2/2002 | Shipp et al. |
| 6,352,541 B1 | 3/2002 | Kienzle et al. |
| 6,391,035 B1 | 5/2002 | Appleby et al. |
| 6,423,079 B1 | 7/2002 | Blake, III |
| 6,428,548 B1 | 8/2002 | Durgin et al. |
| 6,440,144 B1 | 8/2002 | Bacher |
| 6,461,363 B1 | 10/2002 | Gadberry et al. |
| 6,464,710 B1 | 10/2002 | Foster |
| 6,494,886 B1 | 12/2002 | Wilk et al. |
| 6,517,536 B2 | 2/2003 | Hooven et al. |
| 6,520,972 B2 | 2/2003 | Peters |
| 6,527,786 B1 | 3/2003 | Davis et al. |
| 6,537,289 B1 | 3/2003 | Kayan et al. |
| 6,546,935 B2 | 4/2003 | Hooven |
| 6,551,333 B2 | 4/2003 | Kuhns et al. |
| 6,562,051 B1 | 5/2003 | Bolduc et al. |
| 6,569,171 B2 | 5/2003 | DeGuillebon et al. |
| 6,579,304 B1 | 6/2003 | Hart et al. |
| 6,599,298 B1 | 7/2003 | Forster et al. |
| 6,602,252 B2 | 8/2003 | Mollenauer |
| 6,607,540 B1 | 8/2003 | Shipp |
| 6,613,060 B2 | 9/2003 | Adams et al. |
| 6,626,916 B1 | 9/2003 | Yeung et al. |
| 6,626,922 B1 | 9/2003 | Hart et al. |
| 6,648,898 B1 | 11/2003 | Baxter |
| 6,652,538 B2 | 11/2003 | Kayan et al. |
| 6,652,539 B2 | 11/2003 | Shipp et al. |
| 6,656,193 B2 | 12/2003 | Grant et al. |
| 6,673,083 B1 | 1/2004 | Kayan et al. |
| 6,676,659 B2 | 1/2004 | Hutchins et al. |
| 6,679,894 B2 | 1/2004 | Damarati |
| RE38,445 E | 2/2004 | Pistl et al. |
| 6,695,854 B1 | 2/2004 | Kayan et al. |
| 6,706,057 B1 | 3/2004 | Bidoia et al. |
| 6,716,226 B2 | 4/2004 | Sixto, Jr. et al. |
| 6,723,109 B2 | 4/2004 | Solingen |
| 6,743,240 B2 | 6/2004 | Smith et al. |
| 6,743,241 B2 | 6/2004 | Kerr |
| 6,773,438 B1 | 8/2004 | Knodel et al. |
| 6,773,440 B2 | 8/2004 | Gannoe et al. |
| 6,776,783 B1 | 8/2004 | Frantzen et al. |
| 6,776,784 B2 | 8/2004 | Ginn |
| 6,780,195 B2 | 8/2004 | Porat |
| 6,793,663 B2 | 9/2004 | Kneifel et al. |
| 6,793,664 B2 | 9/2004 | Mazzocchi et al. |
| 6,802,848 B2 | 10/2004 | Anderson et al. |
| 6,814,742 B2 | 11/2004 | Kimura et al. |
| 6,818,009 B2 | 11/2004 | Hart et al. |
| 6,821,273 B2 | 11/2004 | Mollenauer |
| 6,821,284 B2 | 11/2004 | Sturtz et al. |
| 6,821,285 B2 | 11/2004 | Laufer et al. |
| 6,824,547 B2 | 11/2004 | Wilson, Jr. et al. |
| 6,824,548 B2 | 11/2004 | Smith et al. |
| 6,835,199 B2 | 12/2004 | McGuckin, Jr. et al. |
| 6,835,200 B2 | 12/2004 | Laufer et al. |
| 6,837,893 B2 | 1/2005 | Miller |
| 6,837,894 B2 | 1/2005 | Pugsley, Jr. et al. |
| 6,837,895 B2 | 1/2005 | Mayenberger |
| 6,840,945 B2 | 1/2005 | Manetakis et al. |
| 6,843,794 B2 | 1/2005 | Sixto, Jr. et al. |
| 6,849,078 B2 | 2/2005 | Durgin et al. |
| 6,849,079 B1 | 2/2005 | Blake, III et al. |
| 6,853,879 B2 | 2/2005 | Sunaoshi |
| 6,869,435 B2 | 3/2005 | Blake, III |
| 6,869,436 B2 | 3/2005 | Wendlandt |
| 6,889,116 B2 | 5/2005 | Jinno |
| 6,896,676 B2 | 5/2005 | Zubok et al. |
| 6,896,682 B1 | 5/2005 | McClellan et al. |
| 6,896,684 B2 | 5/2005 | Monassevitch et al. |
| 6,905,503 B2 | 6/2005 | Gifford, III et al. |
| 6,911,032 B2 | 6/2005 | Jugenheimer et al. |
| 6,911,033 B2 | 6/2005 | de Guillebon et al. |
| 6,913,607 B2 | 7/2005 | Ainsworth et al. |
| 6,916,327 B2 | 7/2005 | Northrup, III et al. |
| 6,916,332 B2 | 7/2005 | Adams |
| 6,923,818 B2 | 8/2005 | Muramatsu et al. |
| 6,939,356 B2 | 9/2005 | Debbas |
| 6,942,674 B2 | 9/2005 | Belef et al. |
| 6,942,676 B2 | 9/2005 | Buelna |
| 6,945,978 B1 | 9/2005 | Hyde |
| 6,945,979 B2 | 9/2005 | Kortenbach et al. |
| 6,949,107 B2 | 9/2005 | McGuckin, Jr. et al. |
| 6,953,465 B2 | 10/2005 | Dieck et al. |
| 6,955,643 B2 | 10/2005 | Gellman et al. |
| 6,959,852 B2 | 11/2005 | Shelton, IV et al. |
| 6,960,218 B2 | 11/2005 | Rennich |
| 6,960,221 B2 | 11/2005 | Ho et al. |
| 6,962,594 B1 | 11/2005 | Thevenet |
| 6,963,792 B1 | 11/2005 | Green |
| 6,964,363 B2 | 11/2005 | Wales et al. |
| 6,964,668 B2 | 11/2005 | Modesitt et al. |
| 6,966,875 B1 | 11/2005 | Longobardi |
| 6,966,917 B1 | 11/2005 | Suyker et al. |
| 6,966,919 B2 | 11/2005 | Sixto, Jr. et al. |
| 6,969,391 B1 | 11/2005 | Gazzani |
| 6,972,023 B2 | 12/2005 | Whayne et al. |
| 6,972,027 B2 | 12/2005 | Fallin et al. |
| 6,973,770 B2 | 12/2005 | Schnipke et al. |
| 6,974,462 B2 | 12/2005 | Sater |
| 6,974,466 B2 | 12/2005 | Ahmed et al. |
| 6,974,475 B1 | 12/2005 | Wall |
| 6,981,505 B2 | 1/2006 | Krause et al. |
| 6,981,628 B2 | 1/2006 | Wales |
| 6,991,635 B2 | 1/2006 | Takamoto et al. |
| 7,001,399 B2 | 2/2006 | Damarati |
| 7,037,315 B2 | 5/2006 | Sancoff et al. |
| 7,041,119 B2 | 5/2006 | Green |
| 7,052,504 B2 | 5/2006 | Hughett |
| 7,056,330 B2 | 6/2006 | Gayton |
| 7,070,602 B2 | 7/2006 | Smith et al. |
| 7,108,700 B2 | 9/2006 | Chan |
| 7,108,703 B2 | 9/2006 | Danitz et al. |
| 7,141,056 B2 | 11/2006 | Manetakis |
| 7,144,402 B2 | 12/2006 | Kuester, III |
| 7,175,648 B2 | 2/2007 | Nakao |
| 7,179,265 B2 | 2/2007 | Manetakis et al. |
| 7,207,997 B2 | 4/2007 | Shipp et al. |
| 7,211,091 B2 | 5/2007 | Fowler et al. |
| 7,211,092 B2 | 5/2007 | Hughett |
| 7,213,736 B2 | 5/2007 | Wales et al. |
| 7,214,230 B2 | 5/2007 | Brock et al. |
| 7,214,232 B2 | 5/2007 | Bowman et al. |
| 7,223,271 B2 | 5/2007 | Muramatsu et al. |
| 7,223,272 B2 | 5/2007 | Francese et al. |
| 7,232,445 B2 | 6/2007 | Kortenbach et al. |
| 7,238,191 B2 | 7/2007 | Bachmann |
| 7,261,724 B2 | 8/2007 | Molitor et al. |
| 7,261,725 B2 | 8/2007 | Binmoeller |
| 7,264,625 B1 | 9/2007 | Buncke |
| 7,288,098 B2 | 10/2007 | Huitema et al. |
| 7,297,149 B2 | 11/2007 | Vitali et al. |
| 7,312,188 B2 | 12/2007 | Kiso |
| 7,316,693 B2 | 1/2008 | Viola |
| 7,316,696 B2 | 1/2008 | Wilson, Jr. et al. |
| 7,322,995 B2 | 1/2008 | Buckman et al. |
| 7,326,223 B2 | 2/2008 | Wilson, Jr. |

(56) References Cited

U.S. PATENT DOCUMENTS

| | | |
|---|---|---|
| 7,329,266 B2 | 2/2008 | Royse et al. |
| 7,331,968 B2 | 2/2008 | Arp et al. |
| 7,338,503 B2 | 3/2008 | Rosenberg et al. |
| 7,357,805 B2 | 4/2008 | Masuda et al. |
| 7,367,939 B2 | 5/2008 | Smith et al. |
| 7,407,074 B2 | 8/2008 | Ortiz et al. |
| 7,419,495 B2 | 9/2008 | Menn et al. |
| 7,422,137 B2 | 9/2008 | Manzo |
| 7,431,724 B2 | 10/2008 | Manetakis et al. |
| 7,452,327 B2 | 11/2008 | Durgin et al. |
| 7,485,124 B2 | 2/2009 | Kuhns et al. |
| 7,488,335 B2 | 2/2009 | Sgro |
| 7,510,562 B2 | 3/2009 | Lindsay |
| 7,552,853 B2 | 6/2009 | Mas et al. |
| 7,559,937 B2 | 7/2009 | de la Torre et al. |
| 7,572,266 B2 | 8/2009 | Young et al. |
| 7,578,827 B2 | 8/2009 | Gadberry et al. |
| 7,582,095 B2 | 9/2009 | Shipp et al. |
| 7,585,304 B2 | 9/2009 | Hughett |
| 7,615,058 B2 | 11/2009 | Sixto, Jr. et al. |
| 7,621,926 B2 | 11/2009 | Wixey et al. |
| 7,637,917 B2 | 12/2009 | Whitfield et al. |
| 7,644,848 B2 | 1/2010 | Swayze et al. |
| 7,686,820 B2 | 3/2010 | Huitema et al. |
| 7,695,482 B2 | 4/2010 | Viola |
| 7,717,926 B2 | 5/2010 | Whitfield et al. |
| 7,727,247 B2 | 6/2010 | Kimura et al. |
| 7,727,248 B2 | 6/2010 | Smith et al. |
| 7,731,724 B2 | 6/2010 | Huitema et al. |
| 7,731,725 B2 | 6/2010 | Gadberry et al. |
| 7,736,388 B2 | 6/2010 | Goldfarb et al. |
| 7,740,639 B2 | 6/2010 | Hummel et al. |
| 7,740,641 B2 | 6/2010 | Huitema |
| 7,744,623 B2 | 6/2010 | Anderson |
| 7,752,853 B2 | 7/2010 | Singh et al. |
| 7,753,250 B2 | 7/2010 | Clauson et al. |
| 7,766,207 B2 | 8/2010 | Mather et al. |
| 7,770,773 B2 | 8/2010 | Whitman et al. |
| 7,776,058 B2 | 8/2010 | Rosenberg et al. |
| 7,780,688 B2 | 8/2010 | Sakakine et al. |
| 7,793,813 B2 | 9/2010 | Bettuchi |
| 7,806,903 B2 | 10/2010 | Shibata et al. |
| 7,819,886 B2 | 10/2010 | Whitfield et al. |
| 7,823,592 B2 | 11/2010 | Bettuchi et al. |
| 7,857,828 B2 | 12/2010 | Jabba et al. |
| 7,871,416 B2 | 1/2011 | Phillips |
| 7,887,553 B2 | 2/2011 | Lehman et al. |
| 7,892,244 B2 | 2/2011 | Monassevitch et al. |
| 7,896,895 B2 | 3/2011 | Boudreaux et al. |
| 7,901,420 B2 | 3/2011 | Dunn |
| 7,905,890 B2 | 3/2011 | Whitfield et al. |
| 7,914,544 B2 | 3/2011 | Nguyen et al. |
| 7,914,551 B2 | 3/2011 | Ortiz et al. |
| 7,942,885 B2 | 5/2011 | Sixto, Jr. et al. |
| 7,942,890 B2 | 5/2011 | D'Agostino et al. |
| 7,954,682 B2 | 6/2011 | Giordano et al. |
| 7,963,433 B2 | 6/2011 | Whitman et al. |
| 7,967,831 B2 | 6/2011 | Rosenberg et al. |
| 7,988,027 B2 | 8/2011 | Olson et al. |
| 7,998,155 B2 | 8/2011 | Manzo |
| 8,011,550 B2 | 9/2011 | Aranyi et al. |
| 8,011,555 B2 | 9/2011 | Tarinelli et al. |
| 8,016,178 B2 | 9/2011 | Olson et al. |
| 8,021,375 B2 | 9/2011 | Aldrich et al. |
| 8,021,378 B2 | 9/2011 | Sixto, Jr. et al. |
| 8,038,686 B2 | 10/2011 | Huitema et al. |
| 8,056,565 B2 | 11/2011 | Zergiebel |
| 8,062,310 B2 | 11/2011 | Shibata et al. |
| 8,062,311 B2 | 11/2011 | Litscher et al. |
| 8,062,314 B2 | 11/2011 | Sixto, Jr. et al. |
| 8,066,720 B2 | 11/2011 | Knodel et al. |
| 8,066,721 B2 | 11/2011 | Kortenbach et al. |
| 8,066,722 B2 | 11/2011 | Miyagi et al. |
| 8,070,760 B2 | 12/2011 | Fujita |
| 8,074,857 B2 | 12/2011 | Peterson et al. |
| 8,075,571 B2 | 12/2011 | Vitali et al. |
| 8,080,021 B2 | 12/2011 | Griego |
| 8,083,668 B2 | 12/2011 | Durgin et al. |
| 8,088,061 B2 | 1/2012 | Wells et al. |
| 8,091,755 B2 | 1/2012 | Kayan et al. |
| 8,100,926 B1 | 1/2012 | Filshie et al. |
| 8,128,643 B2 | 3/2012 | Aranyi et al. |
| 8,133,240 B2 | 3/2012 | Damarati |
| 8,137,368 B2 | 3/2012 | Kayan et al. |
| 8,142,451 B2 | 3/2012 | Boulnois et al. |
| 8,157,145 B2 | 4/2012 | Shelton, IV et al. |
| 8,157,149 B2 | 4/2012 | Olson et al. |
| 8,157,151 B2 | 4/2012 | Ingmanson et al. |
| 8,172,859 B2 | 5/2012 | Matsuno et al. |
| 8,172,870 B2 | 5/2012 | Shipp |
| 8,177,797 B2 | 5/2012 | Shimoji et al. |
| 8,182,529 B2 | 5/2012 | Gordon et al. |
| 8,187,290 B2 | 5/2012 | Buckman et al. |
| 8,192,449 B2 | 6/2012 | Maier et al. |
| 8,211,119 B2 | 7/2012 | Palmer et al. |
| 8,211,120 B2 | 7/2012 | Itoh |
| 8,211,124 B2 | 7/2012 | Ainsworth et al. |
| 8,216,255 B2 | 7/2012 | Smith et al. |
| 8,216,257 B2 | 7/2012 | Huitema et al. |
| 8,236,012 B2 | 8/2012 | Molitor et al. |
| 8,241,322 B2 | 8/2012 | Whitman et al. |
| 8,246,634 B2 | 8/2012 | Huitema et al. |
| 8,246,635 B2 | 8/2012 | Huitema |
| 8,262,678 B2 | 9/2012 | Matsuoka et al. |
| 8,262,679 B2 | 9/2012 | Nguyen |
| 8,267,944 B2 | 9/2012 | Sorrentino et al. |
| 8,267,945 B2 | 9/2012 | Nguyen et al. |
| 8,267,946 B2 | 9/2012 | Whitfield et al. |
| 8,272,554 B2 | 9/2012 | Whitman et al. |
| 8,282,655 B2 | 10/2012 | Whitfield et al. |
| 8,287,559 B2 | 10/2012 | Barker et al. |
| 8,308,743 B2 | 11/2012 | Matsuno et al. |
| 8,313,497 B2 | 11/2012 | Walberg et al. |
| 8,328,822 B2 | 12/2012 | Huitema et al. |
| 8,336,556 B2 | 12/2012 | Zergiebel |
| 8,348,130 B2 | 1/2013 | Shah et al. |
| 8,357,171 B2 | 1/2013 | Whitfield et al. |
| 8,366,709 B2 | 2/2013 | Schechter et al. |
| 8,366,726 B2 | 2/2013 | Dennis |
| 8,371,491 B2 | 2/2013 | Huitema et al. |
| 8,372,095 B2 | 2/2013 | Viola |
| 8,382,773 B2 | 2/2013 | Whitfield et al. |
| 8,398,655 B2 | 3/2013 | Cheng et al. |
| 8,403,945 B2 | 3/2013 | Whitfield et al. |
| 8,403,946 B2 | 3/2013 | Whitfield et al. |
| 8,408,442 B2 | 4/2013 | Racenet et al. |
| 8,409,222 B2 | 4/2013 | Whitfield et al. |
| 8,409,223 B2 | 4/2013 | Sorrentino et al. |
| 8,419,752 B2 | 4/2013 | Sorrentino et al. |
| 8,430,892 B2 | 4/2013 | Bindra et al. |
| 8,444,660 B2 | 5/2013 | Adams et al. |
| 8,465,460 B2 | 6/2013 | Yodfat et al. |
| 8,465,502 B2 | 6/2013 | Zergiebel |
| 8,475,473 B2 | 7/2013 | Vandenbroek et al. |
| 8,480,688 B2 | 7/2013 | Boulnois et al. |
| 8,486,091 B2 | 7/2013 | Sorrentino et al. |
| 8,491,608 B2 | 7/2013 | Sorrentino et al. |
| 8,496,673 B2 | 7/2013 | Nguyen et al. |
| 8,506,580 B2 | 8/2013 | Zergiebel et al. |
| 8,512,357 B2 | 8/2013 | Viola |
| 8,518,055 B1 | 8/2013 | Cardinale et al. |
| 8,523,882 B2 | 9/2013 | Huitema et al. |
| 8,529,585 B2 | 9/2013 | Jacobs et al. |
| 8,529,586 B2 | 9/2013 | Rosenberg et al. |
| 8,529,588 B2 | 9/2013 | Ahlberg et al. |
| 8,545,486 B2 | 10/2013 | Malkowski |
| 8,556,920 B2 | 10/2013 | Huitema et al. |
| 8,568,430 B2 | 10/2013 | Shipp |
| 8,579,918 B2 | 11/2013 | Whitfield et al. |
| 8,585,716 B2 | 11/2013 | Roskopf et al. |
| 8,585,717 B2 | 11/2013 | Sorrentino et al. |
| 8,603,109 B2 | 12/2013 | Aranyi et al. |
| 8,623,044 B2 | 1/2014 | Timm et al. |
| 8,628,547 B2 | 1/2014 | Weller et al. |

(56) References Cited

U.S. PATENT DOCUMENTS

| | | |
|---|---|---|
| 8,632,520 B2 | 1/2014 | Otley |
| 8,636,191 B2 | 1/2014 | Meagher |
| 8,652,151 B2 | 2/2014 | Lehman et al. |
| 8,652,152 B2 | 2/2014 | Aranyi et al. |
| 8,663,247 B2 | 3/2014 | Menn et al. |
| 8,685,048 B2 | 4/2014 | Adams et al. |
| 8,690,899 B2 | 4/2014 | Kogiso et al. |
| 8,708,210 B2 | 4/2014 | Zemlok et al. |
| 8,708,213 B2 | 4/2014 | Shelton, IV et al. |
| 8,709,027 B2 | 4/2014 | Adams et al. |
| 8,715,299 B2 | 5/2014 | Menn et al. |
| 8,720,766 B2 | 5/2014 | Hess et al. |
| 8,734,469 B2 | 5/2014 | Pribanic et al. |
| 8,747,423 B2 | 6/2014 | Whitfield et al. |
| 8,753,356 B2 | 6/2014 | Vitali et al. |
| 8,758,392 B2 | 6/2014 | Crainich |
| 8,771,169 B2 | 7/2014 | Whitman et al. |
| 8,795,302 B2 | 8/2014 | Wild |
| 8,808,310 B2 | 8/2014 | Jones et al. |
| 8,814,884 B2 | 8/2014 | Whitfield et al. |
| 8,821,516 B2 | 9/2014 | Huitema |
| 8,839,954 B2 | 9/2014 | Disch |
| 8,845,659 B2 | 9/2014 | Whitfield et al. |
| 8,894,665 B2 | 11/2014 | Sorrentino et al. |
| 8,894,666 B2 | 11/2014 | Schulz et al. |
| 8,900,253 B2 | 12/2014 | Aranyi et al. |
| 8,915,930 B2 | 12/2014 | Huitema et al. |
| 8,915,931 B2 | 12/2014 | Boudreaux et al. |
| 8,920,438 B2 | 12/2014 | Aranyi et al. |
| 8,939,974 B2 | 1/2015 | Boudreaux et al. |
| 8,945,151 B2 | 2/2015 | Salas |
| 8,950,646 B2 | 2/2015 | Viola |
| 8,961,542 B2 | 2/2015 | Whitfield et al. |
| 8,968,337 B2 | 3/2015 | Whitfield et al. |
| 8,968,342 B2 | 3/2015 | Wingardner, III et al. |
| 8,973,804 B2 | 3/2015 | Hess et al. |
| 8,986,343 B2 | 3/2015 | Bourque et al. |
| 8,998,935 B2 | 4/2015 | Hart |
| 9,011,464 B2 | 4/2015 | Zammataro |
| 9,011,465 B2 | 4/2015 | Whitfield et al. |
| 9,028,511 B2 | 5/2015 | Weller et al. |
| 9,060,779 B2 | 6/2015 | Martinez |
| 9,084,604 B2 | 7/2015 | Litscher et al. |
| 9,089,334 B2 | 7/2015 | Sorrentino et al. |
| 9,113,892 B2 | 8/2015 | Malkowski et al. |
| 9,113,893 B2 | 8/2015 | Sorrentino et al. |
| 9,119,629 B2 | 9/2015 | Cardinale et al. |
| 9,186,136 B2 | 11/2015 | Malkowski et al. |
| 9,186,153 B2 | 11/2015 | Zammataro |
| 9,208,429 B2 | 12/2015 | Thornton et al. |
| 9,220,507 B1 | 12/2015 | Patel et al. |
| 9,226,825 B2 | 1/2016 | Starksen et al. |
| 9,232,947 B2 | 1/2016 | Brenner et al. |
| 9,326,776 B2 | 5/2016 | Gadberry et al. |
| 9,358,011 B2 | 6/2016 | Sorrentino et al. |
| 9,364,216 B2 | 6/2016 | Rockrohr et al. |
| 9,364,240 B2 | 6/2016 | Whitfield et al. |
| 9,370,400 B2 | 6/2016 | Parihar |
| 9,393,024 B2 | 7/2016 | Whitfield et al. |
| 9,408,610 B2 | 8/2016 | Hartoumbekis |
| 9,414,844 B2 | 8/2016 | Zergiebel et al. |
| 9,433,411 B2 | 9/2016 | Racenet et al. |
| 9,439,654 B2 | 9/2016 | Sorrentino et al. |
| 9,445,820 B2 | 9/2016 | Whiting |
| 9,468,444 B2 | 10/2016 | Menn et al. |
| 9,480,477 B2 | 11/2016 | Aranyi et al. |
| 9,480,480 B2 | 11/2016 | Santilli et al. |
| 9,486,225 B2 | 11/2016 | Michler et al. |
| 9,498,227 B2 | 11/2016 | Zergiebel et al. |
| 9,517,064 B2 | 12/2016 | Sarradon |
| 9,526,501 B2 | 12/2016 | Malkowski |
| 9,545,254 B2 | 1/2017 | Sorrentino et al. |
| 9,561,038 B2 | 2/2017 | Shelton, IV et al. |
| 9,566,066 B2 | 2/2017 | Kasvikis |
| 9,597,089 B2 | 3/2017 | Menn |
| 9,642,627 B2 | 5/2017 | Zammataro |
| 9,687,247 B2 | 6/2017 | Aranyi et al. |
| 9,717,505 B2 | 8/2017 | Whitfield et al. |
| 9,737,310 B2 | 8/2017 | Whitfield et al. |
| 9,750,500 B2 | 9/2017 | Malkowski |
| 9,763,668 B2 | 9/2017 | Whitfield et al. |
| 9,775,623 B2 | 10/2017 | Zammataro et al. |
| 9,775,624 B2 | 10/2017 | Rockrohr et al. |
| 9,848,886 B2 | 12/2017 | Malkowski et al. |
| 9,855,043 B2 | 1/2018 | Malkowski |
| 9,931,124 B2 | 4/2018 | Gokharu |
| 9,968,361 B2 | 5/2018 | Aranyi et al. |
| 9,968,362 B2 | 5/2018 | Malkowski et al. |
| 10,004,502 B2 | 6/2018 | Malkowski et al. |
| 10,159,484 B2 | 12/2018 | Sorrentino et al. |
| 10,159,491 B2 | 12/2018 | Gokharu |
| 10,159,492 B2 | 12/2018 | Zammataro |
| 10,166,027 B2 | 1/2019 | Aranyi et al. |
| 2002/0095177 A1* | 7/2002 | Kupferschmid ....... A61B 17/29 606/205 |
| 2003/0114867 A1 | 6/2003 | Bolduc et al. |
| 2003/0208231 A1 | 11/2003 | Williamson et al. |
| 2003/0229360 A1 | 12/2003 | Gayton |
| 2004/0133215 A1 | 7/2004 | Baxter |
| 2004/0138681 A1 | 7/2004 | Pier |
| 2004/0167545 A1 | 8/2004 | Sadler et al. |
| 2004/0176783 A1 | 9/2004 | Edoga et al. |
| 2004/0176784 A1 | 9/2004 | Okada |
| 2004/0193213 A1 | 9/2004 | Aranyi et al. |
| 2004/0232197 A1 | 11/2004 | Shelton et al. |
| 2005/0090837 A1 | 4/2005 | Sixto et al. |
| 2005/0096670 A1 | 5/2005 | Wellman et al. |
| 2005/0096671 A1 | 5/2005 | Wellman et al. |
| 2005/0107810 A1 | 5/2005 | Morales et al. |
| 2005/0107811 A1 | 5/2005 | Starksen et al. |
| 2005/0107871 A1 | 5/2005 | Realyvasquez et al. |
| 2005/0125010 A1 | 6/2005 | Smith et al. |
| 2005/0149068 A1 | 7/2005 | Williams et al. |
| 2005/0149069 A1 | 7/2005 | Bertolero et al. |
| 2005/0175703 A1 | 8/2005 | Hunter et al. |
| 2005/0177176 A1 | 8/2005 | Gerbi et al. |
| 2005/0216036 A1 | 9/2005 | Nakao |
| 2005/0216056 A1 | 9/2005 | Valdevit et al. |
| 2005/0222665 A1 | 10/2005 | Aranyi |
| 2005/0228416 A1 | 10/2005 | Burbank et al. |
| 2005/0256529 A1 | 11/2005 | Yawata et al. |
| 2005/0267495 A1 | 12/2005 | Ginn et al. |
| 2005/0273122 A1 | 12/2005 | Theroux et al. |
| 2005/0277956 A1 | 12/2005 | Francese et al. |
| 2005/0277958 A1 | 12/2005 | Levinson |
| 2005/0288689 A1 | 12/2005 | Kammerer et al. |
| 2006/0000867 A1 | 1/2006 | Shelton et al. |
| 2006/0004388 A1 | 1/2006 | Whayne et al. |
| 2006/0009789 A1 | 1/2006 | Gambale et al. |
| 2006/0009790 A1 | 1/2006 | Blake et al. |
| 2006/0009792 A1 | 1/2006 | Baker et al. |
| 2006/0020271 A1 | 1/2006 | Stewart et al. |
| 2006/0100649 A1 | 5/2006 | Hart |
| 2006/0163312 A1 | 7/2006 | Viola et al. |
| 2006/0173470 A1 | 8/2006 | Oray et al. |
| 2006/0190013 A1 | 8/2006 | Menn |
| 2006/0217749 A1 | 9/2006 | Wilson et al. |
| 2006/0224165 A1 | 10/2006 | Surti et al. |
| 2006/0224170 A1 | 10/2006 | Duff |
| 2006/0235439 A1 | 10/2006 | Molitor et al. |
| 2006/0241655 A1 | 10/2006 | Viola |
| 2006/0259045 A1 | 11/2006 | Damarati |
| 2006/0259049 A1 | 11/2006 | Harada et al. |
| 2007/0021766 A1 | 1/2007 | Belagali et al. |
| 2007/0038233 A1 | 2/2007 | Martinez et al. |
| 2007/0049947 A1 | 3/2007 | Menn et al. |
| 2007/0049949 A1 | 3/2007 | Manetakis |
| 2007/0049950 A1 | 3/2007 | Theroux et al. |
| 2007/0049951 A1 | 3/2007 | Menn |
| 2007/0083218 A1 | 4/2007 | A. Morris |
| 2007/0093790 A1 | 4/2007 | Downey et al. |
| 2007/0112365 A1 | 5/2007 | Hilal et al. |
| 2007/0118161 A1 | 5/2007 | Kennedy et al. |
| 2007/0118174 A1 | 5/2007 | Chu |

(56) References Cited

U.S. PATENT DOCUMENTS

| | | |
|---|---|---|
| 2007/0173866 A1 | 7/2007 | Sorrentino et al. |
| 2007/0185504 A1 | 8/2007 | Manetakis et al. |
| 2007/0191868 A1 | 8/2007 | Theroux et al. |
| 2007/0203510 A1 | 8/2007 | Bettuchi |
| 2007/0276417 A1 | 11/2007 | Mendes, Jr. et al. |
| 2007/0282355 A1 | 12/2007 | Brown et al. |
| 2007/0288039 A1 | 12/2007 | Aranyi et al. |
| 2007/0293875 A1 | 12/2007 | Soetikno et al. |
| 2008/0045981 A1 | 2/2008 | Margolin et al. |
| 2008/0051808 A1 | 2/2008 | Rivera et al. |
| 2008/0103510 A1 | 5/2008 | Taylor et al. |
| 2008/0147092 A1 | 6/2008 | Rogge et al. |
| 2008/0167665 A1 | 7/2008 | Arp et al. |
| 2008/0228199 A1 | 9/2008 | Cropper et al. |
| 2008/0255413 A1 | 10/2008 | Zemlok et al. |
| 2008/0255589 A1 | 10/2008 | Blakeney et al. |
| 2008/0306492 A1 | 12/2008 | Shibata et al. |
| 2008/0306493 A1 | 12/2008 | Shibata et al. |
| 2008/0312670 A1 | 12/2008 | Lutze et al. |
| 2009/0088783 A1 | 4/2009 | Kennedy et al. |
| 2009/0209946 A1 | 8/2009 | Swayze et al. |
| 2009/0228023 A1 | 9/2009 | Cui |
| 2009/0326558 A1 | 12/2009 | Cui et al. |
| 2010/0274264 A1 | 10/2010 | Schulz et al. |
| 2010/0318103 A1 | 12/2010 | Cheng et al. |
| 2011/0054498 A1 | 3/2011 | Monassevitch et al. |
| 2011/0144662 A1 | 6/2011 | McLawhorn et al. |
| 2011/0208211 A1 | 8/2011 | Whitfield et al. |
| 2011/0208212 A1 | 8/2011 | Zergiebel et al. |
| 2011/0218554 A1 | 9/2011 | Cheng et al. |
| 2011/0224700 A1 | 9/2011 | Schmidt et al. |
| 2011/0295290 A1 | 12/2011 | Whitfield |
| 2011/0313437 A1 | 12/2011 | Yeh |
| 2012/0046671 A1 | 2/2012 | Matsuoka et al. |
| 2012/0053402 A1 | 3/2012 | Conlon et al. |
| 2012/0226291 A1 | 9/2012 | Malizia et al. |
| 2012/0253298 A1 | 10/2012 | Henderson et al. |
| 2012/0265220 A1 | 10/2012 | Menn |
| 2012/0330326 A1 | 12/2012 | Creston et al. |
| 2013/0131697 A1 | 5/2013 | Hartoumbekis |
| 2013/0165951 A1 | 6/2013 | Blake, III |
| 2013/0172909 A1 | 7/2013 | Harris |
| 2013/0172910 A1 | 7/2013 | Malkowski |
| 2013/0175320 A1 | 7/2013 | Mandakolathur Vasudevan et al. |
| 2013/0226200 A1 | 8/2013 | Kappel et al. |
| 2013/0253540 A1 | 9/2013 | Castro et al. |
| 2014/0074143 A1 | 3/2014 | Fitzgerald et al. |
| 2014/0263565 A1 | 9/2014 | Lytle, IV et al. |
| 2014/0276970 A1 | 9/2014 | Messerly et al. |
| 2015/0032131 A1 | 1/2015 | Sorrentino et al. |
| 2015/0045816 A1 | 2/2015 | Aranyi et al. |
| 2015/0351771 A1 | 12/2015 | Malkowski et al. |
| 2015/0351772 A1 | 12/2015 | Malkowski et al. |
| 2016/0030044 A1 | 2/2016 | Zammataro |
| 2016/0113655 A1 | 4/2016 | Holsten |
| 2016/0151071 A1 | 6/2016 | Tokarz et al. |
| 2016/0213377 A1 | 7/2016 | Shankarsetty |
| 2016/0262764 A1 | 9/2016 | Gokharu |
| 2017/0049449 A1 | 2/2017 | Aranyi et al. |
| 2017/0065277 A1 | 3/2017 | Malkowski |
| 2017/0065281 A1 | 3/2017 | Zammataro |
| 2017/0086846 A1 | 3/2017 | Sorrentino et al. |
| 2017/0086850 A1 | 3/2017 | Zergiebel |
| 2017/0128071 A1* | 5/2017 | Holsten ............... A61B 17/105 |
| 2017/0172780 A1 | 6/2017 | Murthy Aravalli |
| 2017/0238936 A1 | 8/2017 | Mujawar |
| 2017/0258472 A1 | 9/2017 | Aranyi et al. |
| 2017/0325814 A1 | 11/2017 | Malkowski |
| 2017/0340325 A1 | 11/2017 | Baril et al. |
| 2017/0340331 A1 | 11/2017 | Hu et al. |
| 2017/0340332 A1 | 11/2017 | Whitfield et al. |
| 2017/0360449 A1 | 12/2017 | Rockrohr et al. |
| 2018/0008276 A1 | 1/2018 | Bhatnagar et al. |
| 2018/0008277 A1 | 1/2018 | Baril |
| 2018/0070952 A1 | 3/2018 | Malkowski et al. |
| 2018/0116671 A1 | 5/2018 | Prior |
| 2018/0116673 A1 | 5/2018 | Baril et al. |
| 2018/0116674 A1 | 5/2018 | Baril |
| 2018/0116675 A1 | 5/2018 | Baril |
| 2018/0116676 A1 | 5/2018 | Williams |
| 2018/0168660 A1 | 6/2018 | Gokharu |
| 2018/0214156 A1 | 8/2018 | Baril et al. |
| 2018/0221028 A1 | 8/2018 | Williams |
| 2018/0228492 A1 | 8/2018 | Aranyi et al. |
| 2018/0228567 A1 | 8/2018 | Baril et al. |
| 2018/0235632 A1 | 8/2018 | Mujawar et al. |
| 2018/0235633 A1 | 8/2018 | Baril et al. |
| 2018/0235637 A1* | 8/2018 | Xu ............... A61B 17/1285 |
| 2018/0242977 A1 | 8/2018 | Tan et al. |
| 2018/0263624 A1 | 9/2018 | Malkowski et al. |
| 2018/0271526 A1 | 9/2018 | Zammataro |
| 2018/0317927 A1 | 11/2018 | Cal et al. |
| 2018/0317928 A1 | 11/2018 | P V R |
| 2018/0325519 A1 | 11/2018 | Baril et al. |
| 2019/0000449 A1 | 1/2019 | Baril et al. |
| 2019/0000482 A1 | 1/2019 | Hu et al. |
| 2019/0000584 A1 | 1/2019 | Baril |

FOREIGN PATENT DOCUMENTS

| | | |
|---|---|---|
| CN | 104605911 B | 2/2017 |
| DE | 202005001664 U1 | 5/2005 |
| DE | 202007003398 U1 | 6/2007 |
| DE | 202009006113 U1 | 7/2009 |
| EP | 0000756 A1 | 2/1979 |
| EP | 0 406 724 A1 | 1/1991 |
| EP | 0514139 A2 | 11/1992 |
| EP | 0 732 078 A2 | 9/1996 |
| EP | 1769757 A1 | 4/2007 |
| GB | 2073022 A | 10/1981 |
| JP | 2003-033361 A | 2/2003 |
| JP | 2006-154230 A | 6/2006 |
| JP | 2006-277221 A | 10/2006 |
| JP | 2008-017876 A | 1/2008 |
| WO | 0042922 A1 | 7/2000 |
| WO | 2001-66001 A2 | 9/2001 |
| WO | 2001-67965 A1 | 9/2001 |
| WO | 2016192096 A1 | 12/2016 |
| WO | 2016192718 A2 | 12/2016 |
| WO | 2016197350 A1 | 12/2016 |
| WO | 2016206015 A1 | 12/2016 |

OTHER PUBLICATIONS

European Search Report corresponding to Patent Application EP 18155158.1 dated Jun. 28, 2018.
European Search Report corresponding to Patent Application EP 15877428.1 dated Jul. 2, 2018.
European Search Report corresponding to Patent Application EP 18157789.1 dated Jul. 5, 2018.
Office Action corresponding to Patent Application CA 2,972,444 dated Aug. 9, 2018.
European Search Report corresponding to Patent Application EP 18156458.4 dated Sep. 3, 2018.
European Search Report corresponding to Patent Application EP 18171682.0 dated Sep. 18, 2018.
European Search Report corresponding to Patent Application EP 15878354.8 dated Sep. 19, 2018.
European Search Report corresponding to Patent Application EP 18183394.8 dated Sep. 28, 2018.
Extended European Search Report corresponding to Patent Application EP 18163041.9 dated Sep. 28, 2018.
Extended European Search Report corresponding to Patent Application EP 18170524.5 dated Oct. 1, 2018.
Japanese Office Action corresponding to Patent Application JP 2017-536546 dated Oct. 15, 2018.
Extended European Search Report corresponding to Patent Application EP 18187640.0 dated Nov. 30, 2018.
Extended European Search Report corresponding to Patent Application EP 18187690.5 dated Nov. 30, 2018.
Chinese First Office Action corresponding to Patent Application CN

(56) References Cited

OTHER PUBLICATIONS 201510696298.9 dated Dec. 3, 2018.
Extended European Search Report corresponding to Patent Application EP 18158143.0 dated Dec. 5, 2018.
European Office Action corresponding to EP 12 152 989.5 dated May 4, 2015.
Australian Office Action corresponding to AU 2009212759 dated May 7, 2015.
Chinese Office Action corresponding to counterpart Int'l Appln No. CN 201210212642.9 dated Jun. 3, 2015.
European Office Action corresponding to counterpart Int'l Appln No. EP 04 719 757.9 dated Jun. 12, 2015.
European Office Action corresponding to counterpart Int'l Appln No. EP 13 166 382.5 dated Jun. 19, 2015.
Japanese Office Action corresponding to counterpart Int'l Application No. JP 2010-226908 dated Jun. 26, 2015.
Extended European Search Report corresponding to counterpart Int'l Application No. EP 15 15 5024.1 dated Jul. 17, 2015.
Extended European Search Report corresponding to counterpart Int'l Application No. EP 14 19 2026.4 dated Jul. 17, 2015.
Office Action corresponding to counterpart Int'l Application No. JP 2011-160126 dated Aug. 10, 2015.
Extended European Search Report corresponding to counterpart Int'l Application No. EP 14 15 0321.9 dated Sep. 23, 2015.
Extended European Search Report corresponding to counterpart Int'l Application No. EP 11 25 0675.3 dated Oct. 7, 2015.
Extended European Search Report corresponding to counterpart Int'l Application No. EP 11 25 0674.6 dated Oct. 7, 2015.
Extended European Search Report corresponding to counterpart Int'l Application No. EP 12 19 3447.5 dated Oct. 19, 2015.
Canadian Office Action corresponding to counterpart Int'l Application No. CA 2,675,875 dated Oct. 26, 2015.
Japanese Office Action corresponding to counterpart Int'l Application No. JP 2015-005629 dated Oct. 28, 2015.
Japanese Office Action corresponding to counterpart Int'l Application No. JP 2014-245081 dated Oct. 28, 2015.
Canadian Office Action corresponding to counterpart Int'l Application No. CA 2,675,921 dated Oct. 30, 2015.
Chinese Office Action corresponding to counterpart Int'l Application No. CN 201210555570.8 dated Nov. 2, 2015.
Canadian Office Action corresponding to counterpart Int'l Application No. CA 2,676,309 dated Nov. 3, 2015.
Canadian Office Action corresponding to counterpart Int'l Application No. CA 2,676,211 dated Nov. 24, 2015.
Canadian Office Action corresponding to counterpart Int'l Application No. CA 2,676,547 dated Nov. 25, 2015.
Extended European Search Report corresponding to counterpart Int'l Application No. EP 15 17 3809.3 dated Nov. 25, 2015.
Chinese Office Action corresponding to counterpart In'tl Application No. CN 201210586814.9 dated Dec. 2, 2015.
Extended European Search Report corresponding to counterpart Int'l Application No. EP 12 17 2940.4 dated Dec. 14, 2015.
Chinese First Office Action corresponding to counterpart Int'l Appln. No. CN 201210586826.1 dated Dec. 30, 2015.
Extended European Search Report corresponding to counterpart Int'l Appln. No. EP 15 18 5362.9 dated Feb. 12, 2016.
Extended European Search Report corresponding to counterpart Int'l Appln. No. EP 12 19 7813.4 dated Mar. 7, 2016.
Canadian Office Action corresponding to counterpart Int'l Appln. No. CA 2,676,465 dated Mar. 8, 2016.
Japanese Office Action corresponding to counterpart Int'l Appln. No. JP 2014-245081 dated Mar. 18, 2016.
Japanese Office Action corresponding to counterpart Int'l Appln. No. JP 2015-005629 dated Mar. 18, 2016.
Extended European Search Report corresponding to counterpart Int'l Appln. No. EP 15 19 3549.1 dated Mar. 22, 2016.
International Search Report and Written Opinion corresponding to counterpart Int'l Appln. No. PCT/CN2015/082199 dated Mar. 31, 2016.
Extended European Search Report corresponding to counterpart Int'l Appln. No. EP 15 19 7251.0 dated Apr. 8, 2016.
Extended European Search Report corresponding to counterpart Int'l Appln. No. EP 16 15 0739.7 dated May 17, 2016.
Canadian Office Action corresponding to counterpart Int'l Appln. No. CA 2,716,672 dated May 31, 2016.
Canadian Office Action corresponding to counterpart Int'l Appln. No. CA 2,717,448 dated May 31, 2016.
Canadian Office Action corresponding to counterpart Int'l Appln. No. CA 2,721,951 dated Jun. 1, 2016.
Partial European Search Report corresponding to counterpart Int'l Appln. No. EP 16 15 0287.7 dated Jun. 16, 2016.
Chinese Second Office Action corresponding to counterpart Int'l Appln. No. CN 201210555570.8 dated Jun. 20, 2016.
Chinese First Office Action corresponding to Chinese Appln. No. CN 201410076318.8 dated Jan. 23, 2017.
Extended European Search Report corresponding to European Appln. No. EP 16 18 3184.7 dated Jan. 24, 2017.
Japanese Office Action corresponding to Japanese Appln. No. JP 2016-097807 dated Feb. 14, 2017.
European Office Action corresponding to European Appln. No. EP 12 19 34475 dated Apr. 4, 2017.
Chinese First Office Action corresponding to Chinese Appln. No. CN 201410008877.5 dated Apr. 6, 2017.
Extended European Search Report corresponding to European Appln. No. EP 17 15 3714.5 dated May 11, 2017.
Extended European Search Report corresponding to European Appln. No. EP 17 15 8519.3 dated May 19, 2017.
Extended European Search Report corresponding to European Appln. No. EP 17 15 7606.9 dated May 22, 2017.
European Office Action corresponding to European Appln. No. EP 11 25 0674.6 dated May 23, 2017.
Canadian Office Action corresponding to Canadian Appln. No. CA 2,743,402 dated May 30, 2017.
The extended European Search Report corresponding to European Application No. EP 07 25 3905.9, completed Jan. 29, 2008; dated Feb. 7, 2008; (7 Pages).
International Search Report corresponding to International Application No. PCT-US08-58185, completed Sep. 4, 2008; dated Sep. 9, 2008; (2 Pages).
The International Search Report corresponding to International Application No. PCT-US08-59859, completed Sep. 14, 2008; dated Sep. 18, 2008; (2 Pages).
The extended European Search Report corresponding to European Application No. EP 07 25 3807.7, completed Nov. 7, 2008; dated Nov. 26, 2008; (11 Pages).
The extended European Search Report corresponding to European Application No. EP 09 25 2049.3, completed Dec. 11, 2009; dated Jan. 12, 2010; (3 Pages).
The extended European Search Report corresponding to European Application No. EP 09 25 2050.1, completed Dec. 23, 2009; dated Jan. 21, 2010; (3 Pages).
The extended European Search Report corresponding to European Application No. EP 09 25 2051.9, completed Dec. 21, 2009; dated Jan. 28, 2010; (3 Pages).
The extended European Search Report corresponding to European Application No. EP 09 25 2052.7, completed Nov. 16, 2009; dated Nov. 24, 2009; (3 Pages).
The extended European Search Report corresponding to European Application No. EP 09 25 2053.5, completed Nov. 24, 2009; dated Dec. 1, 2009; (3 Pages).
The extended European Search Report corresponding to European Application No. EP 09 25 2054.3, completed Jan. 7, 2010; dated Jan. 22, 2010; (3 Pages).
The extended European Search Report corresponding to European Application No. EP 09 25 2056.8, completed Jan. 8, 2010; dated Feb. 5, 2010; (3 Pages).
The extended European Search Report corresponding to European Application No. EP 10 25 0497.4, completed May 4, 2010; dated May 12, 2010; (6 Pages).
The extended European Search Report corresponding to European Application No. EP 10 25 2079.8, completed Mar. 8, 2011; dated Mar. 17, 2011; (3 Pages).

(56) References Cited

OTHER PUBLICATIONS

The European Search Report corresponding to European Application No. EP 05 81 0218.7, completed Apr. 18, 2011; dated May 20, 2011; (3 pages).
The European Search Report corresponding to European Application No. EP 05 80 7612.6, completed May 2, 2011; dated May 20, 2011; (3 pages).
The extended European Search Report corresponding to European Application No. EP 10 25 1737.2, completed May 9, 2011; dated May 20, 2011; (4 pages).
The extended European Search Report corresponding to European Application No. EP 11 25 0214.1, completed May 25, 2011; dated Jun. 1, 2011; (3 Pages).
The extended European Search Report corresponding to European Application No. EP 11 00 2681.2, completed May 31, 2011; dated Jun. 10, 2011; (3 Pages).
The European Search Report corresponding to European Application No. EP 05 80 2686.5, completed Jan. 9, 2012; dated Jan. 18, 2012; (3 Pages).
The extended European Search Report corresponding to European Application No. EP 11 15 1313.9, completed Mar. 20, 2012 and dated Apr. 12, 2012; (5 Pages).
The extended European Search Report corresponding to European Application No. EP 12 16 1291.5, completed Apr. 24, 2012 and dated May 4, 2012; (5 Pages).
The extended European Search Report corresponding to European Application No. EP 12 16 5891.8, completed Jun. 12, 2012 and dated Jun. 20, 2012; (6 Pages).
The extended European Search Report corresponding to European Application No. EP 12 16 2288.0, completed Jun. 4, 2012 and dated Jul. 7, 2012; (6 Pages).
The extended European Search Report corresponding to European Application No. EP 12 16 4955.2, completed Aug. 23, 2012 and dated Sep. 4, 2012; (5 Pages).
The extended European Search Report corresponding to European Application No. EP 11 25 0754.6, completed Oct. 22, 2012 and dated Oct. 31, 2012; (6 Pages).
The extended European Search Report corresponding to European Application No. EP 12 18 6401.1, completed Nov. 22, 2012 and dated Nov. 30, 2012; (7 Pages).
The extended European Search Report corresponding to European Application No. EP 12 18 6448.2, completed Nov. 28, 2012 and dated Dec. 10, 2012; (6 Pages).
The extended European Search Report corresponding to European Application No. EP 12 19 1706.6, completed Dec. 19, 2012 and dated Jan. 8, 2013; (6 Pages).
The Extended European Search Report corresponding to European Application No. EP 12 19 8745.7, completed Mar. 19, 2013 and dated Apr. 11, 2013; (8 Pages).
The Extended European Search Report corresponding to European Application No. EP 12 15 2989.5, completed Apr. 9, 2013 and dated Apr. 18, 2013; (9 Pages).
The Extended European Search Report corresponding to European Application No. EP 08 73 2820.9, completed Jul. 2, 2013 and dated Jul. 9, 2013; (10 Pages).
The Extended European Search Report corresponding to European Application No. EP 13 17 2008.8, completed Aug. 14, 2013 and dated Aug. 28, 2013; (8 Pages).
The Extended European Search Report corresponding to European Application No. EP 13 16 6382.5, completed Nov. 19, 2013 and dated Nov. 28, 2013; (8 Pages).
The Extended European Search Report corresponding to European Application No. EP 11 25 0194.5, completed Nov. 25, 2013 and dated Dec. 3, 2013; (8 pages).
The Extended European Search Report corresponding to European Application No. EP 10 25 1798.4, completed Dec. 12, 2013 and dated Jan. 2, 2014; (9 Pages).
"Salute II Disposable Fixation Device", Technique Guide—Laparoscopic and Open Inguinal and Ventral Hernia Repair; Davol, A Bard Company, 2006; (7 Pages).
The Extended European Search Report corresponding to EP 10 25 2112.7, completed Jul. 29, 2014 and dated Aug. 5, 2014; (8 pp).
The Extended European Search Report corresponding to EP 14 15 1673.2, completed Apr. 25, 2014 and dated May 8, 2014; (8 pp).
Japanese Office Action corresponding to JP 2011-160130 dated Dec. 1, 2014.
Chinese Office Action corresponding to CN 201210015011.8 dated Jan. 4, 2015.
Japanese Office Action corresponding to JP 2011-160126 dated Jan. 9, 2015.
Japanese Office Action corresponding to JP 2011-184521 dated Jan. 15, 2015.
Extended European Search Report corresponding to 14 18 2236.1 dated Jan. 20, 2015.
Chinese Office Action corresponding to CN 201110201736.1 dated Feb. 9, 2015.
Extended European Search Report corresponding to EP 14 16 1540.1 dated Feb. 27, 2015.
Australian Office Action corresponding to AU 2010226985 dated Mar. 31, 2015.
Australian Office Action corresponding to AU 2013211526 dated Apr. 6, 2015.
Australian Office Action corresponding to AU 2011211463 dated Apr. 13, 2015.
Australian Office Action corresponding to AU 2013254887 dated Apr. 14, 2015.
Japanese Office Action corresponding to JP 2013-225272 dated May 1, 2015.
European Office Action corresponding to European Appln. No. EP 16 15 9324.9 dated Aug. 7, 2017.
Chinese First Office Action corresponding to Chinese Appln. No. CN 2014104295806 dated Aug. 31, 2017.
Extended European Search Report corresponding to European Appln. No. EP 17 17 3508.7 dated Sep. 29, 2017.
Chinese Second Office Action corresponding to Chinese Appln. No. CN 201410076318.8 dated Oct. 10, 2017.
Extended European Search Report corresponding to European Appln. No. EP 17 18 0570.8 dated Dec. 6, 2017.

\* cited by examiner

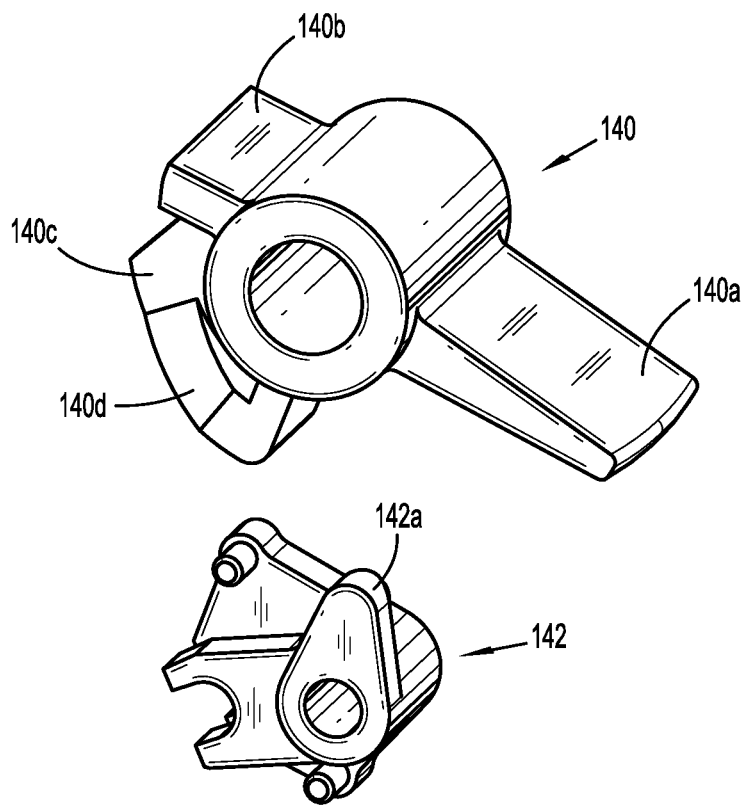
FIG. 5
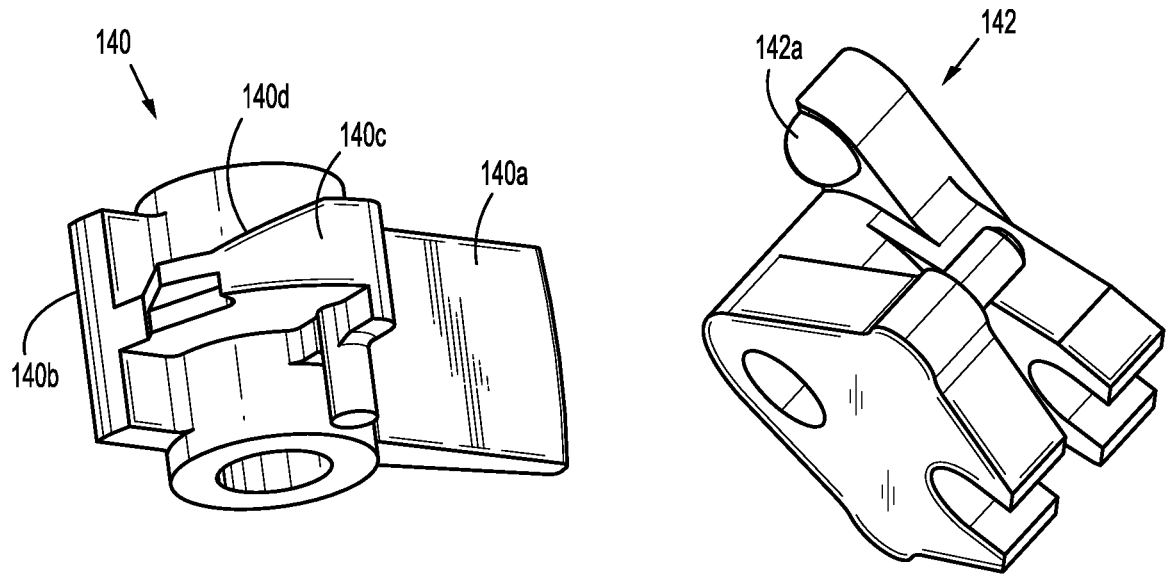
FIG. 6  FIG. 7

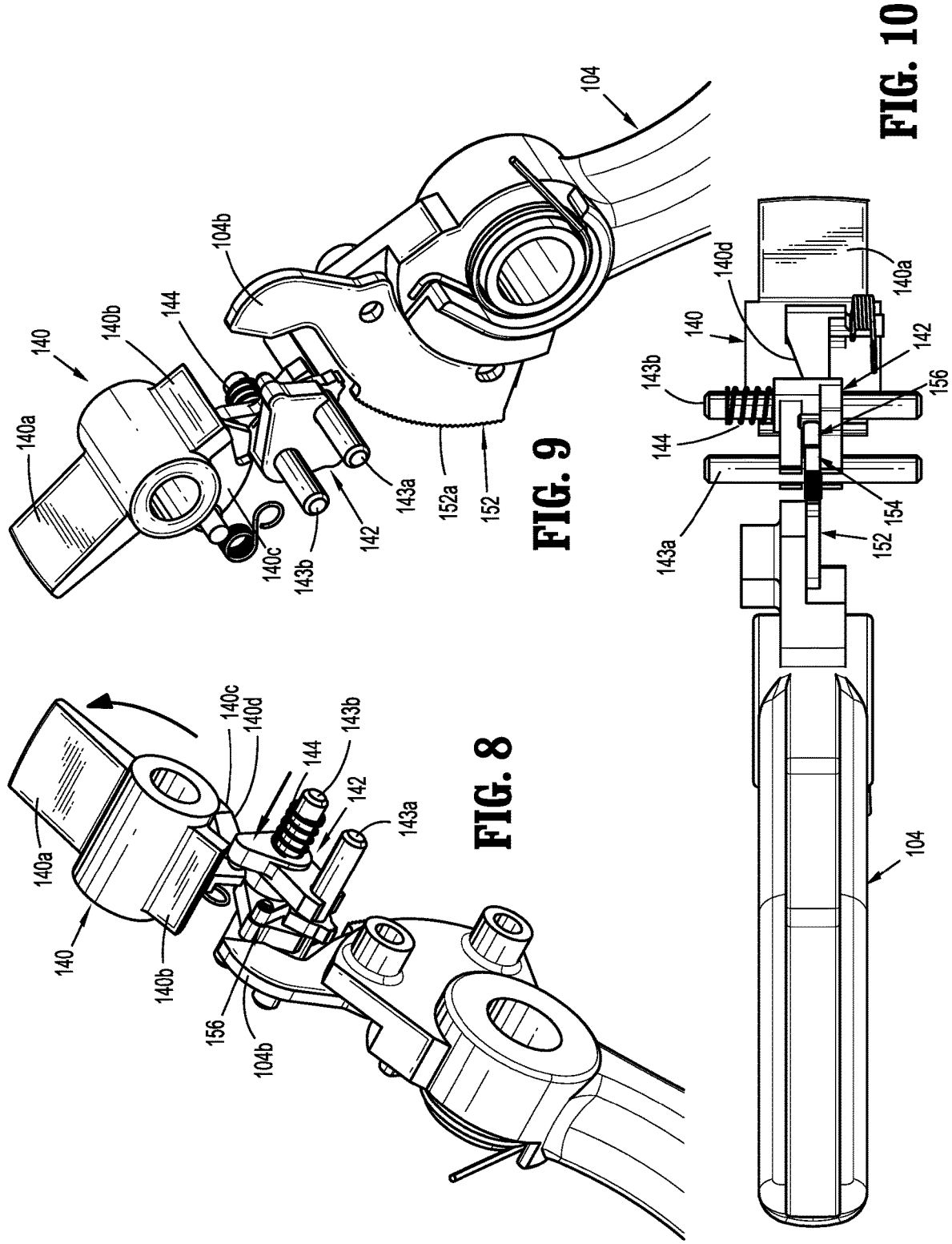

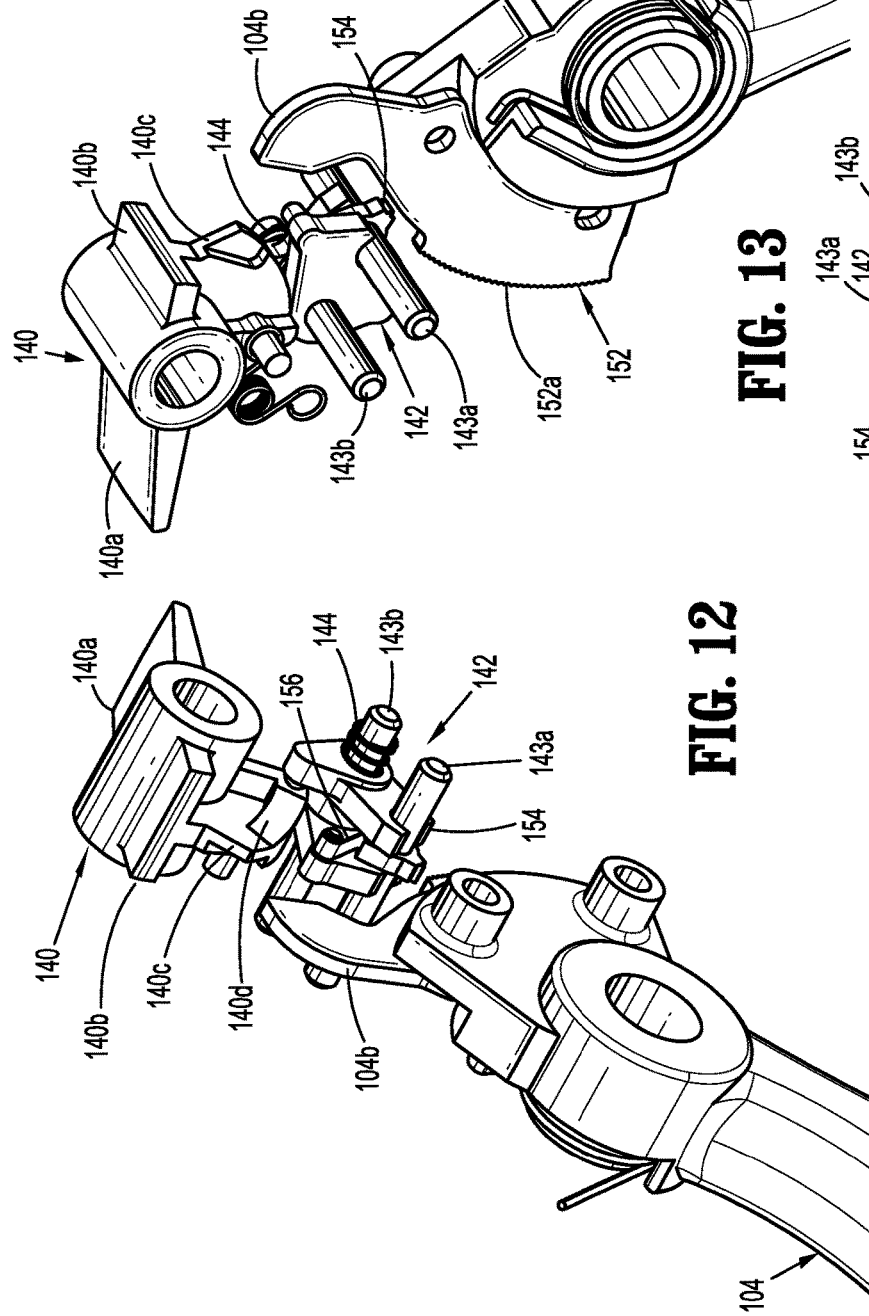
FIG. 12
FIG. 13
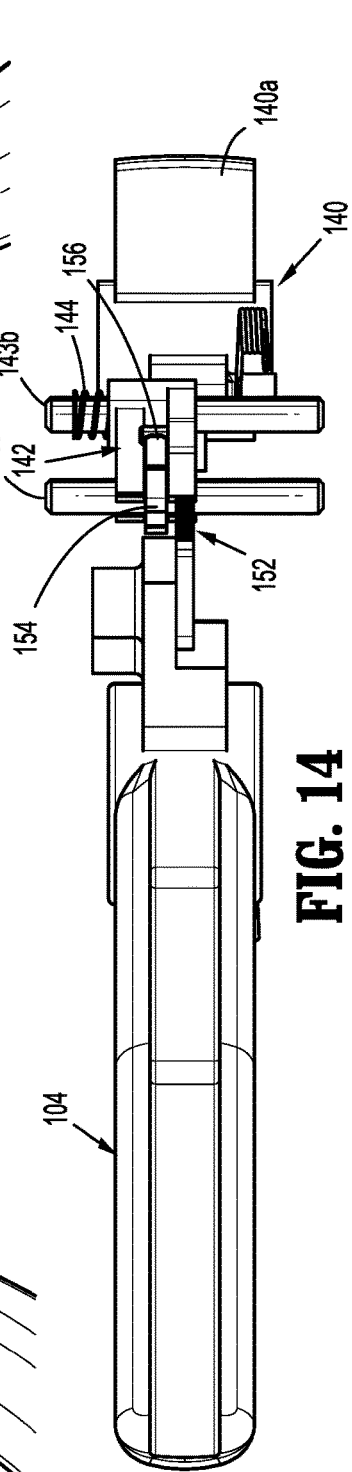
FIG. 14

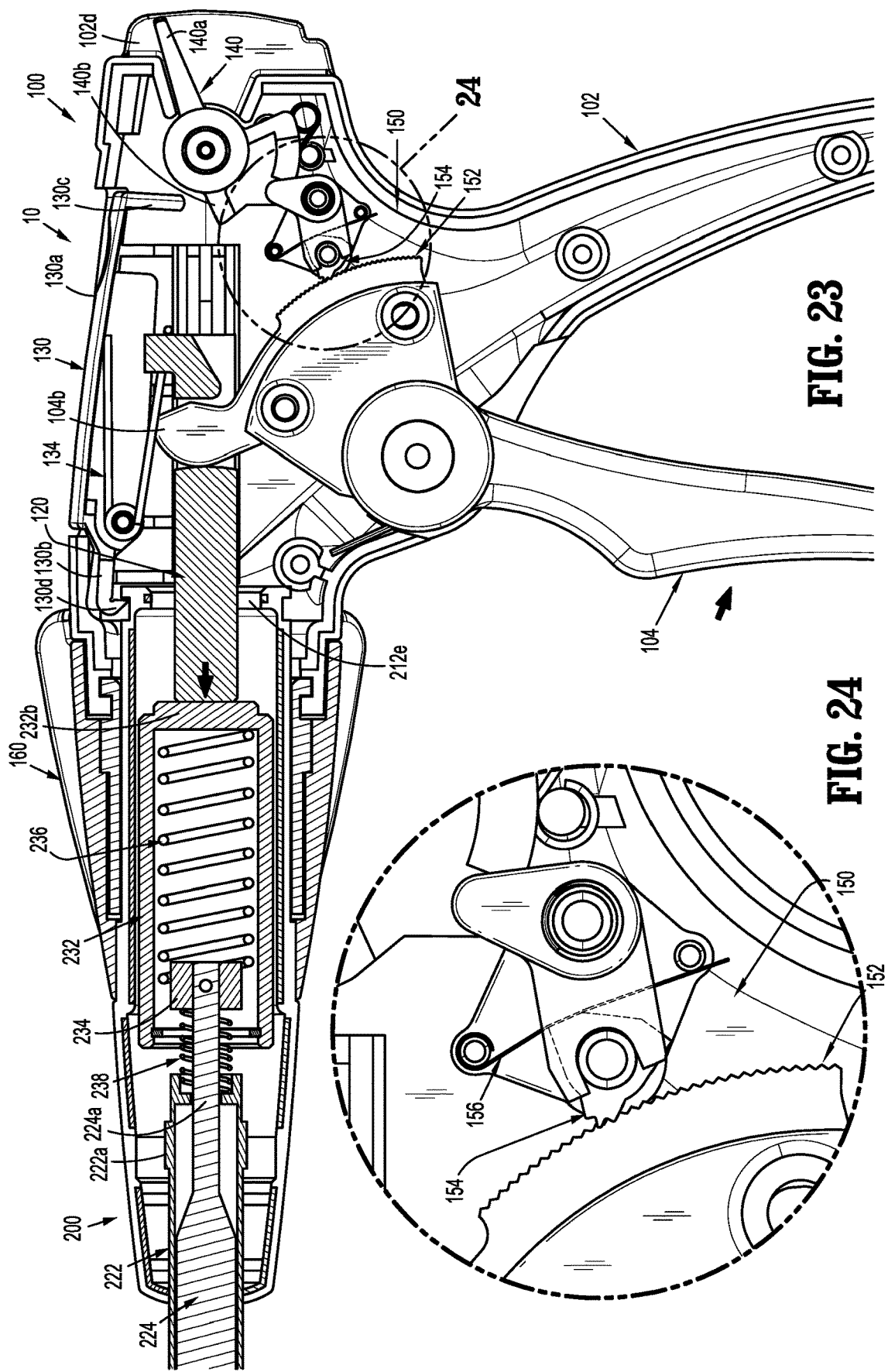

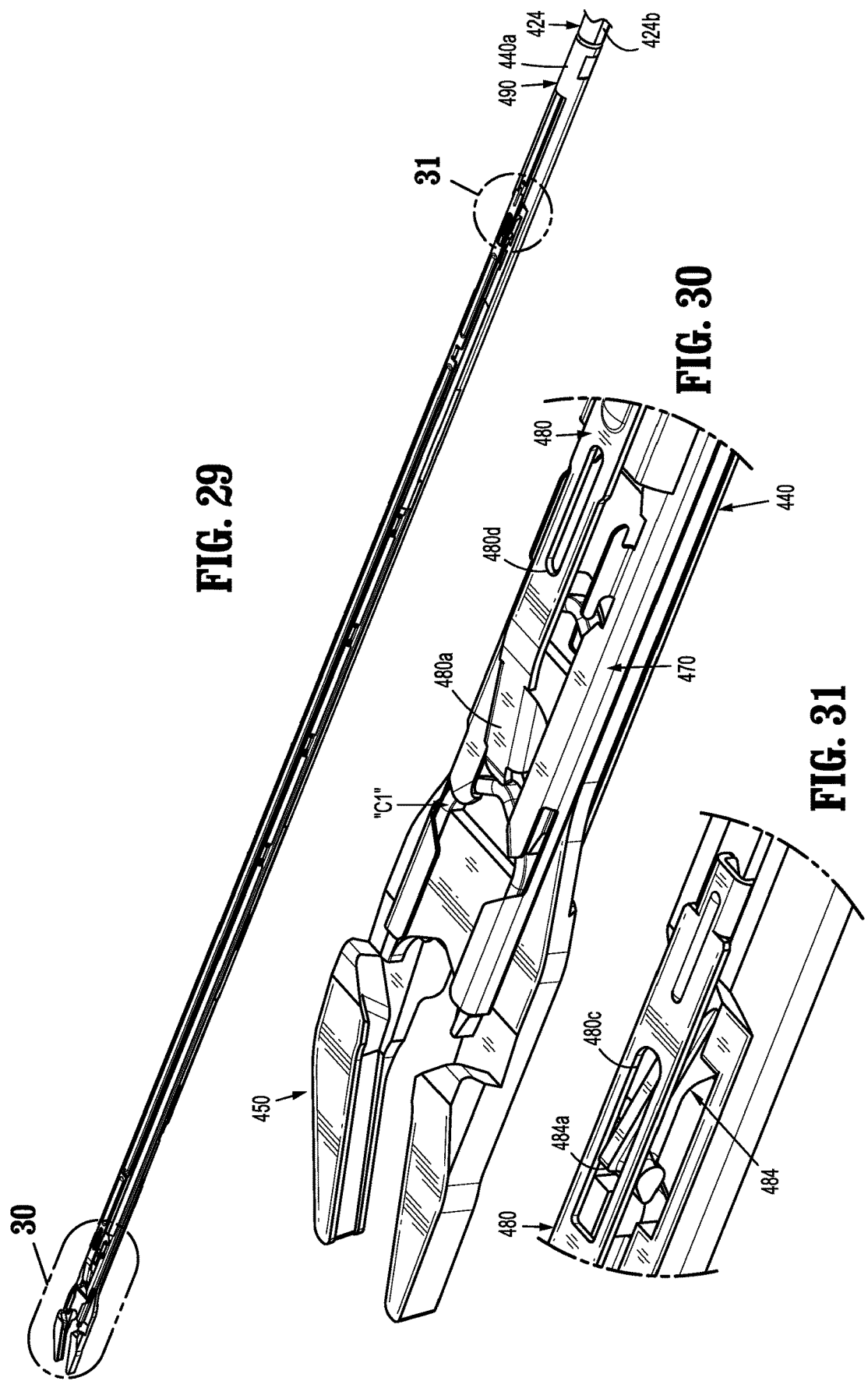

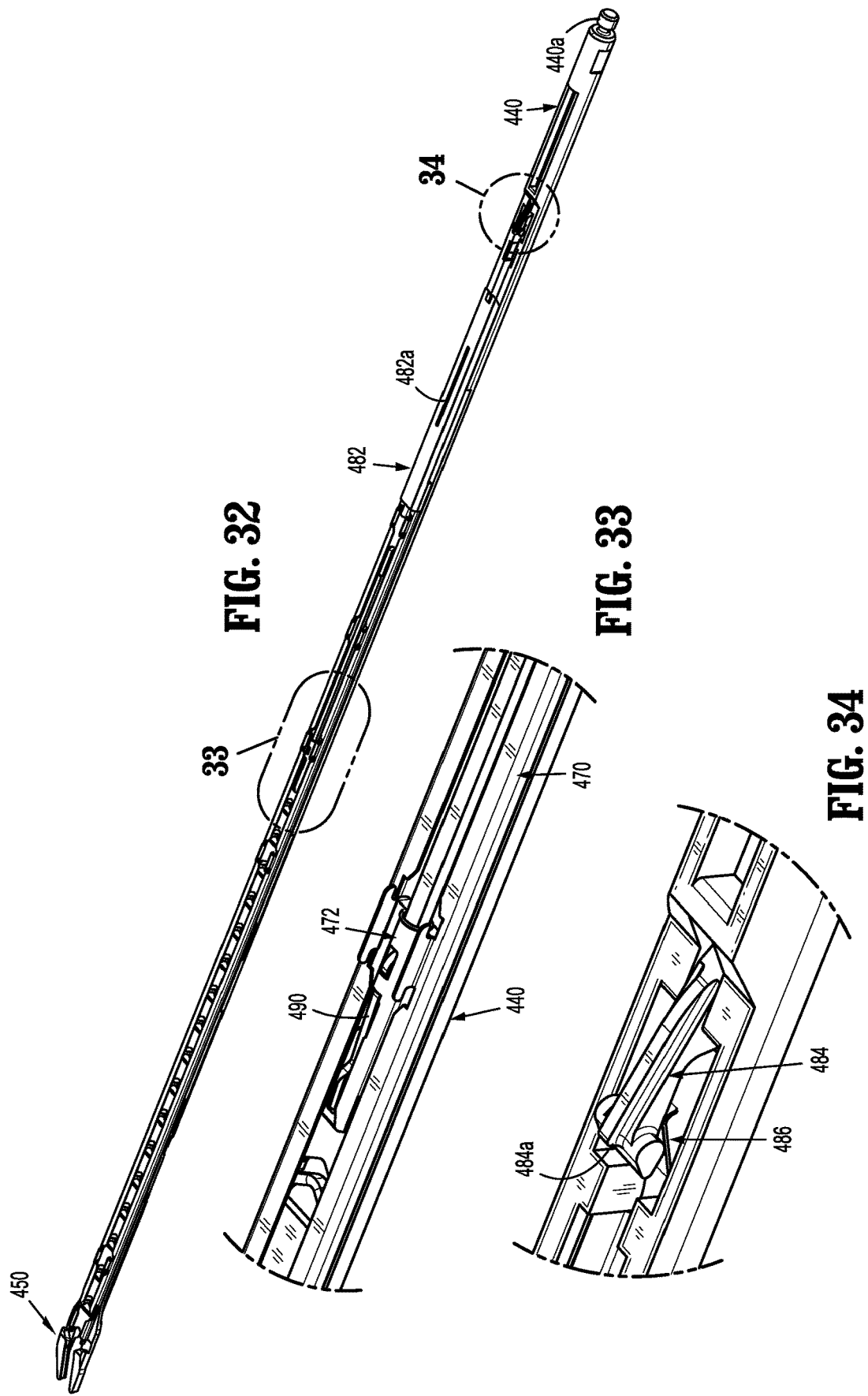

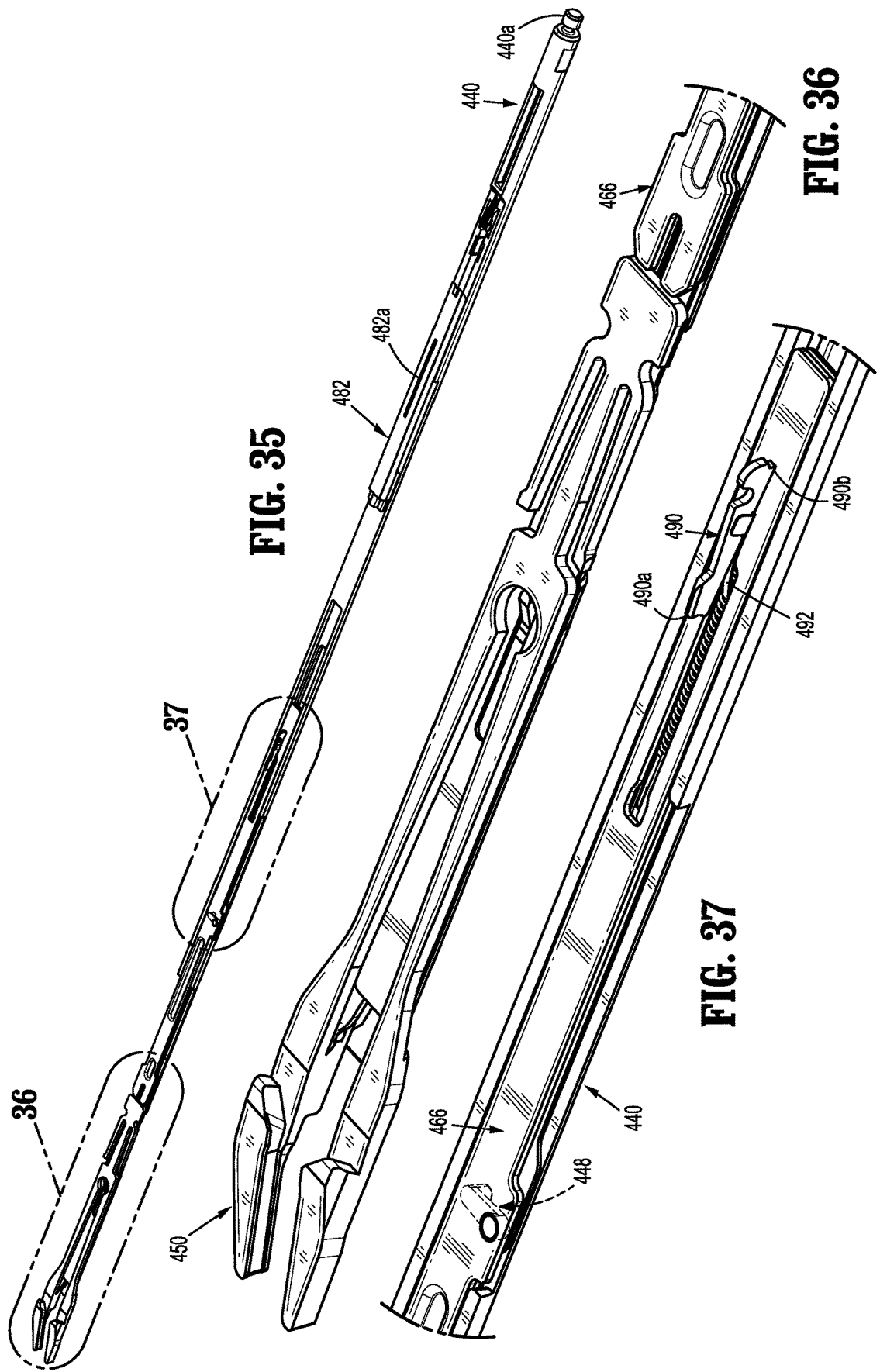

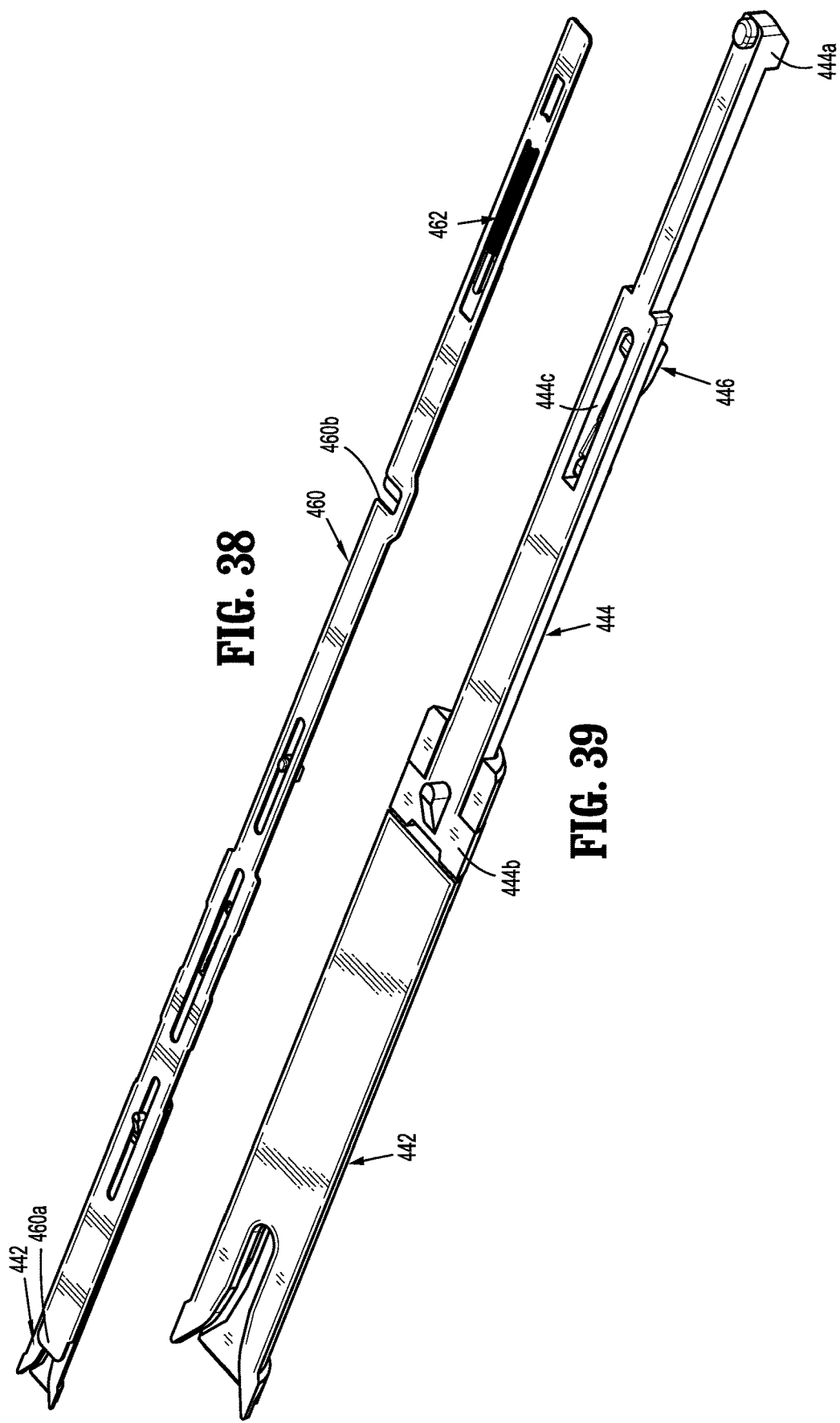

ENDOSCOPIC REPOSABLE SURGICAL CLIP APPLIER

CROSS-REFERENCE TO RELATED APPLICATIONS

This application claims the benefit of and priority to U.S. Provisional Patent Application No. 62/415,573 filed Nov. 1, 2016, the entire disclosure of which is incorporated by reference herein.

BACKGROUND

Technical Field

The technical field relates to surgical clip appliers. More particularly, the present disclosure relates to endoscopic reposable surgical clip appliers having a reusable handle assembly, at least one reusable shaft assembly, and at least one disposable clip cartridge assembly.

Description of Related Art

Endoscopic surgical staplers and surgical clip appliers are known in the art and are used for a number of distinct and useful surgical procedures. In the case of a laparoscopic surgical procedure, access to the interior of an abdomen is achieved through narrow tubes or cannulas inserted through a small entrance incision in the skin. Minimally invasive procedures performed elsewhere in the body are often generally referred to as endoscopic procedures. Typically, a tube or cannula device is extended into the patient's body through the entrance incision to provide an access port. The port allows the surgeon to insert a number of different surgical instruments therethrough using a trocar and for performing surgical procedures far removed from the incision.

During a majority of these procedures, the surgeon must often terminate the flow of blood or another fluid through one or more vessels. The surgeon will often use a particular endoscopic surgical clip applier to apply a surgical clip to a blood vessel or another duct to prevent the flow of body fluids therethrough during the procedure.

Endoscopic surgical clip appliers having various sizes (e.g., diameters), that are configured to apply a variety of diverse surgical clips, are known in the art, and which are capable of applying a single or multiple surgical clips during an entry to the body cavity. Such surgical clips are typically fabricated from a biocompatible material and are usually compressed over a vessel. Once applied to the vessel, the compressed surgical clip terminates the flow of fluid therethrough.

Endoscopic surgical clip appliers that are able to apply multiple clips in endoscopic or laparoscopic procedures during a single entry into the body cavity are described in commonly-assigned U.S. Pat. Nos. 5,084,057 and 5,100,420 to Green et al., which are both incorporated by reference in their entirety. Another multiple endoscopic surgical clip applier is disclosed in commonly-assigned U.S. Pat. No. 5,607,436 by Pratt et al., the contents of which is also hereby incorporated by reference herein in its entirety. These devices are typically, though not necessarily, used during a single surgical procedure. U.S. Pat. No. 5,695,502 to Pier et al., the disclosure of which is hereby incorporated by reference herein, discloses a resterilizable endoscopic surgical clip applier. The endoscopic surgical clip applier advances and forms multiple clips during a single insertion into the body cavity. This resterilizable endoscopic surgical clip applier is configured to receive and cooperate with an interchangeable clip magazine so as to advance and form multiple clips during a single entry into a body cavity.

During endoscopic or laparoscopic procedures it may be desirable and/or necessary to use different size surgical clips or different configured surgical clips depending on the underlying tissue or vessels to be ligated. In order to reduce overall costs of an endoscopic surgical clip applier, it is desirable for a single endoscopic surgical clip applier to be loadable with and capable of firing different size surgical clips as needed.

Accordingly, a need exists for endoscopic surgical clip appliers that include reusable handle assemblies, reusable shaft assemblies, and disposable clip cartridge assemblies, with each clip cartridge assembly being loaded with a particularly sized clip (e.g., relatively small, relatively medium, or relatively large).

SUMMARY

The present disclosure relates to reposable endoscopic surgical clip appliers.

According to an aspect of the present disclosure, a hub assembly for use with an endoscopic assembly of a reposable surgical clip applier is provided including an outer housing and a drive assembly supported within the outer housing. The drive assembly includes a cartridge cylinder slidably supported within the outer housing, a plunger translatably supported within the outer housing, a first biasing element interposed between the cartridge cylinder and the outer housing, and a second biasing element interposed between the cartridge cylinder and the plunger. The plunger is slidably coupled to the cartridge cylinder on a proximal end thereof. The first biasing element has a first threshold and the second biasing element has a second threshold that is greater than the first threshold such that when a force applied to the cartridge cylinder exceeds the first threshold, the cartridge cylinder and plunger translate simultaneously and when a force applied to the cartridge cylinder exceeds the second threshold the cartridge cylinder translates relative to the plunger.

The first biasing element may be slidably retained within a cavity defined through a distal portion of the cartridge cylinder.

In embodiments, the cartridge cylinder may further include a longitudinally extending boss disposed within the cavity.

In embodiments, a bore may be defined through a distal portion of the longitudinally extending boss.

In embodiments, the hub assembly may further include a pin fixedly retained within the bore of the longitudinally extending boss and slidably retained within a slot defined through a proximal portion of the plunger. The pin may be configured to slidably couple the plunger to the cartridge cylinder.

A proximal portion of the plunger may define a pair of wings on opposed side surfaces thereof that are configured to engage the first biasing element.

An inner portion of the outer housing may define an annular groove that defines proximal and distal facing surfaces.

The proximal facing surface of the annular groove may be configured to engage a distal portion of the second biasing element.

In embodiments, the hub assembly may further include a radially extending flange disposed on a proximal portion of the cartridge cylinder. A distal portion of the radially extending flange may be configured to engage a proximal portion of the second biasing member.

A proximal portion of the radially extending flange may be configured to abut the distal facing surface of the annular groove of the outer housing.

According to another embodiment of the present disclosure, an endoscopic assembly for use with a reposable surgical clip applier includes a shaft assembly having an outer tube and a pair of jaws fixedly supported in, and extending from a distal end thereof and a hub assembly configured for selective connection to an actuation assembly of the reposable surgical clip applier. The hub assembly includes an outer housing and a drive assembly supported within the outer housing. The drive assembly includes a cartridge cylinder slidably supported within the outer housing, a plunger translatably supported within the outer housing, a first biasing element interposed between the cartridge cylinder and the outer housing, and a second biasing element interposed between the cartridge cylinder and the plunger. The plunger is slidably coupled to the cartridge cylinder on a proximal end thereof. The first biasing element has a first threshold and the second biasing element has a second threshold that is greater than the first threshold such that when a force applied to the cartridge cylinder exceeds the first threshold, the cartridge cylinder and plunger translate simultaneously and when a force applied to the cartridge cylinder exceeds the second threshold the cartridge cylinder translates relative to the plunger.

The first biasing element may be slidably retained within a cavity defined through a distal portion of the cartridge cylinder.

In embodiments, the cartridge cylinder may further include a longitudinally extending boss disposed within the cavity.

In embodiments, a bore may be defined through a distal portion of the longitudinally extending boss.

In embodiments, the hub assembly may further include a pin fixedly retained within the bore of the longitudinally extending boss and slidably retained within a slot defined through a proximal portion of the plunger. The pin may be configured to slidably couple the plunger to the cartridge cylinder.

A proximal portion of the plunger may define a pair of wings on opposed side surfaces thereof that are configured to engage the first biasing element.

An inner portion of the outer housing may define an annular groove that defines proximal and distal facing surfaces.

The proximal facing surface of the annular groove may be configured to engage a distal portion of the second biasing element.

In embodiments, the hub assembly may further include a radially extending flange disposed on a proximal portion of the cartridge cylinder. A distal portion of the radially extending flange may be configured to engage a proximal portion of the second biasing member.

A proximal portion of the radially extending flange may be configured to abut the distal facing surface of the annular groove of the outer housing.

BRIEF DESCRIPTION OF THE DRAWINGS

A particular embodiment of a surgical clip applier is disclosed herein with reference to the drawings wherein:

FIG. 5 is an enlarged perspective view of the indicated area of detail of FIG. 4, illustrating a pawl switch and a pawl actuator of the handle assembly of FIG. 1;

FIG. 6 is a further perspective view of the pawl switch of FIG. 5;

FIG. 7 is a further perspective view of the pawl actuator of FIG. 5;

FIGS. 8-9 are various perspective views of the pawl switch and the pawl actuator of the handle assembly, shown in operation with the pawl switch in an un-actuated condition and the pawl actuator engaged with a pawl of a ratchet assembly;

FIG. 10 is a top plan view of the pawl switch and the pawl actuator of the handle assembly, shown in operation with the pawl switch in the un-actuated condition and the pawl actuator engaged from the pawl of the ratchet assembly;

FIGS. 12-13 are various perspective views of the pawl switch and the pawl actuator of the handle assembly, shown in operation with the pawl switch in the actuated condition and the pawl actuator disengaged from the pawl of the ratchet assembly;

FIG. 14 is a top plan view of the pawl switch and the pawl actuator of the handle assembly, shown in operation with the pawl switch in the actuated condition and the pawl actuator disengaged from the pawl of the ratchet assembly;

FIG. 23 is a longitudinal, transverse cross-sectional view illustrating an initial actuation of the handle assembly with the first endoscopic assembly connected thereto;

FIG. 24 is an enlarged view of the indicated area of detail of FIG. 23;

FIG. 29 is a perspective view of the distal end of the shaft assembly of the second endoscopic assembly with an outer tube removed therefrom;

FIG. 30 is an enlarged view of the indicated area of detail of FIG. 29;

FIG. 31 is an enlarged view of the indicated area of detail of FIG. 29;

FIG. 32 is a perspective view of the distal end of the shaft assembly of the second endoscopic assembly with the outer tube and a pusher bar removed therefrom;

FIG. 33 is an enlarged view of the indicated area of detail of FIG. 32;

FIG. 34 is an enlarged view of the indicated area of detail of FIG. 32;

FIG. 35 is a perspective view of the distal end of the shaft assembly of the second endoscopic assembly with the outer tube, the pusher bar and a clip channel removed therefrom;

FIG. 36 is an enlarged view of the indicated area of detail of FIG. 35;

FIG. 37 is an enlarged view of the indicated area of detail of FIG. 35;

FIG. 38 is a perspective view of the distal end of the shaft assembly of the second endoscopic assembly with the outer tube, the pusher bar, the clip channel and a pair of jaws and a filler component removed therefrom;

FIG. 39 is a perspective view of the distal end of the shaft assembly of the second endoscopic assembly with the outer tube, the pusher bar, the clip channel, the pair of jaws, the filler component, and a wedge plate removed therefrom;

DETAILED DESCRIPTION OF EMBODIMENTS

Figure 1:
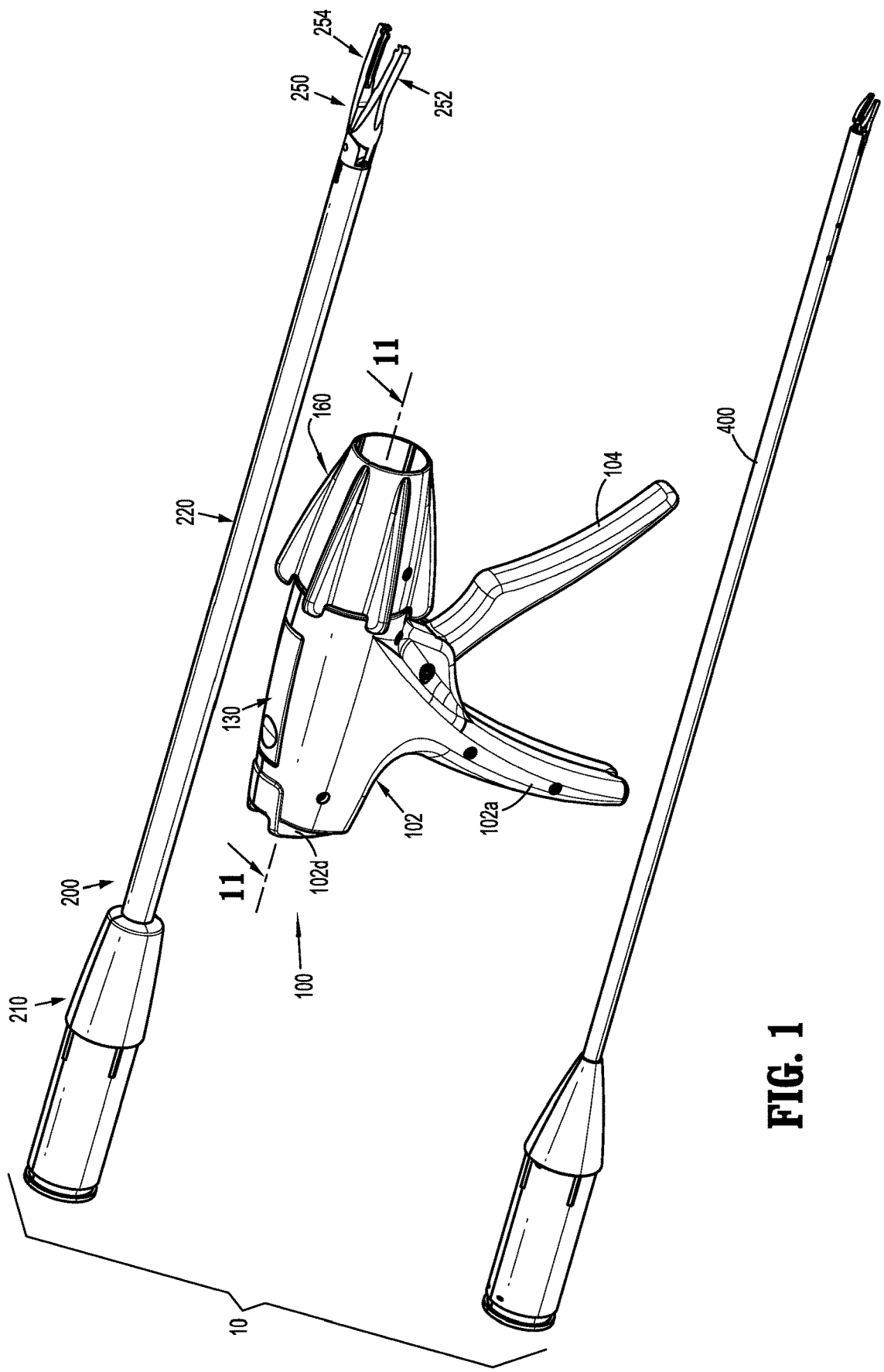
FIG. 1 is a perspective view of a reposable endoscopic surgical clip applier, according to the present disclosure including a reusable handle assembly, and a first endoscopic assembly and a second endoscopic assembly each selectively connectable to the handle assembly.
Figure 2:
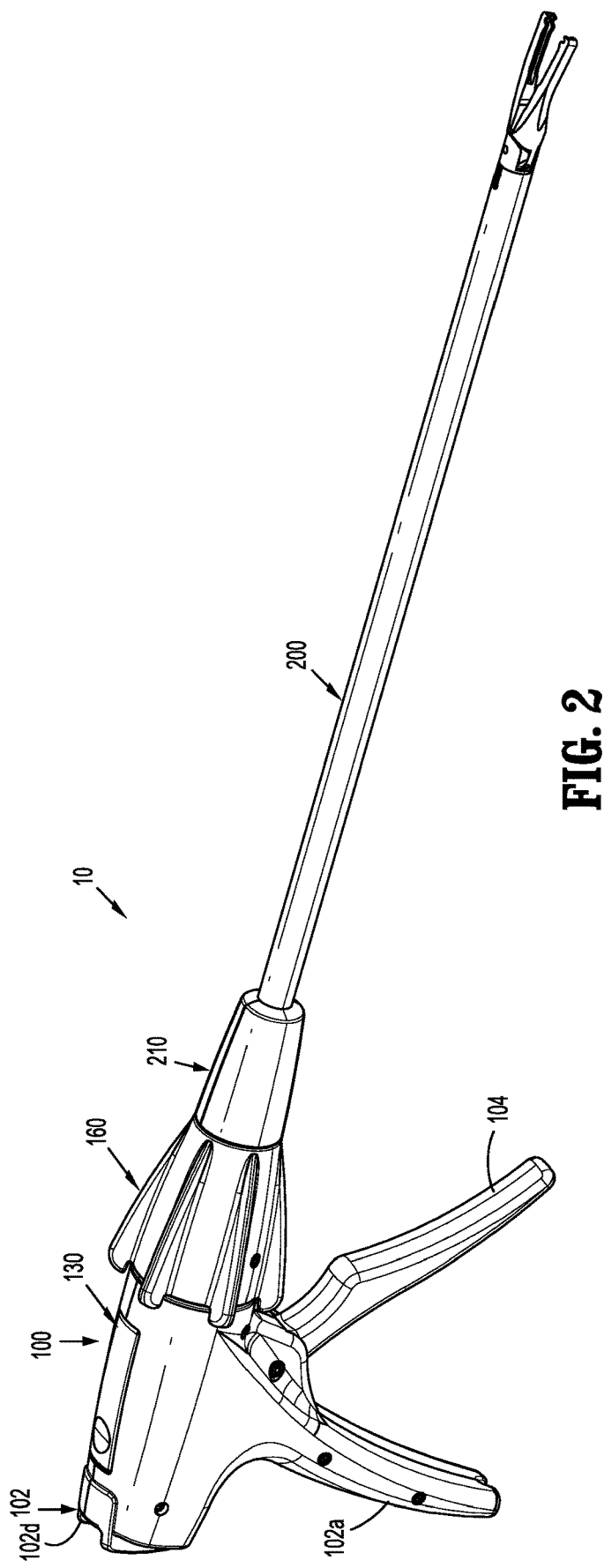
FIG. 2 is perspective view of the reposable endoscopic surgical clip applier including the reusable handle assembly and the first endoscopic assembly connected thereto.

Embodiments of reposable endoscopic surgical clip appliers, in accordance with the present disclosure, will now be described in detail with reference to the drawing figures wherein like reference numerals identify similar or identical structural elements. As shown in the drawings and described throughout the following description, as is traditional when referring to relative positioning on a surgical instrument, the term "proximal" refers to the end of the apparatus which is closer to the user and the term "distal" refers to the end of the apparatus which is further away from the user.

Referring now to FIGS. 1-29, an endoscopic surgical clip applier in accordance with an embodiment of the present disclosure, and assembly in a particular configuration, is generally designated as 10. Surgical clip applier 10 generally includes a reusable handle assembly or actuation assembly 100, at least one disposable or reusable endoscopic assembly 200 selectively connectable to and extendable distally from handle assembly 100; and optionally at least one disposable surgical clip cartridge assembly (not shown) selectively loadable into a shaft assembly of a respective endoscopic assembly 200.

Briefly, the shaft assembly of endoscopic assembly 200 may have various outer diameters such as, for example, about 5 mm or about 10 mm, depending on intended use. Further, the shaft assembly may have various relatively elongated or shortened lengths depending on intended use, such as, for example, in bariatric surgery. In one embodiment, in bariatric surgery, the shaft assembly may have a length of between about 30 cm and about 40 cm. Further, the shaft assembly may be configured to fire and form a specific type of surgical clip, either individually or multiply. However one skilled in the art should appreciate that the shaft assembly may have any length in excess of about 30 cm and the present disclosure is not limited to any of the above identified lengths.

In accordance with the present disclosure, as will be discussed in greater detail below, an endoscopic assembly or a surgical clip cartridge assembly (not shown) may be loaded with a particularly sized set of surgical clips (e.g., relatively small surgical clips, relatively medium surgical clips, or relatively large surgical clips). It is contemplated that clip cartridge assemblies may be configured to be selectively loaded into the shaft assembly of a respective endoscopic assembly 200, and to be actuated by the same or common handle assembly 100, to fire and form the surgical clip(s) loaded therein onto underlying tissue and/or vessels.

Figure 3:
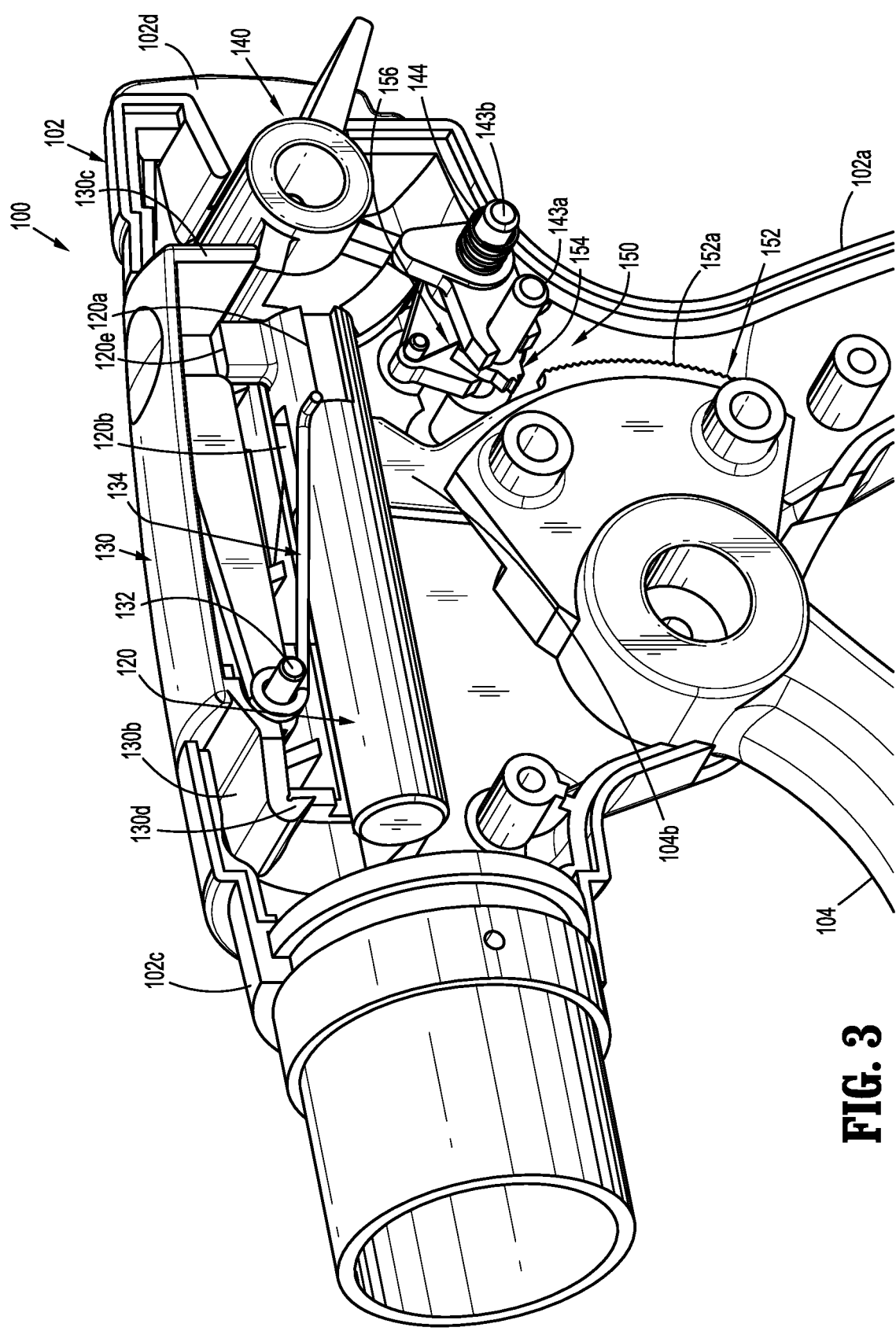
FIG. 3 is a perspective view of the handle assembly with at least a housing half-section removed therefrom.
Figure 4:
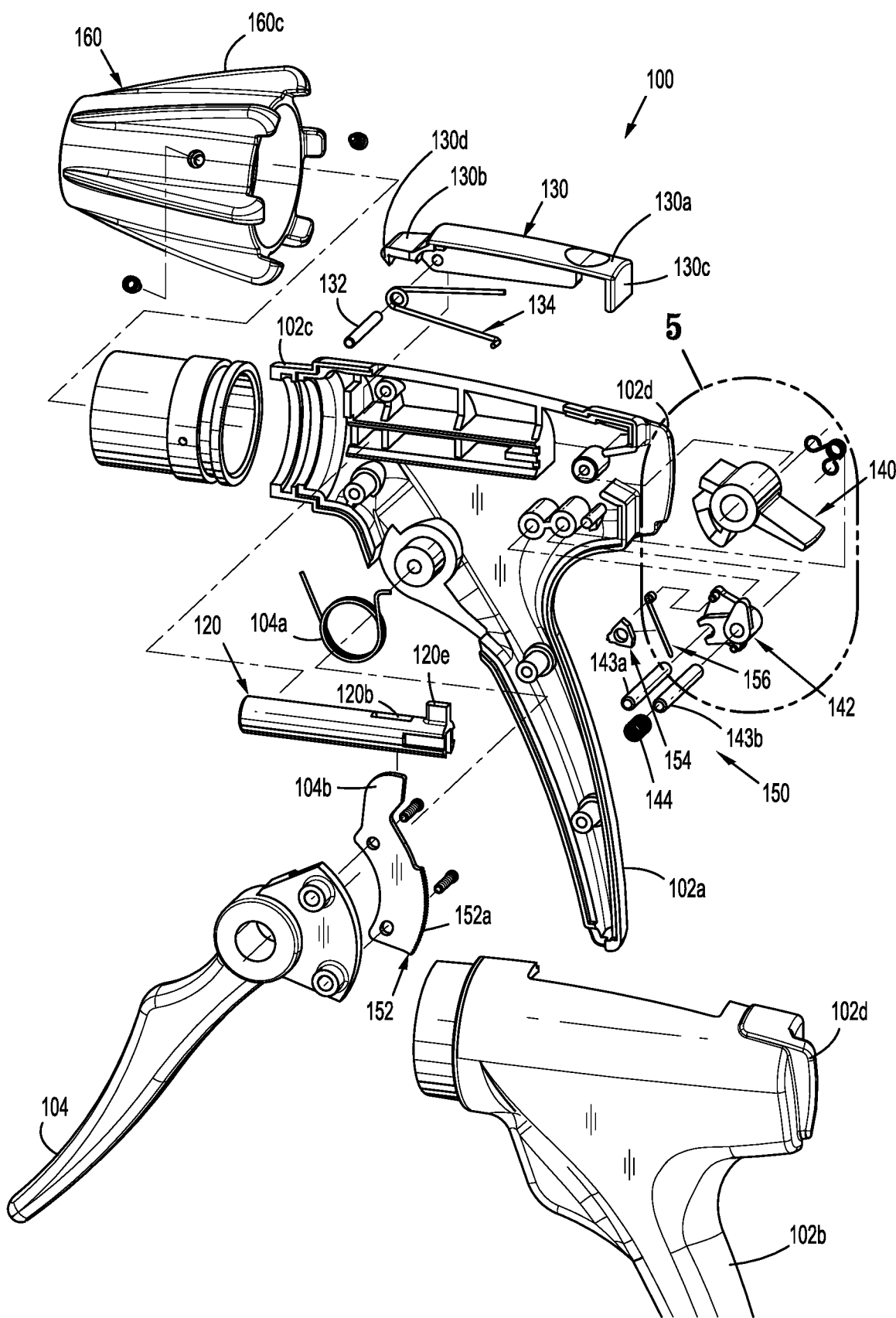
FIG. 4 is a perspective view, with parts separated, of the handle assembly of FIGS. 1-3.

Referring now to FIGS. 1-14, handle assembly 100 of surgical clip applier 10 is shown and will be described. Handle assembly 100 includes a housing 102 having a first or right side half-section 102a and a second or left side half-section 102b. Housing 102 of handle assembly 100 further includes or defines, as seen in FIGS. 3 and 4, a nose 102c. Housing 102 of handle assembly 100 may be formed of a suitable plastic or thermoplastic material. It is further contemplated that housing 102 of handle assembly 100 may be fabricated from stainless steel of the like.

Handle assembly 100 includes a trigger 104 pivotably supported between right side half-section 102a and left side half-section 102b of housing 102. Trigger 104 is biased by a biasing member 104a (e.g., a return spring, compression spring or torsion spring) to an un-actuated condition. Specifically, biasing member 104a (FIG. 4) acts on a feature of trigger 104 and on a feature of housing 102 to bias or urge trigger 104 to the un-actuated condition. Trigger 104 includes a drive arm 104b extending therefrom. Drive arm 104b may be integrally formed therewith or may be separately and fixedly secured to trigger 104. Drive arm 104b may define a curved, radiused or filleted upper distal surface.

As illustrated in FIGS. 3, 4 and 8-14, trigger 104 supports or is provided with at least one linear rack 152 of teeth 152a of a ratchet assembly 150, as will be described in detail below.

Figure 11:
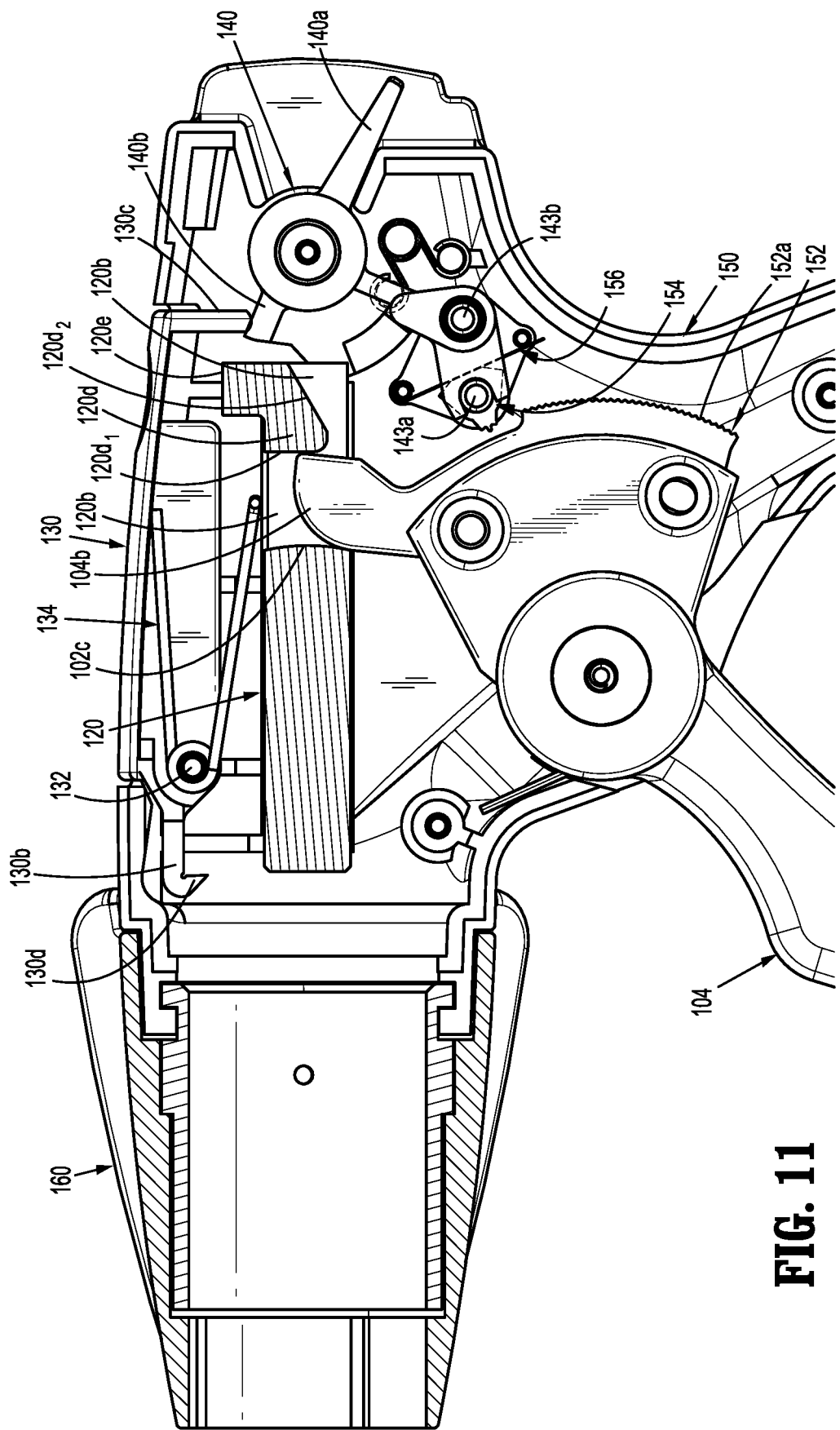
FIG. 11 is a transverse, cross-sectional view of the handle assembly of FIG. 1 as taken through 11-11 of FIG. 1, illustrating the pawl switch in an actuated condition.

With reference to FIGS. 3, 4, 11, handle assembly 100 includes a drive plunger 120 operatively connected to trigger 104. Specifically, drive plunger 120 is slidably supported within housing 102 and defines a pair of opposed, axially extending slots 120a formed in an outer surface thereof. Slots 120a of drive plunger 120 are configured to slidably engage or receive opposed tabs 102d of housing 102. Drive plunger 120 further defines a proximally extending trigger slot 120b formed in a proximal portion thereof for operatively receiving drive arm 104b of trigger 104. Trigger slot 120b defines a distal surface or wall 120c against which a distal surface of drive arm 104b of trigger 104 contacts in order to distally advance drive plunger 120 during an actuation of trigger 104.

Drive plunger 120 further includes a tooth 120d (FIG. 11) projecting into trigger slot 120b. Tooth 120d projects substantially toward trigger 104 and includes a distal surface or wall 120d1 (spaced proximally from distal surface or wall 120c of drive plunder 120), and a proximal, angled wall 120d2 tapering to a relatively smaller height in a proximal direction.

Drive plunger 120 additionally includes a tab or fin 120e projecting from a surface thereof. Tab 120e of drive plunger 120 may be substantially aligned or in registration with tooth 120d of drive plunger 120. Tab 120e of drive plunger 120 may project in a direction substantially opposite to tooth 120d of drive plunger 120 or to trigger 104.

With reference to FIGS. 1-4 and 11, handle assembly 100 includes an endoscopic assembly release lever 130 pivotally supported on and connected to housing 102 via a pivot pin 132. Pivot pin 132 is supported in housing 102. Release lever 130 includes a proximal end 130a extending proximally of pivot pin 132. Proximal end 130a of release lever 130 includes a wall 130c dimensioned to extend toward a pawl switch 140 of handle assembly 100, as will be described in greater detail below.

Release lever 130 includes a distal end 130b extending distally of pivot pin 132. Distal end 130b of release lever 130 includes a catch or tooth 130d projecting therefrom, in a direction towards drive plunger 120. Catch 130d may be located distal of drive plunger 120.

A biasing member 134, in the form of a leaf spring, may be provided which tends to bias distal end 130b and catch 130d of release lever 130 towards drive plunger 120 of handle assembly 100, and tends to bias proximal end 130a of release lever 130 away from pawl switch 140. Specifically, biasing member 134 tends to maintain catch 130d of release lever 130 in engagement with an engagement feature (e.g., annular channel 212c) of endoscopic assembly 200, as will be described in greater detail below.

With reference to FIGS. 3, 4 and 11-14, as mentioned above, handle assembly 100 includes a ratchet assembly 150 supported within housing 102. Ratchet assembly 150 includes, as also mentioned above, at least one linear rack 152 of teeth 152a supported on and projecting from trigger 104. Ratchet assembly 150 further includes a ratchet pawl 154 pivotally connected to housing 102 by a pawl pin at a location wherein pawl 154 is in substantial operative engagement with rack 152. Ratchet assembly 150 further includes a pawl spring 156 configured and positioned to bias pawl 154 into operative engagement with rack 152. Pawl spring 156 functions to maintain the tooth or teeth 154a of pawl 154 in engagement with teeth 152a of rack 152, as well as to maintain pawl 154 in a rotated or canted position.

Pawl 154 is engagable with rack 152 to restrict longitudinal movement of rack 152 and, in turn, trigger 104. In use, as trigger 104 is actuated (from a fully un-actuated position), rack 152 is also moved, into engagement with pawl 154. Rack 152 has a length which allows pawl 154 to reverse and advance back over rack 152, when rack 152 changes between proximal or distal movement, as trigger 104 reaches a fully actuated or fully un-actuated position. The relative lengths and sizes of rack 152 of ratchet assembly 150, trigger 104 and drive plunger 120 define a stroke length of trigger 104, drive plunger 120 or handle assembly 100 (e.g., a "full stroke").

Turning now to FIGS. 1, 2, 4, 11 and 18, handle assembly 100 includes a rotation knob 160 rotatably supported on nose 102c of housing 102. Rotation knob 160 includes a central axial bore 160a having an annular array of longitudinally extending grooves 160b (FIG. 18) formed in a surface thereof. Grooves 160b of rotation knob 160 function as clocking and alignment features for the connection of endoscopic assembly 200 with handle assembly 100. Rotation knob 160 further includes a plurality of finger grip ribs 160c projecting from an outer surface thereof.

With reference to FIGS. 3 and 4-14, handle assembly 100 further includes a pawl switch 140 and a pawl actuator 142 each pivotally supported in housing 102. Pawl switch 140 is operatively connected to pawl actuator 142 and is operable to selectively move pawl actuator 142 into or out of engagement with pawl spring 156, and in turn pawl 154, of ratchet assembly 150 whereby pawl 154 may be selectively engaged by pawl spring 156. In this manner, when pawl 154 is moved out of engagement with pawl spring 156, trigger 104 is free to open and close as needed due to pawl 154 having minimal blocking effect on rack 152 of ratchet assembly 150. As such, trigger 104 may be partially actuated (without having to be fully actuated), and may be returnable to a fully un-actuated position. Such a feature permits the user to partially squeeze or actuate trigger 104 for performing a cholangiogram procedure or the like.

Pawl switch 140 includes a finger lever 140a projecting from housing 102, whereby pawl switch 140 may be actuated by a finger of a user. Housing 102 of handle assembly 100 may be provided with guard walls 102d disposed on opposed sides of finger lever 140a in order to inhibit inadvertent actuation of pawl switch 140. Pawl switch 140 is movable, upon actuation of finger lever 140a, between a first position in which ratchet assembly 150 is "on" or "activated", and a second position in which ratchet assembly 150 is "off" or "de-activated." It is contemplated that pawl switch 140, and in turn ratchet assembly 150, default to the first position.

Pawl switch 140 further includes a first flange 140b projecting a first distance from a pivot point thereof, and a second flange 140c projecting a second distance from the pivot point thereof, wherein the projection of the second flange 140c is greater than the projection of the first flange 140b. First flange 140b of pawl switch 140 is selectively engagable by wall 130c of proximal end 130a of release lever 130. In this manner, each time an endoscopic assembly 200 is attached to handle assembly 100, and release lever 130 is actuated, wall 130c of release lever 130 engages first flange 140b of pawl switch 140 to move pawl switch to the first position (FIGS. 19-22).

Pawl switch 140 also includes a ramp or camming surface 140d projecting therefrom which selectively engages a tab or finger 142a of pawl actuator 142 to slidably move pawl actuator 142, and in turn pawl spring 156, into and out of operative engagement/registration with/from pawl 154.

Pawl actuator 142 is pivotally connected to housing 102 and operatively connected to pawl switch 140 such that actuation of pawl switch 140 actuates pawl actuator 142. Pawl actuator 142 is slidably supported on a pair of support pins 143a, 143b, and a biasing member 144 is provided to bias pawl actuator 142 against pawl switch 140. In operation, with reference to FIGS. 11-14, when pawl switch 140 is actuated to the second position, ramp or camming surface 140d of pawl switch 140 acts on tab 142a of pawl actuator 142 to transversely slide pawl actuator 142 along support pins 143a, 143b and move pawl spring 156 out of operative engagement/registration with pawl 154, thereby disabling the operability of ratchet assembly 150. Also, as pawl actuator 142 is slid transversely along support pins 143a, 143b, pawl actuator 142 biases biasing member 144.

Further in operation, with reference to FIGS. 8-10, when pawl switch 140 is actuated to the first position, ramp or camming surface 140d of pawl switch 140 is moved to permit biasing member 144 to expand and transversely slide pawl actuator 142 along support pins 143a, 143b, whereby pawl spring 156 is moved back into operative engagement/registration with pawl 154, thereby enabling or re-enabling the operability of ratchet assembly 150.

Turning now to FIGS. 1, 2, 16 and 17, an embodiment of an endoscopic assembly 200, of surgical clip applier 10, is shown and described. Endoscopic assembly 200 includes a hub assembly 210, a shaft assembly 220 extending from hub assembly 210, and a pair of jaws 250 pivotally connected to a distal end of shaft assembly 220. It is contemplated that endoscopic assembly 200 may be configured to close, fire or form surgical clips similar to those shown and described in U.S. Pat. No. 4,834,096, the entire content of which is incorporated herein by reference.

Hub assembly 210 functions as an adapter assembly which is configured for selective connection to rotation knob 160 and nose 102c of housing 102 of handle assembly 100. Hub assembly 210 includes an outer housing 212 having a cylindrical outer profile. Outer housing 212 includes a first or right side half section 212a, and a second or left side half section 212b. Outer housing 212 of hub assembly 210 defines an outer annular channel 212c formed in an outer surface thereof, and at least one (or an annular array) of axially extending ribs 212d projecting from an outer surface thereof. Outer annular channel 212c of outer housing 212 of endoscopic assembly 200 is configured to receive catch 130d of release lever 130 of handle assembly 100 (FIGS. 19-22) when endoscopic assembly 200 is coupled to handle assembly 100.

Ribs 212d of outer housing 212 function as a clocking/alignment feature during connection of endoscopic assembly 200 and handle assembly 100 with one another, wherein ribs 212d of outer housing 212 of endoscopic assembly 200 are radially and axially aligned with respective grooves 160b of rotation knob 160 of handle assembly 100. During connection of endoscopic assembly 200 and handle assembly 100, ribs 212d of outer housing 212 of endoscopic assembly 200 are slidably received in respective grooves 160b of rotation knob 160 of handle assembly 100.

The connection of hub assembly 210 of endoscopic assembly 200 with rotation knob 160 of handle assembly 100 enables endoscopic assembly 200 to rotate 360°, about a longitudinal axis thereof, relative to handle assembly 100.

Outer housing 212 of hub assembly 210 further defines an open proximal end 212e configured to slidably receive a distal end of drive plunger 120 of handle assembly 100, when endoscopic assembly 200 is coupled to handle assembly 100 and/or when surgical clip applier 10 is fired.

As mentioned above, endoscopic assembly 200 includes a shaft assembly 220 extending distally from hub assembly 210. Shaft assembly 220 includes an elongate outer tube 222 having a proximal end 222a supported and secured to outer housing 212 of hub assembly 210, a distal end 222b projecting from outer housing 212 of hub assembly 210, and a lumen 222c (FIGS. 15 and 17) extending longitudinally therethrough. Distal end 222b of outer tube 222 supports or defines an outer clevis 222d for pivotally supporting a pair of jaws 250, as will be described in greater detail below.

Shaft assembly 220 further includes an inner shaft 224 slidably supported within lumen 222c of outer tube 222. Inner shaft 224 includes a proximal end 224a projecting proximally from proximal end 222a of outer tube 222, and a distal end 224b defining an inner clevis 224c for supporting a cam pin 224d which engages camming slots 252c, 254c of a pair of jaws 250, as will be described in greater detail below.

Figure 15:
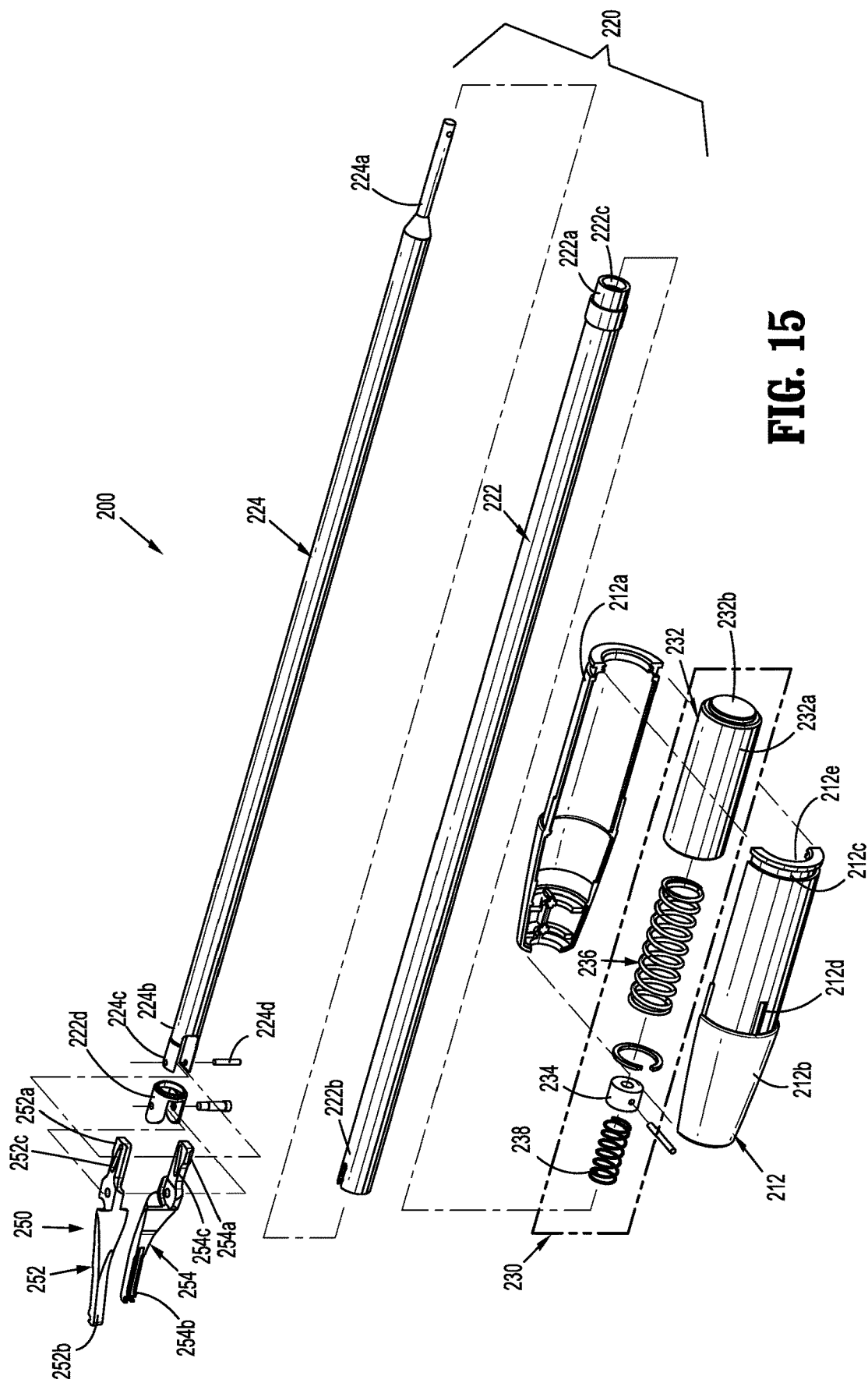
FIG. 15 is a perspective view, with parts separated, of the first endoscopic assembly of FIG. 1.
Figure 16:
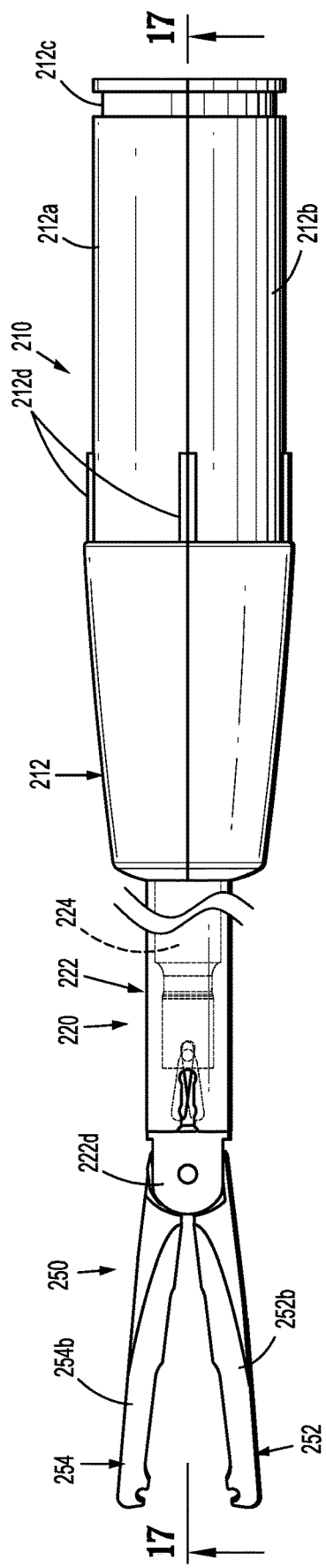
FIG. 16 is a top, plan view of the first endoscopic assembly of FIGS. 1 and 15.
Figure 17:
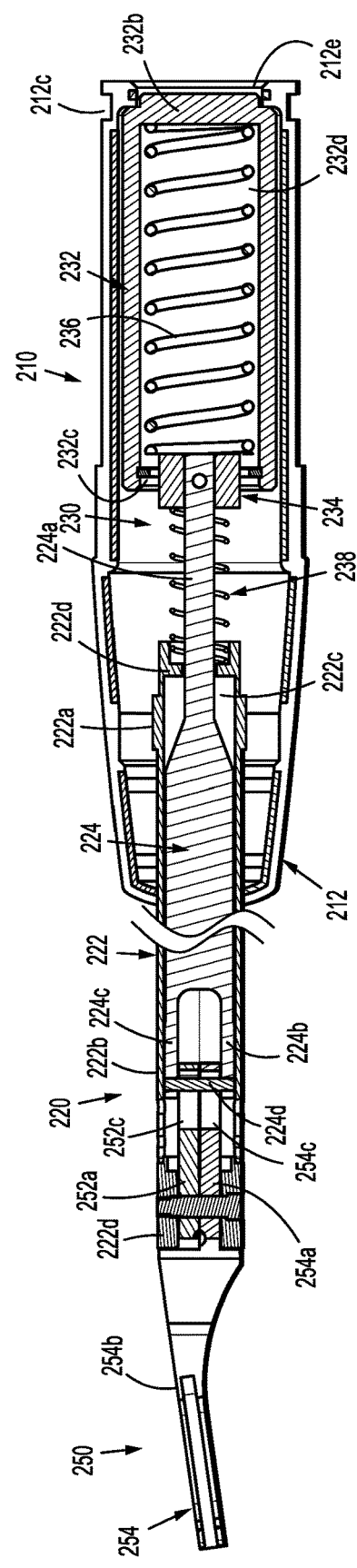
FIG. 17 is a transverse, cross-sectional view of the first endoscopic assembly of FIGS. 1 and 15-16, as taken through 17-17 of FIG. 16.
Figure 18:
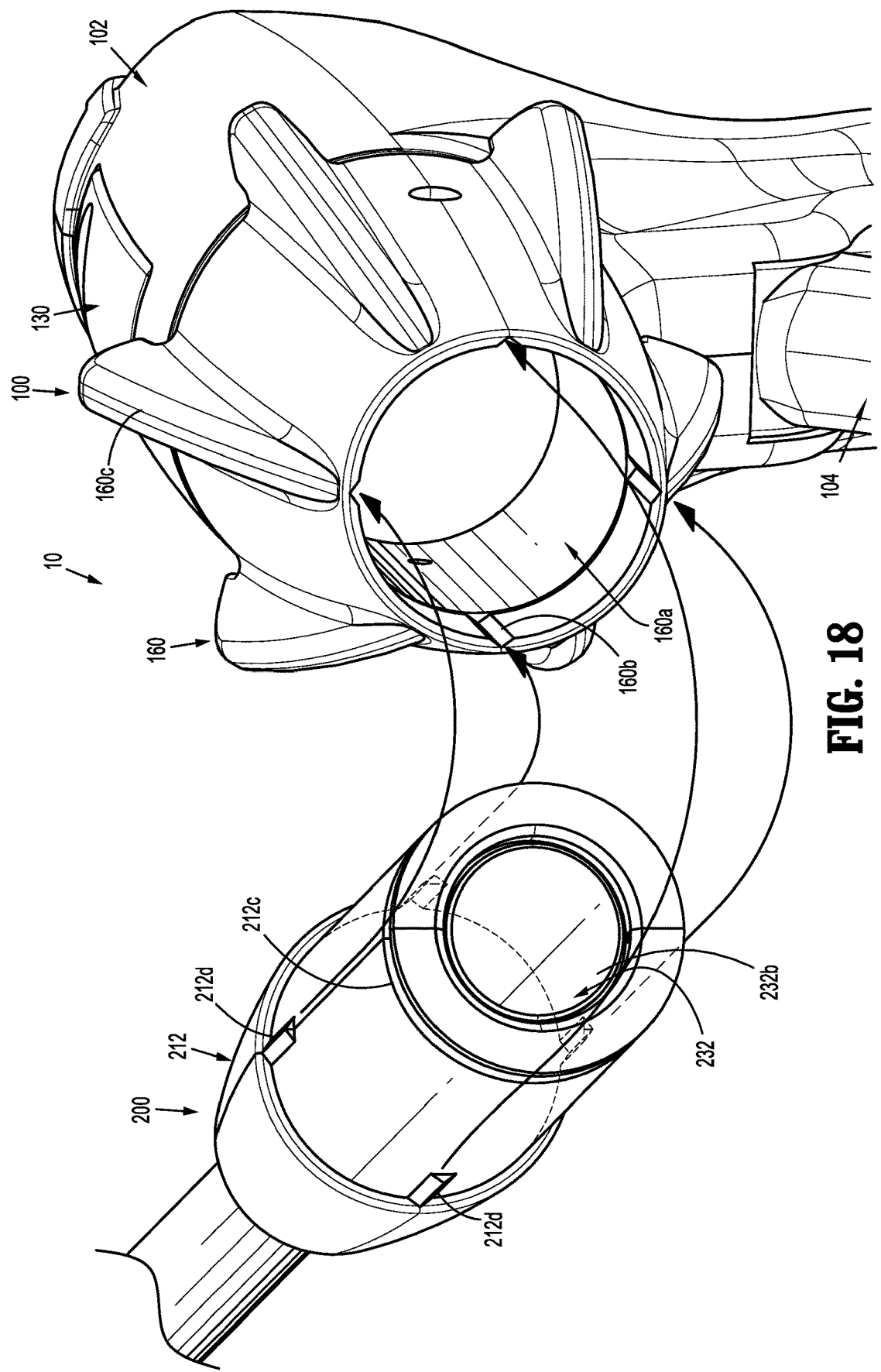
FIG. 18 is a perspective view illustrating an initial connection of the handle assembly and the first endoscopic assembly.
Figures 19, 20:
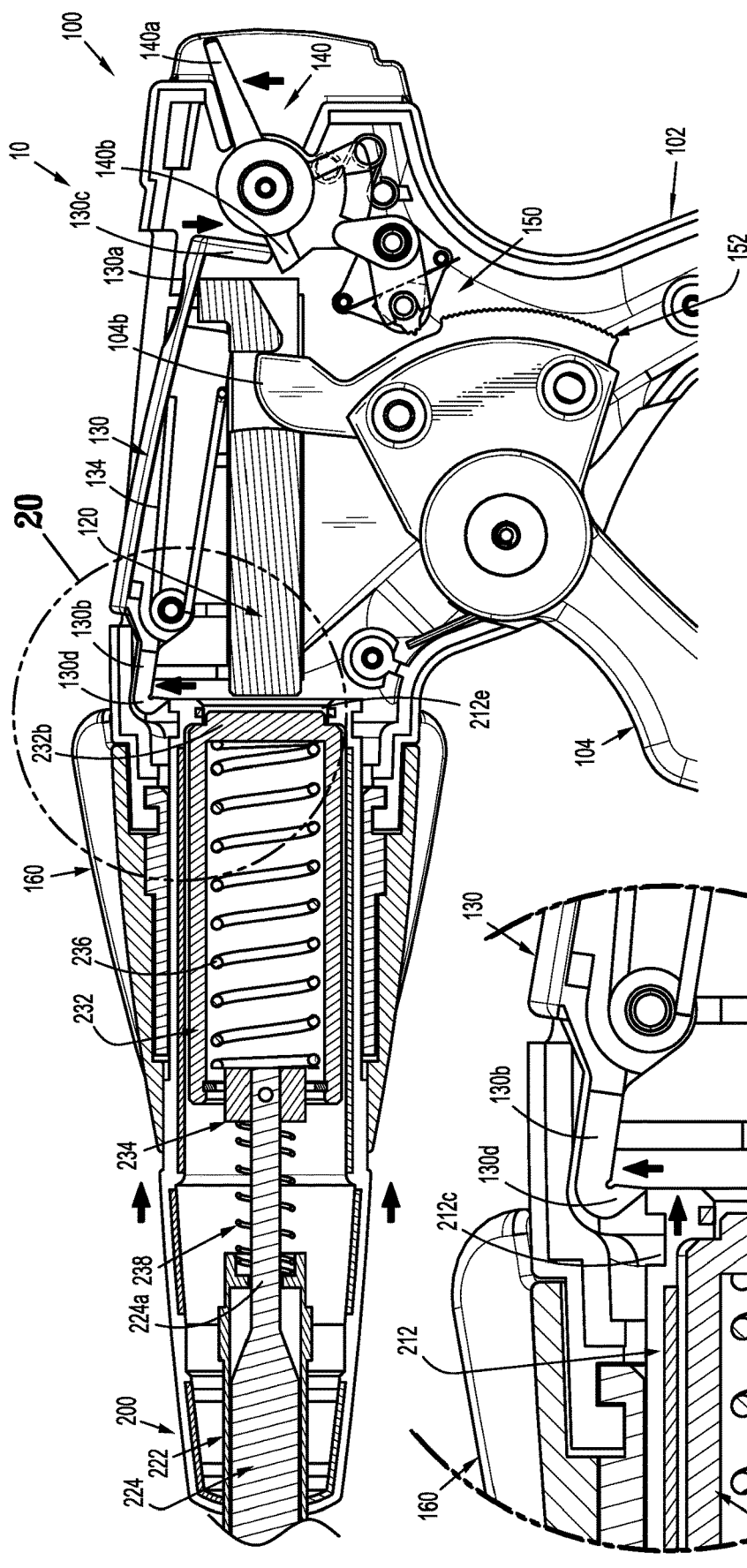
FIG. 19 is a longitudinal, transverse cross-sectional view illustrating the initial connection of the handle assembly and the first endoscopic assembly.
FIG. 20 is an enlarged view of the indicated area of detail of FIG. 19.
Figure 21:
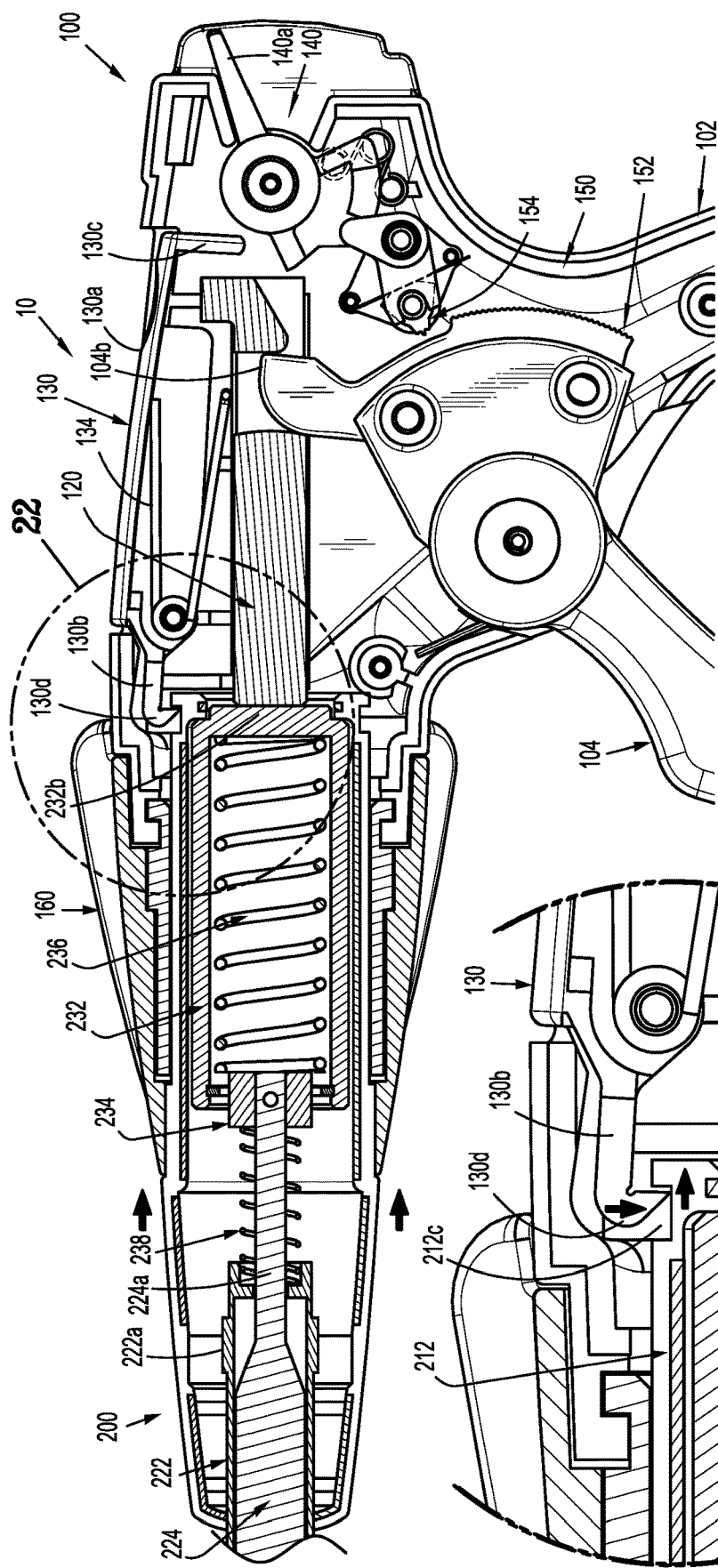
FIG. 21 is a longitudinal, transverse cross-sectional view illustrating a complete connection of the handle assembly and the first endoscopic assembly.
Figure 22:
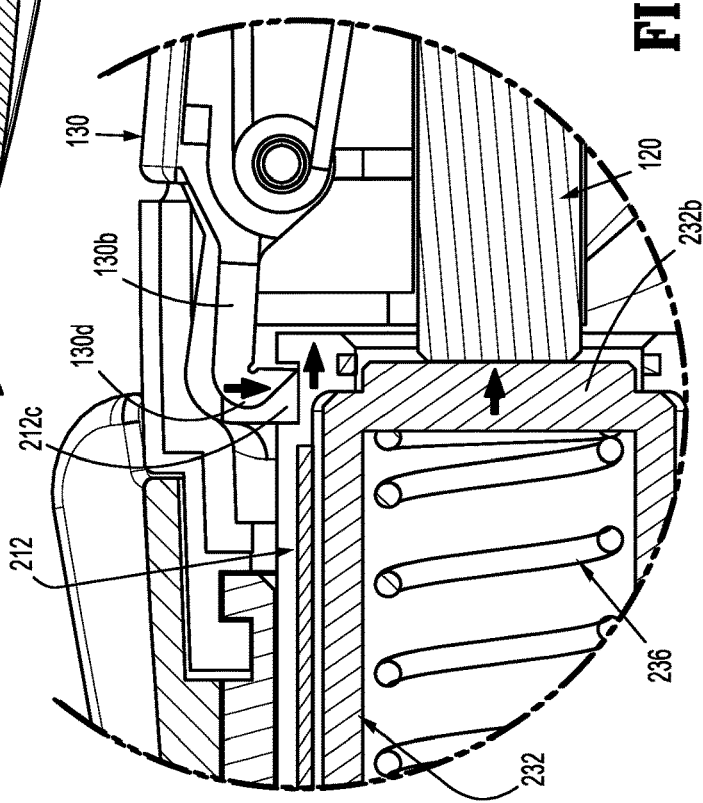
FIG. 22 is an enlarged view of the indicated area of detail of FIG. 21.
Figure 25:
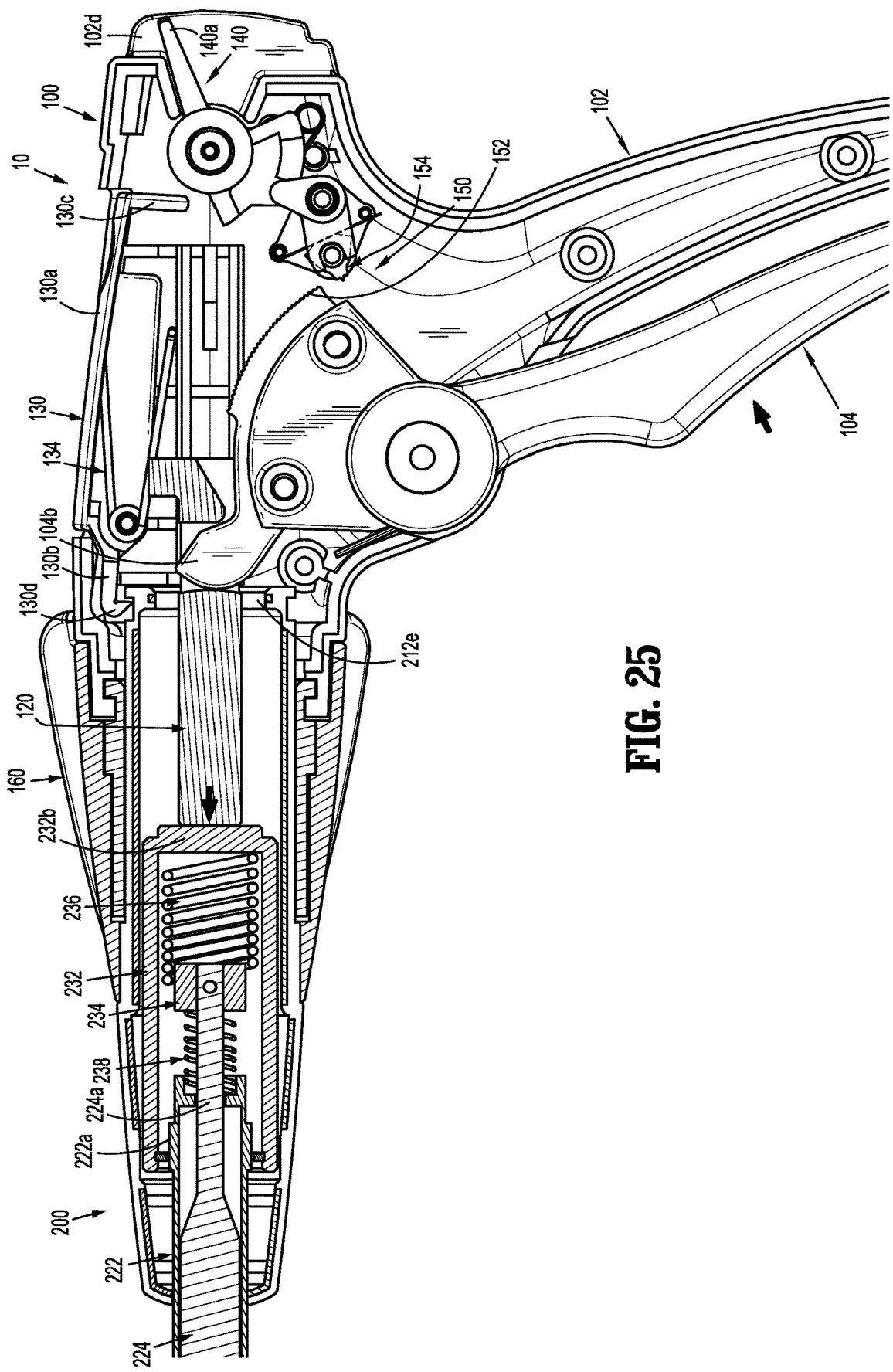
FIG. 25 is a longitudinal, transverse cross-sectional view illustrating a complete actuation of the handle assembly with the first endoscopic assembly connected thereto.
Figure 26:
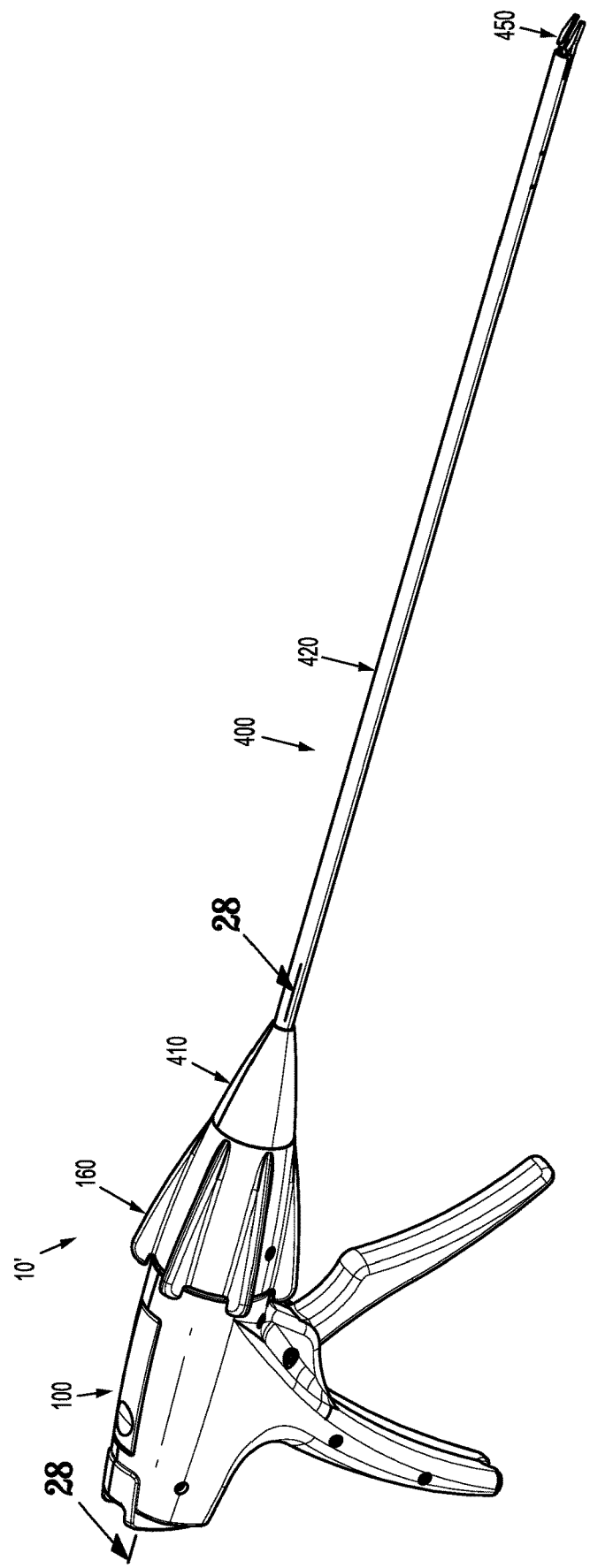
FIG. 26 is perspective view of the reposable endoscopic surgical clip applier including the reusable handle assembly and the second endoscopic assembly connected thereto.

With reference to FIGS. 15 and 17, hub assembly 210 includes a drive assembly 230 supported within outer housing 212 thereof. Drive assembly 230 includes a cartridge cylinder 232 having a cup-like configuration, wherein cartridge cylinder 232 includes an annular wall 232a, a proximal wall 232b supported at and closing off a proximal end of annular wall 232a, an open distal end 232c, and a cavity or bore 232d defined therewithin.

Drive assembly 230 also includes a cartridge plunger 234 slidably supported within bore 232d of cartridge cylinder 232. Cartridge plunger 234 is fixedly supported on inner shaft 224, at the proximal end 224a thereof. Cartridge plunger 234 is sized and configured for slidable receipt within bore 232d of cartridge cylinder 232 of drive assembly 230. A ring, flange or the like 235 may be fixedly supported at a distal end of bore 232d of cartridge cylinder 232, through which proximal end 224a of cartridge plunger 234 extends and which functions to maintain cartridge plunger 234 within bore 232d of cartridge cylinder 232.

Drive assembly 230 includes a first biasing member 236 (e.g., a compression spring) disposed within bore 232d of cartridge cylinder 232. Specifically, first biasing member 236 is interposed between proximal wall 232b of cartridge cylinder 232 and a proximal surface of cartridge plunger 234. First biasing member 236 has a first spring constant "K1" which is relatively more firm or more stiff, as compared to a second spring constant "K2" of a second biasing member 238, as is described in detail below.

Drive assembly 230 further includes a second biasing member 238 (e.g., a compression spring) supported on proximal end 224a of inner shaft 224. Specifically, second biasing member 238 is interposed between a proximal flange 222d of outer tube 222 and a distal surface of cartridge plunger 234. Second biasing member 238 has a second spring constant "K2" which is relatively less firm or less stiff, as compared to the first spring constant "K1" of first biasing member 236.

As illustrated in FIGS. 15 and 17, endoscopic assembly 200 includes a pair of jaws 250 pivotally supported in a clevis 222d at distal end 222b of outer tube 222 by a pivot pin 256. The pair of jaws 250 includes a first jaw 252 and a second jaw 254. Each jaw 252, 254 includes a respective proximal end 252a, 254a, and a respective distal end 252b, 254b, wherein proximal ends 252a, 254a and distal ends 252b, 254b of jaws 252, 254 are pivotable about pivot pin 256. Each proximal end 252a, 254a of respective jaws 252, 254 defines a cam slot 252c, 254c therein which is sized and configured to receive cam pin 224*d* of inner shaft 224. In use, as inner shaft 224 is axially displaced relative to outer shaft 222, inner shaft 224 translated cam pin 224*d* thereof through cam slot 252*c*, 254*c* of jaws 252, 254 to thereby open or close the pair of jaws 250.

When the pair of jaws 250 are in an open position, and a new, unformed or open surgical clip (not shown) is located or loaded within the distal ends 252*b*, 254*b* of jaws 252, 254 of the pair of jaws 250, as inner shaft 224 is moved distally relative to outer shaft 222, cam pin 224*d* is translated through cam slots 252*c*, 254*c* of jaws 252, 254. As cam pin 224*d* is translated through cam slots 252*c*, 254*c* of jaws 252, 254 the distal ends 252*b*, 254*b* of jaws 252, 254 are moved to the closed or approximated position to close and/or form the surgical clip located or loaded therewithin.

The dimensions of jaws 252, 254 and of cam slots 252*c*, 254*c* of jaws 252, 254 determines an overall length required to move jaws 252, 254 from a fully open position to a fully closed position, defining a closure stroke length of the pair of jaws 250.

With reference now to FIGS. 19-25, an operation or firing of surgical clip applier 10, including endoscopic assembly 200 operatively connected to handle assembly 100, is shown and described. With endoscopic assembly 200 operatively connected to handle assembly 100, and with a new, unformed or open surgical clip (not shown) is located or loaded within the distal ends 252*b*, 254*b* of jaws 252, 254 of the pair of jaws 250, as trigger 104 of handle assembly 100 is actuated drive bar 104*b* of trigger 104 acts on drive plunger 120 to distally advance drive plunger 120. As trigger 104 is actuated, pawl 154 of ratchet assembly 150 begins to engage rack 152 thereof. With pawl 154 engaged with rack 152, trigger 104 may not return to a fully unactuated position until trigger 104 completes a full actuation or stroke thereof.

As drive plunger 120 is distally advanced, a distal end of drive plunger 120 presses against proximal wall 232*b* of cartridge cylinder 232 of drive assembly 230 of endoscopic assembly 200 to distally advance cartridge cylinder 232. Due to first spring constant "K1" of first biasing member 236 being larger or greater than second spring constant "K2" of second biasing member 238, as cartridge cylinder 232 is advanced distally, cartridge cylinder 232 distally advances first biasing member 236, which in turn acts on cartridge plunger 234 to distally advance cartridge plunger 234. As cartridge plunger 234 is distally advanced, cartridge plunger 234 distally advances inner shaft 224 relative to outer shaft 222. Being that second biasing member 238 is interposed between proximal flange 222*d* of outer tube 222 and distal surface of cartridge plunger 234, as cartridge plunger 234 is distally advanced, cartridge plunger 234 also compresses second biasing member 238.

As inner shaft 224 is distally advanced relative to outer shaft 222, inner shaft 224 distally advances cam pin 224*d* through cam slot 252*c*, 254*c* of jaws 252, 254 to close the pair of jaws 250 and to close and/or form the surgical clip (not shown) loaded within the pair of jaws 250. Cam pin 224*d* of inner shaft 224 is advanced distally until cam pin 224*d* reaches an end of cam slots 252*c*, 254*c* of jaws 252, 254 of the pair of jaws 250 and/or until the distal ends 252*b*, 254*b* of jaws 252, 254 of the pair of jaws 250 are fully approximated against one another (e.g., in contact with one another or fully closed on the surgical clip (not shown)), whereby cam pin 224*d* may not have reached the end of cam slots 252*c*, 254*c* of jaws 252, 254. This position may be considered a hard stop of the pair of jaws 250. The axial distance that cam pin 224*d* has traveled from a proximal-most position thereof to when cam pin 224*d* reaches the end of cam slots 252*c*, 254*c* of jaws 252, 254 or when the distal ends 252*b*, 254*b* of jaws 252, 254 of the pair of jaws 250 are fully approximated against one another, may also define the closure stroke length of the pair of jaw 250.

When the pair of jaws 250 have reached the hard stop, or when the cam pin 224*d* has reached an end of the closure stroke length, pawl 154 of ratchet assembly 150 of handle assembly 100 may not have cleared rack 152 thereof, and thus blocks or prevents trigger 104 from returning to a fully unactuated position thereof. Since the pair of jaws 250 cannot close any further, and since cam pin 224*d* cannot be advanced distally any further, inner shaft 222 is also stopped from further distal advancement. However, as mentioned above, in order to return trigger 104 to the fully unactuated position, trigger 104 must first complete the full actuation stroke thereof. As such, as trigger 104 is further actuated to complete the full stroke thereof, as drive plunger 120 is continued to be driven distally, the distal end of drive plunger 120 continues to press against proximal wall 232*b* of cartridge cylinder 232 of drive assembly 230 of endoscopic assembly 200 to continue to distally advance cartridge cylinder 232.

With inner shaft 222, and in turn cartridge plunger 234, stopped from any further distal advancement, as cartridge cylinder 232 is continued to be advanced distally, cartridge cylinder 232 begins to and continues to compress first biasing member 236 until such time that pawl 154 of ratchet assembly 150 of handle assembly 100 clears and disengages rack 152 thereof. With pawl 154 of ratchet assembly 150 clear and disengaged from rack 152, trigger 104 may be released and returned to the fully unactuated position by hand, by a return spring 104*a* of trigger 104 and/or by first biasing member 236 and second biasing member 238 of endoscopic assembly 200.

In accordance with the present disclosure, the trigger stroke length for trigger 104 of handle assembly 100 is constant or fixed, while the closure stroke length of the pair of jaws 250 may vary depending on the particular endoscopic assembly 200 connected to handle assembly 100. For example, particular endoscopic assemblies 200 may require the pair of jaws 250 thereof to travel a relatively greater or smaller distance in order to complete a full opening and closing thereof. As such, various sized and dimensioned endoscopic assemblies, including a hub assembly in accordance with the present disclosure, substantially similar to hub assembly 210, may be connected to the universal handle assembly 100 and be actuatable by the universal handle assembly 100.

Accordingly, various endoscopic assemblies, constructed in accordance with the principles of the present disclosure, may be provided which are also capable of firing or forming or closing surgical clips of various sizes, materials, and configurations, across multiple platforms for multiple different manufactures.

Turning now to FIGS. 26-29, an endoscopic surgical clip applier, in accordance with the present disclosure, and assembly in another configuration, is generally designated as 10'. Surgical clip applier 10' generally includes reusable handle assembly 100, at least one disposable or reusable endoscopic assembly 400 selectively connectable to and extendable distally from handle assembly 100; and optionally at least one disposable surgical clip cartridge assembly (not shown) selectively loadable into a shaft assembly of a respective endoscopic assembly 400.

Turning now to FIGS. 1, 2, 16 and 17, an embodiment of an endoscopic assembly 400, of surgical clip applier 10', is shown and described. Endoscopic assembly 400 includes a hub assembly 410, a shaft assembly 420 extending from hub assembly 410, and a pair of jaws 450 pivotally connected to a distal end of shaft assembly 420. It is contemplated that endoscopic assembly 400 may be configured to close, fire or form surgical clips similar to those shown and described in U.S. Pat. No. 7,819,886 or 7,905,890, the entire contents of each of which is incorporated herein by reference.

Hub assembly 410 also functions as an adapter assembly which is configured for selective connection to rotation knob 160 and nose 102c of housing 102 of handle assembly 100. Hub assembly 410 includes an outer housing 412 having a cylindrical outer profile. Outer housing 412 includes a first or right side half section 412a, and a second or left side half section 412b. Outer housing 412 of hub assembly 410 defines an outer annular channel 412c formed in an outer surface thereof, and at least one (or an annular array) of axially extending ribs 412d projecting from an outer surface thereof. Outer annular channel 412c of outer housing 412 of endoscopic assembly 400 is configured to receive catch 130d of release lever 130 of handle assembly 100 (FIGS. 28 and 29) when endoscopic assembly 400 is coupled to handle assembly 100.

Ribs 412d of outer housing 412 function as a clocking/alignment feature during connection of endoscopic assembly 400 and handle assembly 100 with one another, wherein ribs 412d of outer housing 412 of endoscopic assembly 400 are radially and axially aligned with respective grooves 160b of rotation knob 160 (FIG. 18) of handle assembly 100. During connection of endoscopic assembly 400 and handle assembly 100, ribs 412d of outer housing 412 of endoscopic assembly 400 are slidably received in respective grooves 160b of rotation knob 160 of handle assembly 100.

The connection of hub assembly 410 of endoscopic assembly 400 with rotation knob 160 of handle assembly 100 enables endoscopic assembly 400 to rotate 360°, about a longitudinal axis thereof, relative to handle assembly 100.

Outer housing 412 of hub assembly 410 further defines an open proximal end 412e configured to slidably receive a distal end of drive plunger 120 of handle assembly 100, when endoscopic assembly 400 is coupled to handle assembly 100 and/or when surgical clip applier 10' is fired.

As mentioned above, endoscopic assembly 400 includes a shaft assembly 420 extending distally from hub assembly 410. Shaft assembly 420 includes an elongate outer tube 422 having a proximal end 422a supported and secured to outer housing 412 of hub assembly 410, a distal end 422b projecting from outer housing 412 of hub assembly 410, and a lumen 422c (FIG. 27) extending longitudinally therethrough. Distal end 422b of outer tube 422 supports a pair of jaws 450.

Shaft assembly 420 further includes an inner shaft 424 slidably supported within lumen 422c of outer tube 422. Inner shaft 424 includes a proximal end 424a projecting proximally from proximal end 422a of outer tube 422, and a distal end 424b configured to actuate the pair of jaws 450 to form a surgical clip (not shown) that has been loaded into the pair of jaws 450. Proximal end 424a, as illustrated in FIGS. 28 and 29, may define a hook 424c or other translational force coupling feature.

Figure 27:
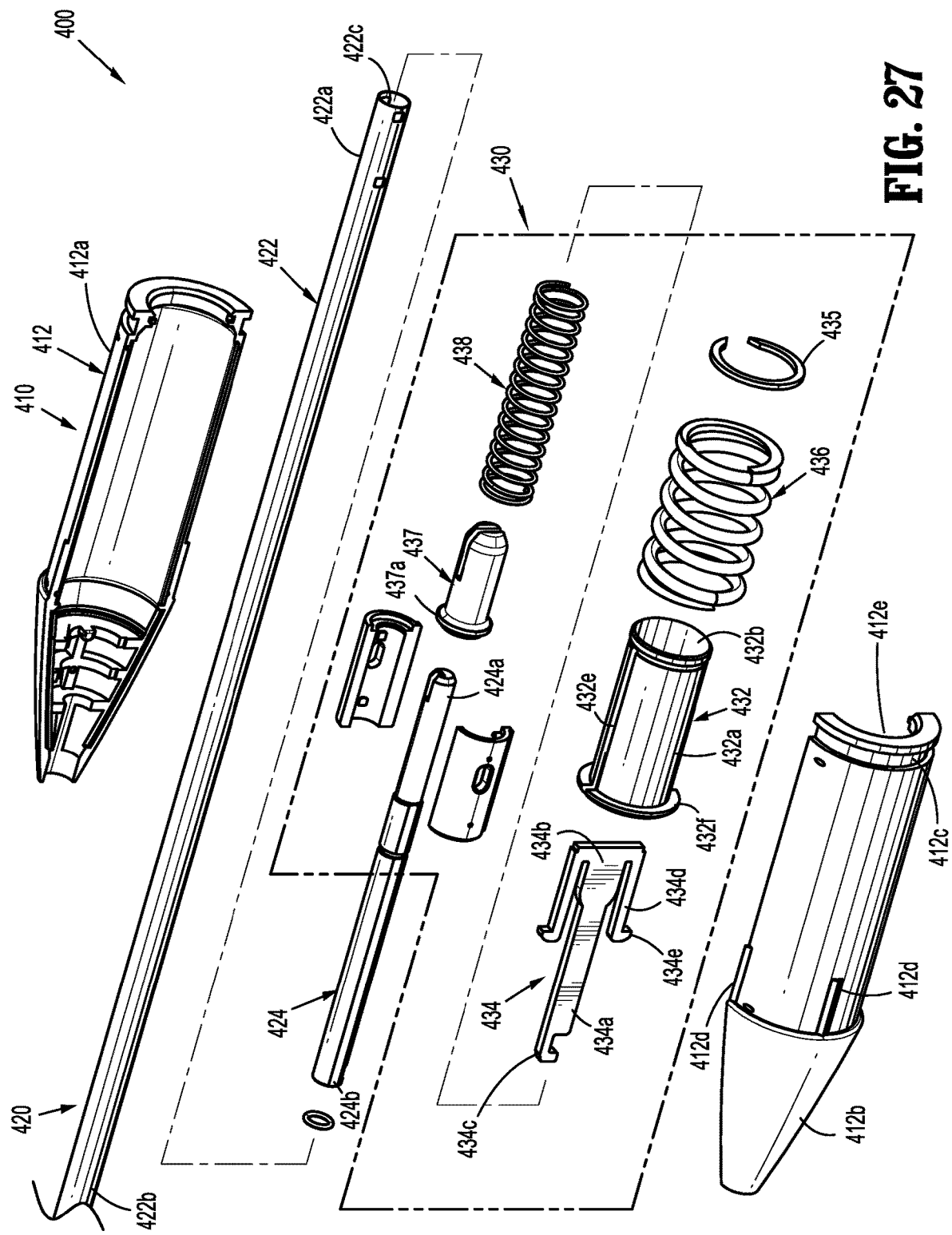
FIG. 27 is a perspective view, with parts separated, of the second endoscopic assembly of FIGS. 1 and 26.
Figure 28:
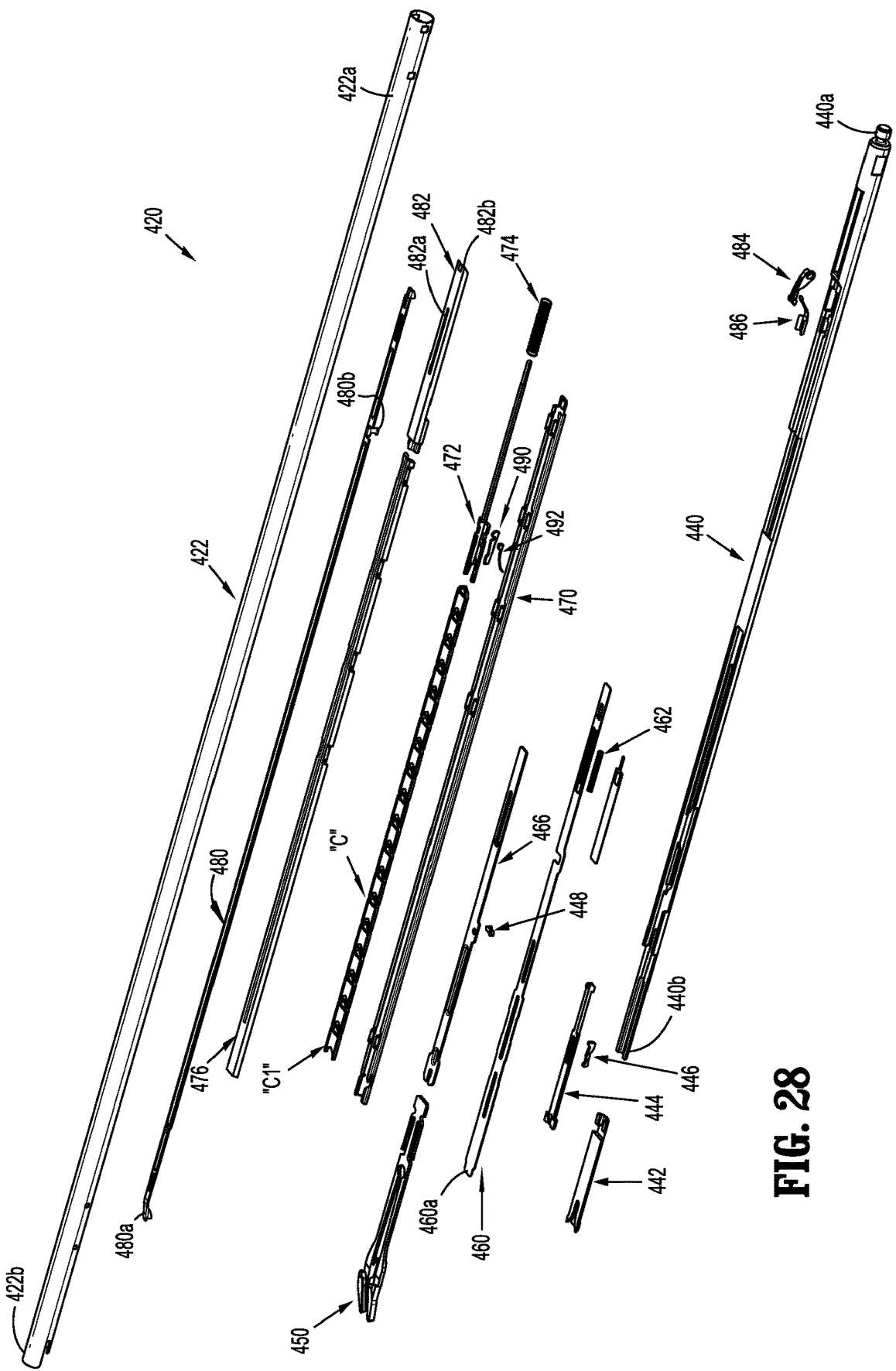
FIG. 28 is a perspective view, with parts separated, of a shaft assembly of the second endoscopic assembly.
Figure 40:
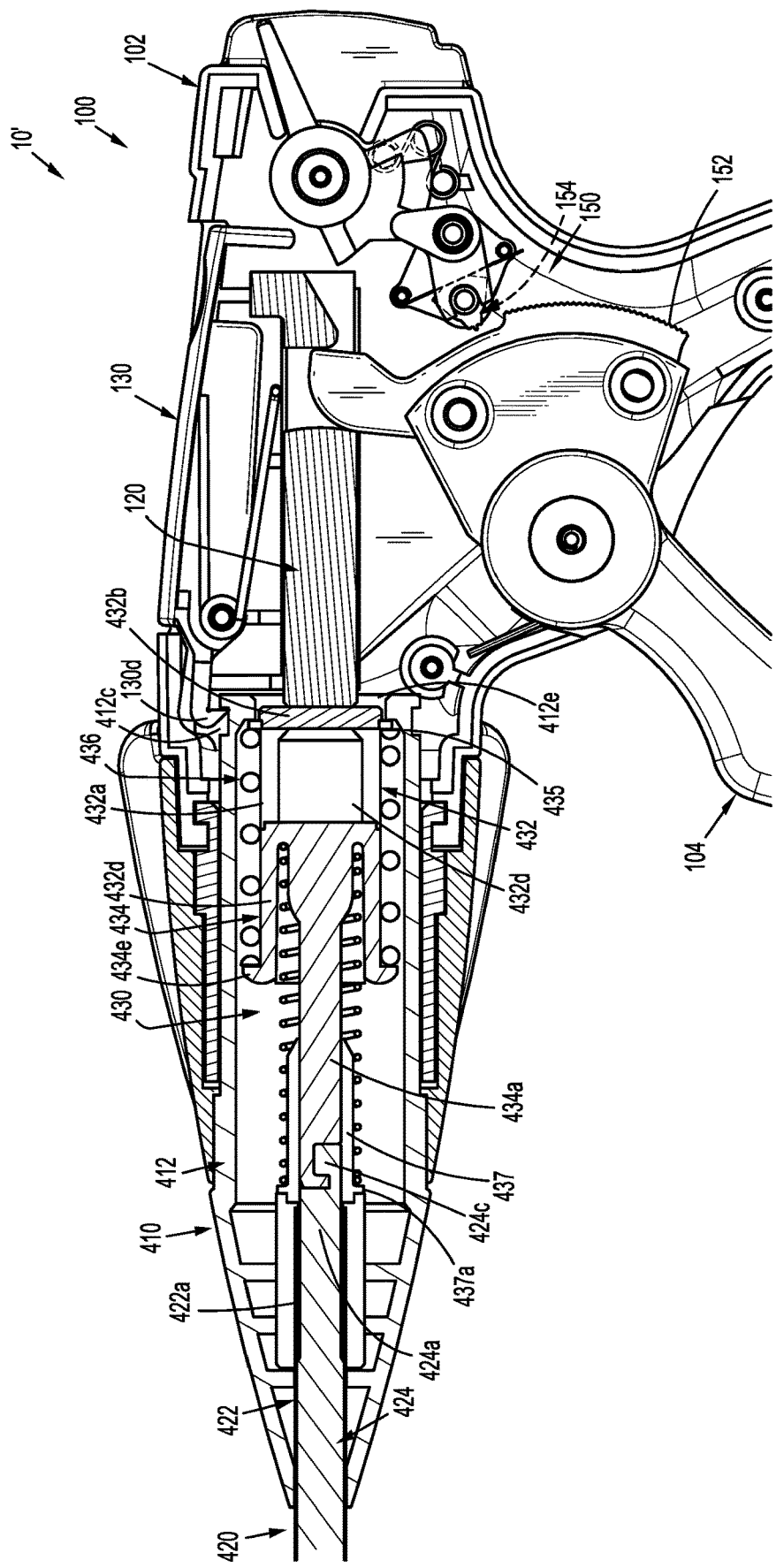
FIG. 40 is a longitudinal, transverse cross-sectional view illustrating a complete connection of the handle assembly and the second endoscopic assembly, prior to actuation of a trigger of the handle assembly.
Figure 41:
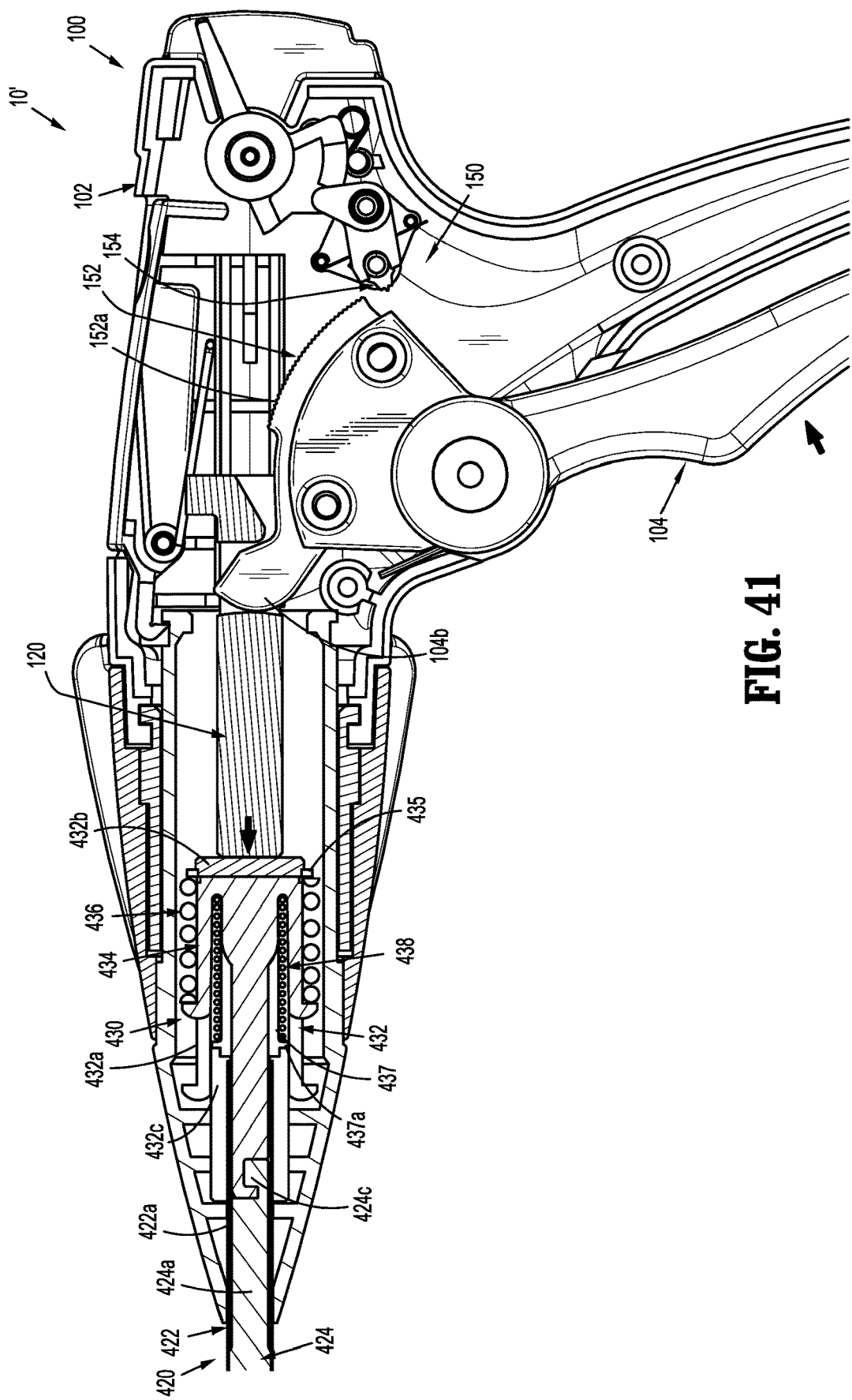
FIG. 41 is a longitudinal, transverse cross-sectional view illustrating a complete actuation of the handle assembly with the second endoscopic assembly connected thereto.

With reference to FIGS. 27-29, hub assembly 410 includes a drive assembly 430 supported within outer housing 412 thereof. Drive assembly 430 includes a cartridge cylinder 432 having a cup-like configuration, wherein cartridge cylinder 432 includes a longitudinally split annular wall 432a, a proximal wall 432b supported at and closing off a proximal end of annular wall 432a, an open distal end 432c, a cavity or bore 432d defined therewithin, and a pair of axially extending slits 432e. Cartridge cylinder 432 includes an annular flange 432f provided at distal end 432c thereof. A ring, flange or the like 435 may be fixedly supported at a proximal end of cartridge cylinder 432.

Drive assembly 430 also includes a cartridge plunger or key 434 slidably supported within bore 432d and within slits 432e of cartridge cylinder 432. Cartridge plunger 434 is selectively connectable to proximal end 424a of inner shaft 424. Cartridge plunger 434 is sized and configured for slidable receipt within slits 432e and bore 432d of cartridge cylinder 432 of drive assembly 430. Cartridge plunger 434 includes an elongate stem or body portion 434a having a proximal end 434b, and a distal end 434c, wherein distal end 434c of cartridge plunger 434 is configured for selective connection to proximal end 424a of inner shaft 424. Cartridge plunger 434 further includes a pair of opposed arms 434d supported at the proximal end 434b thereof and which extend in a distal direction along stem 434a and towards distal end 434c. Each arm 434d terminates in a radially extending finger 434e, wherein fingers 434e project from cartridge cylinder 432 when cartridge plunger 434 is disposed within cartridge cylinder 432.

Drive assembly 430 may also include a collar 437 defining a lumen therethrough and through with inner shaft 424 and stem 434a of cartridge plunger 434 extend. Collar 437 includes an outer annular flange 437a extending therefrom.

Drive assembly 430 includes a first biasing member 436 (e.g., a compression spring) disposed about cartridge cylinder 432. Specifically, first biasing member 436 is interposed between ring 435 supported on cartridge cylinder 432 and fingers 434e of cartridge plunger 434. First biasing member 436 has a first spring constant "K1" which is relatively more firm or more stiff, as compared to a second spring constant "K2" of a second biasing member 438, as is described in detail below.

Drive assembly 430 further includes a second biasing member 438 (e.g., a compression spring) supported on stem 434a of cartridge plunger 434 and on collar 437. Specifically, second biasing member 438 is interposed between a flange 437a of collar 437 and proximal end 434b of cartridge plunger 434. Second biasing member 438 has a second spring constant "K2" which is relatively less firm or less stiff, as compared to the first spring constant "K1" of first biasing member 436.

Turning now to FIGS. 26-41, shaft assembly 420 of endoscopic assembly 400 includes at least a spindle 440 slidably supported in lumen 422c of outer tube 422, a wedge plate 460 slidably supported within lumen 422c of outer tube 422 and interposed between the pair of jaws 450 and spindle 440; a clip channel 470 fixedly supported in lumen 422c of outer tube 422 and disposed adjacent the pair of jaws 450 (supported in and extending from distal end 422b of outer tube 422) on a side opposite wedge plate 460, and a pusher bar 480 slidably supported in lumen 422c of outer tube 422 and being disposed adjacent clip channel 470.

Spindle 440 includes a proximal end 440 defining an engagement feature (e.g., a nub or enlarged head) configured to engage a complementary engagement feature provided in distal end 424b of inner shaft 424. Spindle 440 further includes a distal end 440b operatively connected to a jaw cam closure wedge 442 via a slider joint 444. Jaw cam closure wedge 442 is selectively actuatable by spindle 440 to engage camming features of the pair of jaws 450 to close the pair of jaws 450 and form a surgical clip "C" loaded therewithin.

Slider joint 444 supports a latch member 446 for selective engagement with spindle 440. Latch member 446 may be cammed in a direction toward spindle 440, wherein latch member 446 extends into a corresponding slot formed in spindle 440 during actuation or translation of spindle 440. In operation, during distal actuation spindle 400, at a predetermined distance, latch member 446 is mechanically forced or cammed into and engage a channel of spindle 440. This engagement of latch member 446 in the channel of spindle 440 allows slider joint 444 to move together with jaw cam closure wedge 442. Jaw cam closure wedge 442 thus can engage the relevant surfaces of the pair of jaws 450 to close the pair of jaws 450.

As illustrated in FIGS. 28 and 39, slider joint 444 is connected, at a proximal end 444a thereof, to a channel formed in spindle 440. A distal end 444b of slider joint 444 defines a substantially T-shaped profile, wherein the distal end 444b thereof is connected to jaw cam closure wedge 442. Latch member 446 functions as a linkage and is disposed to move through an aperture 444c in slider joint 444 to link with another fixed member and prevent slider joint 444 from advancing jaw cam closure wedge 442, and thus preventing the camming of jaw cam closure wedge 442 from camming the pair of jaws 450 to a closed condition during an initial stroke of trigger 104.

Spindle 440 is provided with a camming feature configured to move a cam link 448 (pivotably connected to a filler component 466, as will be described in greater detail below) a perpendicular manner relatively to a longitudinal axis of spindle 440 during a distal advancement of spindle 440.

Clip channel 470 of shaft assembly 420 slidably retains a stack of surgical clips "C" therein for application, in seriatim, to the desired tissue or vessel. A clip follower 472 is provided and slidably disposed within clip channel 470 at a location proximal of the stack of surgical clips "C". A biasing member 474 is provided to spring bias clip follower 472, and in turn, the stack of surgical clips "C", distally. A clip channel cover 476 is provided that overlies clip channel 470 to retain and guide clip follower 472, biasing member 474 and the stack of surgical clips "C" in clip channel 470.

As mentioned above, shaft assembly 420 includes a pusher bar 480 for loading a distal-most surgical clip "C1" of the stack of surgical clips "C" into the pair of jaws 450. Pusher bar 480 includes a pusher 480a at a distal end thereof for engaging a backspan of the distal-most surgical clip "C1" and urging the distal-most surgical clip "C1" into the pair of jaws 450. Pusher bar 480 includes a fin or tab 480b extending therefrom and extending into a slot 482a of a trip block 482. Fin 480b of pusher bar 480 is acted upon by a biasing member (not shown) that is supported in trip block 482 to bias pusher bar 480 in a proximal direction.

In operation, in order for spindle 440 to advance pusher bar 480 during a distal movement thereof, spindle 440 supports a trip lever 484 and a biasing member 486 (e.g., leaf spring). During a distal movement of spindle 440, as illustrated in FIG. 31, a distal nose or tip 484a of trip lever 484 selectively engages pusher bar 480 to distally advance pusher bar 480 and load distal-most surgical clip "C1" into the pair of jaws 450.

Also as mentioned above, shaft assembly 420 further includes a wedge plate 460 that is biased to a proximal position by a wedge plate spring 462. Wedge plate 460 is a flat bar shaped member having a number of windows formed therein. Wedge plate 460 has a distal-most position wherein a tip or nose of wedge plate 460 is inserted between the pair of jaws 450 to maintain the pair of jaws 450 in an open condition for loading of the distal-most surgical clip "C1" therein. Wedge plate 460 has a proximal-most position, maintained by wedge plate spring 462, wherein the tip or nose of wedge plate 460 is retracted from between the pair of jaws 450.

As illustrated in FIGS. 28 and 38, wedge plate 460 defines a "U" or "C" shaped aperture or window 460b in a side edge thereof. The "C" shaped aperture or window 460b of wedge plate 460 selectively engages a cam link 448 supported on a filler plate 466. Cam link 448 selectively engages a surface of "C" shaped aperture or window 460b of wedge plate 460 to retain wedge plate 460 in a distal-most position such that a distal tip or nose 460a of wedge plate 460 is maintained inserted between the pair of jaws 450 to maintain the pair of jaws 450 splayed apart.

Shaft assembly 420 further includes a filler component 466 interposed between clip channel 470 and wedge plate 460, at a location proximal of the pair of jaws 450. Filler component 466 pivotably supports a cam link 448 that is engagable with wedge plate 460. In operation, during a distal advancement of spindle 440, a camming feature of spindle 440 engages a cam link boss of cam link 448 to thereby move cam link 448 out of engagement of wedge plate 460 and permit wedge plate 460 to return to the proximal-most position as a result of biasing member 462.

Trip block 482 defines an angled proximal surface 482b for engagement with a corresponding surface of trip lever 484 that will be discussed herein. As mentioned above, notch or slot 482a of trip block 482 is for receipt of fin 480b of pusher bar 480. In order to disengage trip lever 484 from a window 480c (FIG. 31) of pusher bar 480, and allow pusher bar 480 to return to a proximal-most position following loading of a surgical clip "C" into the pair of jaws 450, angled proximal surface 482b trip block 482 engages trip lever 484 to cam trip lever 484 out of window 480c of pusher bar 480. It is contemplated that spindle 440 may define a first cavity and a second cavity therein for receiving trip lever 484 and trip lever biasing spring 486, respectively. The first cavity may be provided with a pivoting boss to allow trip lever 484 to pivot between a first position and a second position. Trip lever biasing spring 486 may rest in the second cavity.

Trip lever biasing spring 486 functions to maintain a tip of trip lever 484 in contact with pusher bar 480, and more specifically, within window 480c of pusher bar 480 (FIG. 31) such that distal advancement of spindle 440 results in distal advancement of pusher bar 480, which in turn results in a loading of a distal-most surgical clip "C1" in the pair of jaws 450.

With reference to FIGS. 28, 33 and 36, clip applier 10' also has a lockout bar 490. Lockout bar 490 includes a first end, and a second opposite hook end. The second hook end of lockout bar 490 is adapted to engage clip follower 472 of shaft assembly 420. Lockout bar 490 is pivotally retained in a slot formed in clip follower 472. Lockout bar 490 does not by itself lockout clip applier 10', but instead cooperates with the ratchet mechanism 150 of handle assembly 100 to lock out clip applier 10'.

Lockout bar 490 is adapted to move distally with clip follower 472 each time clip applier 10' is fired, and clip follower 472 is advanced distally. In operation, each time a surgical clip "C" is fired from clip applier 10', clip follower 472 will advance distally relative to the clip channel 470.

Pusher bar 480 defines a distal window therein (not shown). In operation, when clip follower 472 is positioned beneath pusher bar 480 (e.g., when there are no remaining surgical clips), a distal end 490a of lockout bar 490 will deflect upward (due to a biasing of a lockout biasing member 492), and enter a distal window 480d of pusher bar 480 to engage pusher bar 480 at a distal end of distal window 480d. Further, a proximal end 490b of lockout bar 490, defines a hook (FIG. 37), which is rotated into and engages an aperture defined in a floor of clip channel 470.

With the distal end of pusher bar 480 disposed within distal window 480d of pusher bar 480, pusher bar 480, and in turn, spindle 440 cannot return to a fully proximal position. Since spindle 440 cannot return to the fully proximal position, pawl 152 of ratchet mechanism 150 of handle assembly 100 cannot return to the home or initial position relative to rack 154 thereof. Instead, pawl 154 will remain in an intermediate position along rack 154, thus preventing trigger 104 from returning to a fully unactuated position.

With continued reference to FIGS. 26-29, an operation or firing of surgical clip applier 10', including endoscopic assembly 400 operatively connected to handle assembly 100, is shown and described. With endoscopic assembly 400 operatively connected to handle assembly 100, as trigger 104 of handle assembly 100 is actuated drive bar 104b of trigger 104 acts on drive plunger 120 to distally advance drive plunger 120. As trigger 104 is actuated, pawl 154 of ratchet assembly 150 begins to engage rack 152 thereof. With pawl 154 engaged with rack 152, trigger 104 may not return to a fully unactuated position until trigger 104 completes a full actuation or stroke thereof.

As drive plunger 120 is distally advanced, a distal end of drive plunger 120 presses against proximal wall 432b of cartridge cylinder 432 of drive assembly 430 of endoscopic assembly 400 to distally advance cartridge cylinder 432. Due to first spring constant "K1" of first biasing member 436 being larger or greater than second spring constant "K2" of second biasing member 438, as cartridge cylinder 432 is advanced distally, ring 435 acts on first biasing member 436 which in turn acts on fingers 434e of cartridge plunger 434 to push cartridge plunger 434 distally. As cartridge plunger 434 is distally advanced, cartridge plunger 434 distally advances inner shaft 424 relative to outer shaft 422. Being that second biasing member 438 is interposed between a flange 437a of collar 437 and proximal end 434b of cartridge plunger 434, as cartridge plunger 434 is distally advanced, cartridge plunger 434 also compresses second biasing member 438.

As inner shaft 424 is distally advanced relative to outer shaft 422, inner shaft 424 actuates a clip pusher (not shown) which in turn acts on a distal-most surgical clip (not shown) of a stack of surgical clips (not shown) to distally advance the distal-most surgical clip into the pair of jaws 450. Following loading of the distal-most surgical clip into the pair of jaws 450, the distal advancement of inner shaft 424 effects a closure of the pair of jaws 450 to form the surgical clip loaded therewithin.

When the pair of jaws 450 have fully closed to form the surgical clip loaded therein, or when the pair of jaws 450 have reached a hard stop, pawl 154 of ratchet assembly 150 of handle assembly 100 may not have cleared rack 152 thereof, and thus blocks or prevents trigger 104 from returning to a fully unactuated position thereof. Since the pair of jaws 450 cannot close any further, inner shaft 422 is also stopped from further distal advancement. However, as mentioned above, in order to return trigger 104 to the fully unactuated position, trigger 104 must first complete the full actuation stroke thereof. As such, as trigger 104 is further actuated to complete the full stroke thereof, as drive plunger 120 is continued to be driven distally, the distal end of drive plunger 120 continues to press against proximal wall 432b of cartridge cylinder 432 of drive assembly 430 of endoscopic assembly 400 to continue to distally advance cartridge cylinder 432.

With inner shaft 422, and in turn cartridge plunger 434, stopped from any further distal advancement, as cartridge cylinder 432 is continued to be advanced distally relative to cartridge plunger 434, cartridge cylinder 432 begins to and continues to compress first biasing member 436 until such time that pawl 154 of ratchet assembly 150 of handle assembly 100 clears and disengages rack 152 thereof. With pawl 154 of ratchet assembly 150 clear and disengaged from rack 152, trigger 104 may be released and returned to the fully unactuated position by hand, by a return spring (not shown) of trigger 104 or handle assembly 100 and/or by first biasing member 436 and second biasing member 438 of endoscopic assembly 400.

Referring to FIGS. 42-47, another embodiment of an endoscopic assembly is provided and generally identified by reference numeral 500. Endoscopic assembly 500 is similar to endoscopic assembly 400 and therefore for purposes of brevity, only the differences therebetween are described in detail hereinbelow.

The hub assembly 510 of the endoscopic assembly 500 is similar to the hub assembly 410 of the endoscopic assembly 400 except each of the right and left side half sections 512a, 512b of the outer housing 512 define an annular groove 512f at a medial portion thereof having a larger diameter than that of an open proximal end thereof. In this manner, the annular groove 512f of the outer housing 512 defines a distal facing surface 512g at a proximal portion thereof and a proximal facing surface 512h at a distal portion thereof.

Figure 45:
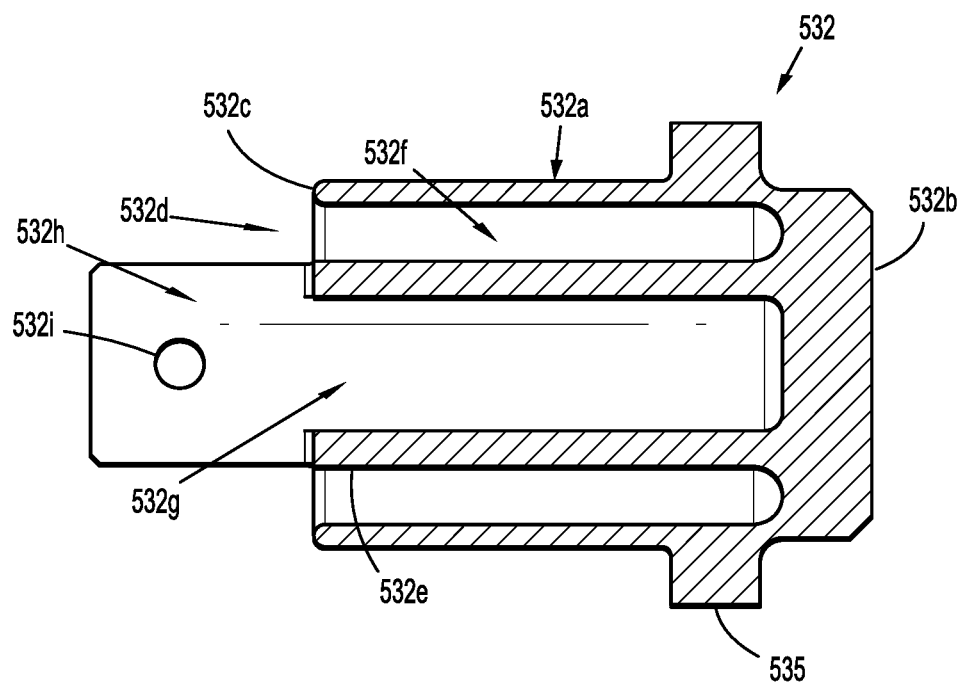
FIG. 45 is a side, longitudinal cross-sectional view of a cartridge cylinder of the hub assembly of FIG. 42.

The endoscopic assembly 500 includes a drive assembly 530 (FIG. 43) having a cartridge cylinder 532 slidably disposed within a cavity of the outer housing 512. The cartridge cylinder 532 includes an elongate body 532a defining a proximal end wall 532b and a distal end wall 532c (FIG. 45). The distal end wall 532c of the cartridge cylinder 532 defines a cavity or bore 532d therein. The cavity 532d of the cartridge cylinder 532 defines a longitudinally extending boss 532e that extends distally beyond the distal end wall 532c thereof. In this manner, an annular space 532f is defined between an inner surface of the cavity 532d and an outer surface of the longitudinally extending boss 532e of the cartridge cylinder 532. The annular space 532f of the cartridge cylinder 532 is configured to receive a second biasing element 540 of the endoscopic assembly 500 therein.

The longitudinally extending boss 532e of the cartridge cylinder 532 defines a longitudinal counterbore 532g therein that is configured to slidably receive a proximal portion of a plunger or key 534 of the endoscopic assembly 500. A distal portion of the longitudinally extending boss 532e defines a transverse slot 532h configured to permit the wings 534a of a plunger 534 of the endoscopic assembly 500 to be slidably received therein. A pair of transverse bores 532i is defined through a distal portion of the longitudinally extending boss 532e and is disposed in 180 degree relation to the transverse slot 532h thereof. The pair of bores 532i of the cartridge cylinder 532 is configured to fixedly receive a pin 536 to slidably retain the plunger 534 within the slot 532g.

A radially extending flange 535 is disposed on a proximal portion of the elongate body 532a of the cartridge cylinder 532 and is configured to be slidably received within the annular groove 512f of the outer housing 512.

Figure 42:
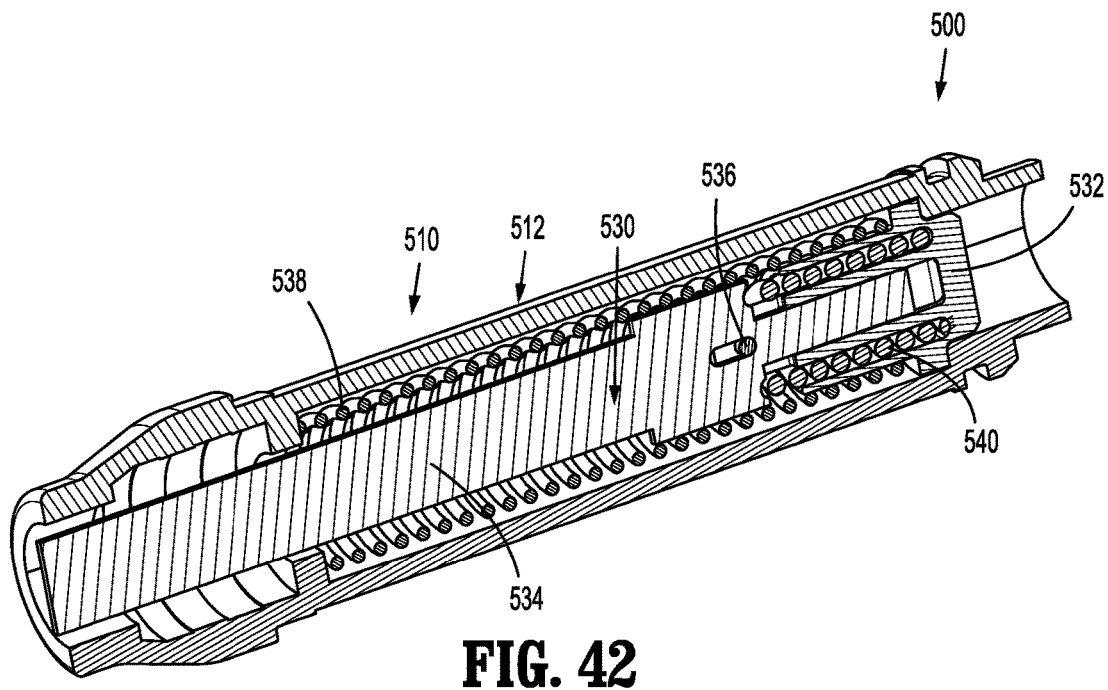
FIG. 42 is a perspective, longitudinal cross-sectional view of another embodiment of a hub assembly of an endoscopic assembly for use with a reposable surgical clip applier.
Figure 43:
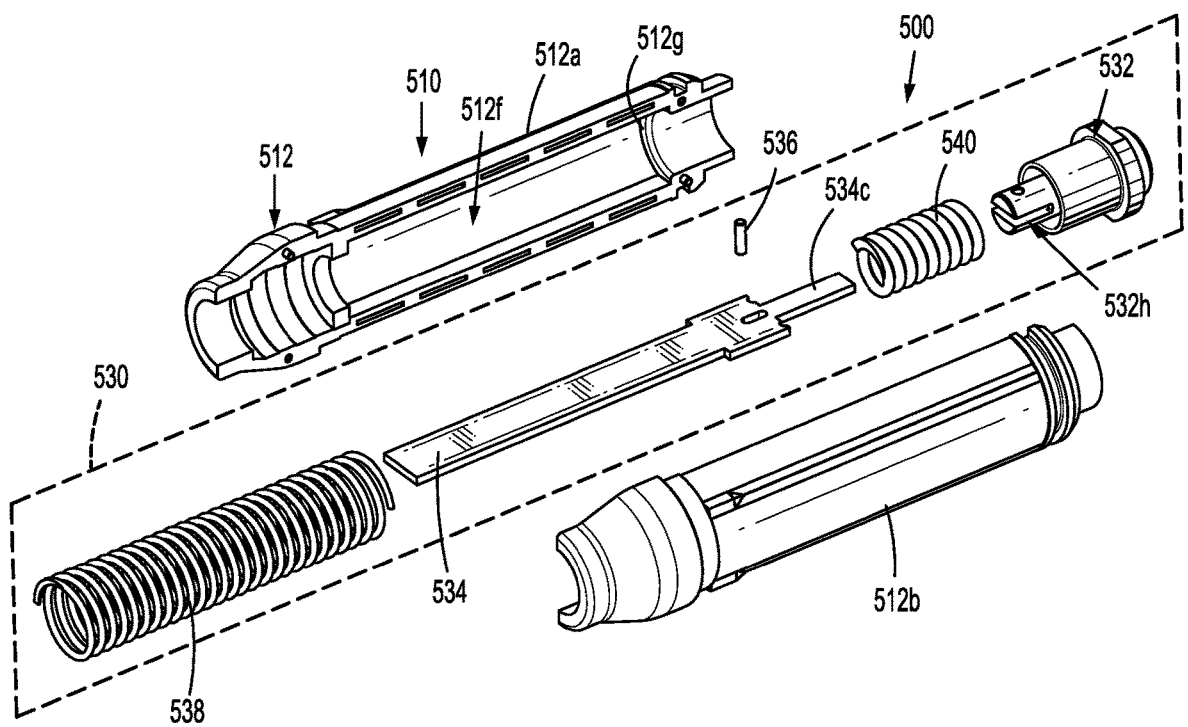
FIG. 43 is a perspective view of the hub assembly of FIG. 42 shown with parts separated.
Figure 44:
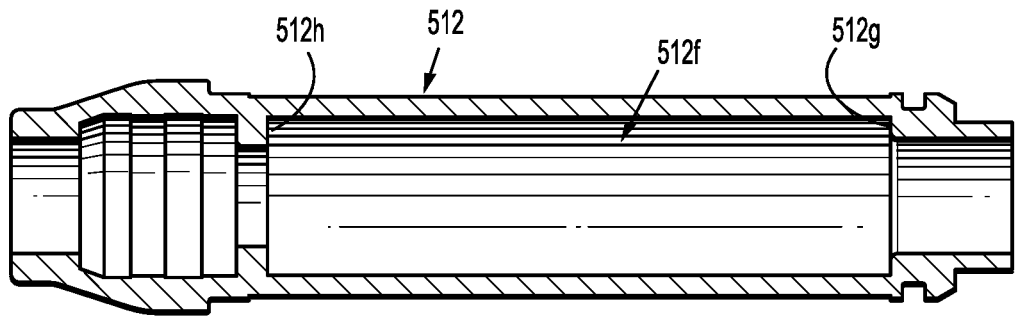
FIG. 44 is a side, longitudinal cross-sectional view of an outer housing of the hub assembly of FIG. 42.

A plunger 534 of the endoscopic assembly 500 is slidably supported within the outer housing 512 and is configured to be selectively connectable to an inner shaft (not shown) of the endoscopic assembly 500 at a distal portion thereof and to the cartridge cylinder 532 at a proximal portion thereof (FIG. 42). As best illustrated in FIG. 43, the plunger 534 defines a generally planar profile, although other suitable profiles are also contemplated, such as circular, oval, or the like. The plunger 534 includes a pair of wings or flanges 534a (FIG. 47) disposed on opposed side surfaces thereof, at a proximal portion thereof, such that the width of the plunger 534 is increased, but not the thickness, although other configurations are also contemplated. In this manner, each of the pair of wings 534a of the plunger 534 is disposed in 180 degree relation to one another. The plunger 534 includes a corresponding pair of reliefs or scallops 534b defined in a proximal portion of the pair of wings 534a and which are configured to receive a portion of the second biasing element 540. A proximal extending stem 534c is disposed on a proximal portion of the plunger 534 and extends in a proximal direction therefrom. The proximal extending stem 534c of the plunger 534 is configured to be slidably received within the counterbore 532g of the cartridge cylinder 532 and, in combination with the counterbore 532g, inhibits the plunger 534 from translating in a radial direction with respect to the cartridge cylinder 532.

Figure 46:
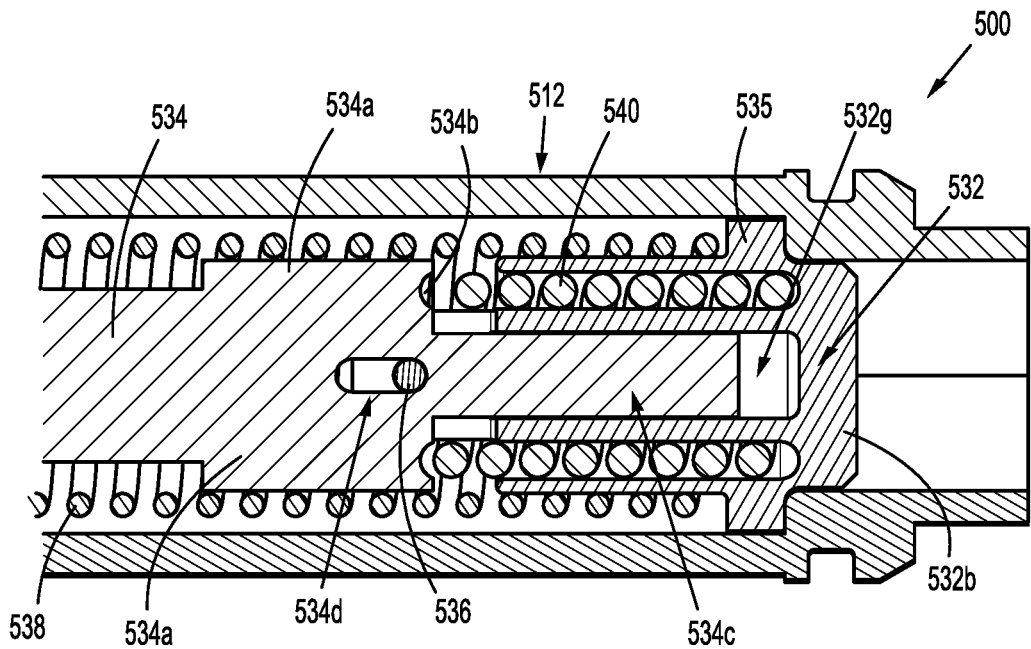
FIG. 46 is a side, longitudinal cross-sectional view of the hub assembly of FIG. 42 shown with the cartridge cylinder in a proximal, retracted position.
Figure 47:
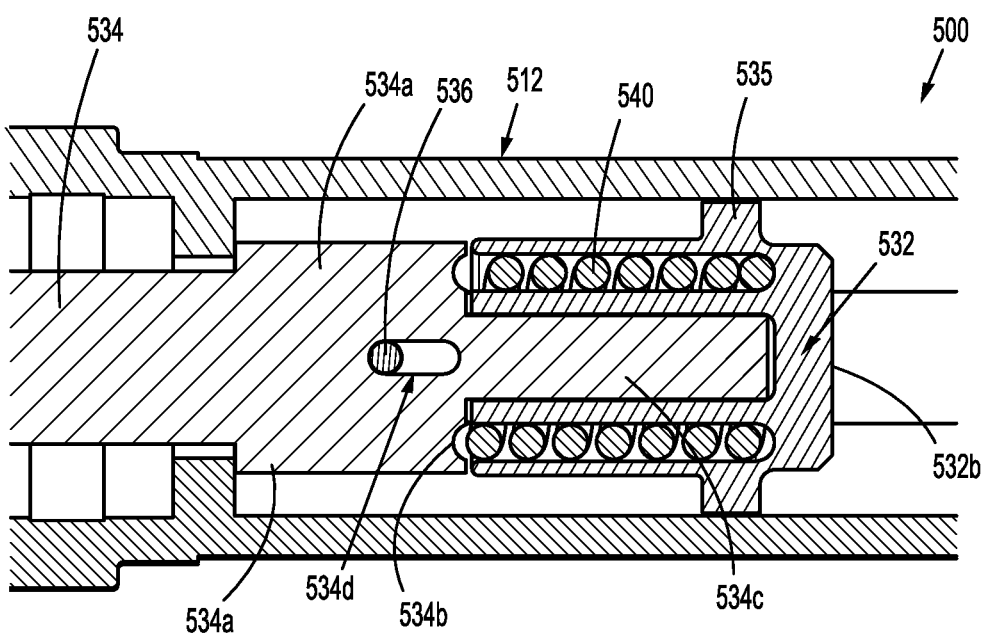
FIG. 47 is a side, longitudinal cross-sectional view of the hub assembly of FIG. 42 shown with the cartridge cylinder in a distal, actuated position.

A proximal portion of the plunger 534 defines a slot or channel 534d (FIG. 47) at a central portion thereof (e.g., along a centerline defined along the plunger 534). The slot 534 is configured to slidably receive the pin 536, thereby slidably coupling the plunger 534 to the cartridge cylinder 532. As best illustrated in FIGS. 46 and 47, the slot 534d is defined through the plunger 534 at a location such that when the cartridge cylinder 532 is in a distal-most position relative to the plunger 534 (e.g., the proximal extending stem 534c of the plunger 534 is fully received within the counterbore 532g of the cartridge cylinder 532), the pin 536 is in a distal-most position within the slot 534d. In this manner, the pin 536 abuts a distal portion of the slot 534d and acts as a stop to inhibit further distal translation of the cartridge cylinder 532 relative to the plunger 534 (FIG. 47). Conversely, the slot 534d is configured to ensure that the cartridge cylinder 532 is maintained in a position relative to the plunger 534 such that during normal operation, the plunger 534 is permitted to translate and completely form a surgical clip (e.g., a proximal most position relative to the plunger, FIG. 46). As can be appreciated, the geometry and location of the slot 534d may be altered to permit the cartridge cylinder 532 to translate a larger or smaller amount relative to the plunger 534, depending upon the needs of the procedure to be performed.

The drive assembly 530 includes a first biasing element 538 coaxially disposed about the cartridge cylinder 532 at a proximal portion thereof and about the plunger 534 at a distal portion thereof (FIG. 42). Although generally illustrated as being a coil spring, it is contemplated that the first biasing element 538 may be any suitable biasing element capable of being compressed, such as Bellville, leaf, polymeric spring, gas spring, or the like. As best illustrated in FIG. 42, the first biasing element 538 is interposed between the radially extending flange 535 of the cartridge cylinder 532 and the distal facing surface 512g of the outer housing 512. The first biasing element 538 has a first spring constant or threshold "K1" which is relatively less firm or less stiff, as compared to a second spring constant or threshold "K2" of a second biasing element 540.

The drive assembly 530 further includes a second biasing element 540 disposed within the annular space 532f of the cartridge cylinder 432 (FIG. 42) and coaxially about the stem 534c of the plunger 534. Although generally illustrated as being a coil spring, it is contemplated that the second biasing element 540 may be any suitable biasing element capable of being compressed, such as Bellville, leaf, polymeric spring, gas spring, or the like. The second biasing element 540 is configured to be slidably received within the annular space 532f of the cartridge cylinder 532 at a first portion thereof and selectively engage the reliefs 534b of the plunger 534 at a second, opposite portion thereof. In this manner, the second biasing element 540 is interposed between the cartridge cylinder 532 and the plunger 534 and includes a second spring constant of threshold "K2" which is relatively more firm or more stiff, as compared to the first threshold "K1" of the first biasing element.

With reference to FIGS. 42-47, in operation, the first and second spring constants "K1" and "K2" cooperate to act as an over-stroke mechanism thereby inhibiting damage to the pair of jaws (not shown) should the jaws be inhibited from fully closing and thereby preventing a full stroke from being completed. Should the jaws become jammed or otherwise be prevented from closing, the trigger 104 would be inhibited from being further actuated. In this manner, continued actuation of the trigger 104 would impart a force upon the cartridge cylinder 532, and therefore the second biasing element 540, that exceeds the second threshold "K2" causing the cartridge cylinder 532 to compress the second biasing element 540 against the pair of wings 534a of the plunger. Since the plunger 534 is inhibited from distally advancing due to the inability of the jaws to further close, continued actuation of the trigger 104 causes the cartridge cylinder 532 to compress the second biasing element 540 and translate in a distal direction (FIG. 47), thereby ultimately permitting the trigger 104 to return to the fully unactuated position thereof. During normal operation, actuation of the trigger 104 imparts a force upon the cartridge cylinder 532 that is capable of exceeding the first threshold "K1" of the first biasing element 538, but not the second threshold "K2" of the second biasing element 540. In this manner, the first biasing element 538 is compressed, thereby enabling closure of the pair of jaws and firing of a surgical clip, but the second biasing element 538 remains uncompressed, thereby enabling the overstroke mechanism to compensate for any jam that may occur during the firing of a surgical clip and prevent damage to the pair of jaws.

In accordance with the present disclosure, the trigger stroke length for trigger 104 of handle assembly 100 is constant or fixed, while the closure stroke length of the pair of jaws 450 of endoscopic assembly 400 connected to handle assembly 100 is different than, for example, the closure stroke of the pair of jaws 250 of endoscopic assembly 200. For example, endoscopic assembly 400 may require the pair of jaws 450 thereof to travel a relatively greater or smaller distance as compared to the pair of jaws 250 of endoscopic assembly 200 in order to complete a full opening and closing thereof. As such, universal handle assembly 100 may be loaded with, and is capable of firing, either endoscopic assembly 200 or endoscopic assembly 400.

In accordance with the present disclosure, while the trigger stroke length of trigger 104 of handle assembly 100 is constant, the closure stroke length for the pair of jaws 250, 450 of each endoscopic assembly 200, 400 is unique for each respective endoscopic assembly 200, 400. Accordingly, each drive assembly 230, 430 of respective endoscopic assemblies 200, 400 functions to accommodate for the variations in the closure stroke lengths for the pair of jaws 250, 450 of respective endoscopic assemblies 200, 400.

To the extent consistent, handle assembly 100 and/or endoscopic assemblies 200, 400 may include any or all of the features of the handle assembly and/or endoscopic assemblies disclosed and described in International Patent Application No. PCT/CN2015/080845, filed Jun. 5, 2015, entitled "Endoscopic Reposable Surgical Clip Applier," International Patent Application No. PCT/CN2015/091603, filed on Oct. 10, 2015, entitled "Endoscopic Surgical Clip Applier," and/or International Patent Application No. PCT/CN2015/093626, filed on Nov. 3, 2015, entitled "Endoscopic Surgical Clip Applier," the entire content of each of which being incorporated herein by reference.

Surgical instruments such as the clip appliers described herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

Figure 48:
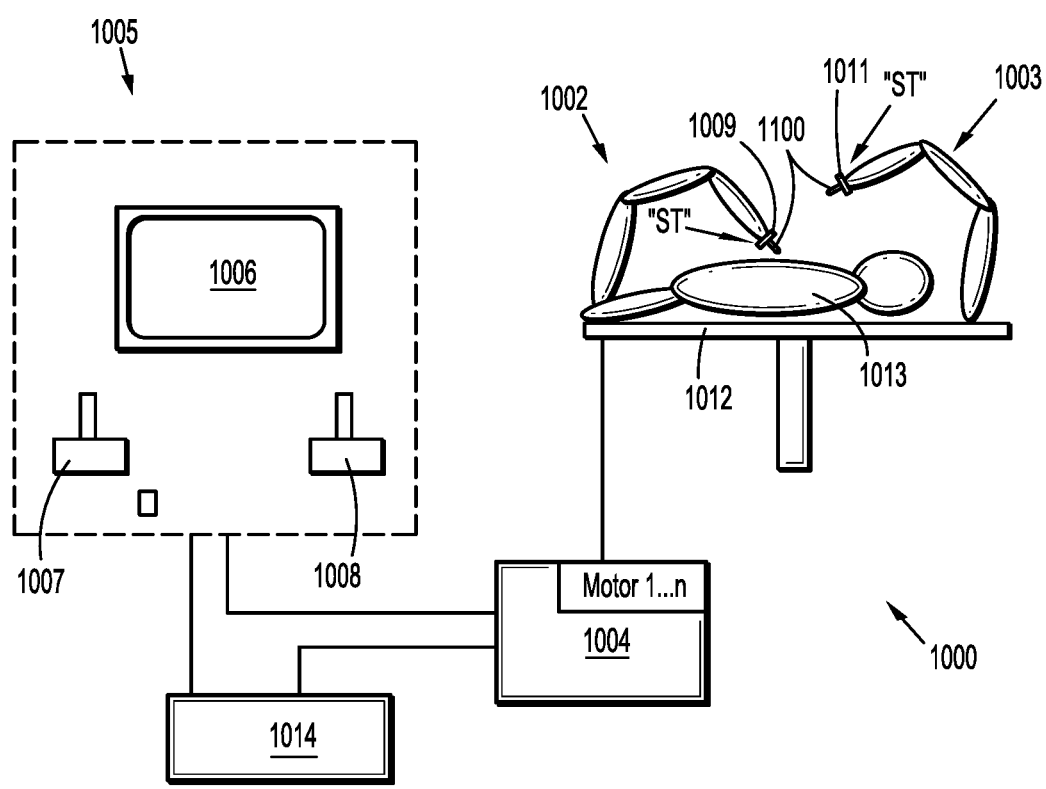
FIG. 48 is a schematic illustration of a robotic surgical system configured for use in accordance with the present disclosure.

Referring to FIG. 48, a medical work station is shown generally as work station 1000 and generally may include a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a person (not shown), for example a surgeon, may be able to telemanipulate robot arms 1002, 1003 in a first operating mode.

Each of the robot arms 1002, 1003 may include a plurality of members, which are connected through joints, and an attaching device 1009, 1011, to which may be attached, for example, a surgical tool "ST" supporting an end effector 1100, in accordance with any one of several embodiments disclosed herein, as will be described in greater detail below.

Robot arms 1002, 1003 may be driven by electric drives (not shown) that are connected to control device 1004. Control device 1004 (e.g., a computer) may be set up to activate the drives, in particular by means of a computer program, in such a way that robot arms 1002, 1003, their attaching devices 1009, 1011 and thus the surgical tool (including end effector 1100) execute a desired movement according to a movement defined by means of manual input devices 1007, 1008. Control device 1004 may also be set up in such a way that it regulates the movement of robot arms 1002, 1003 and/or of the drives.

Medical work station 1000 may be configured for use on a patient 1013 lying on a patient table 1012 to be treated in a minimally invasive manner by means of end effector 1100. Medical work station 1000 may also include more than two robot arms 1002, 1003, the additional robot arms likewise being connected to control device 1004 and being telemanipulatable by means of operating console 1005. A medical instrument or surgical tool (including an end effector 1100) may also be attached to the additional robot arm. Medical work station 1000 may include a database 1014, in particular coupled to with control device 1004, in which are stored, for example, pre-operative data from patient/living being 1013 and/or anatomical atlases.

Reference is made herein to U.S. Pat. No. 8,828,023 content of which is incorporated herein by reference, for a more detailed discussion of the construction and operation of an exemplary robotic surgical system.

It is contemplated, and within the scope of the present disclosure, that other endoscopic assemblies, including a pair of jaws having a unique and diverse closure stroke length thereof, may be provided with a drive assembly, similar to any of the drive assemblies described herein, for accommodating and adapting the closure stroke length for the pair of jaws thereof to the constant trigger stroke length.

Accordingly, various endoscopic assemblies, constructed in accordance with the principles of the present disclosure, may be provided which are also capable of firing or forming or closing surgical clips of various sizes, materials, and configurations, across multiple platforms for multiple different manufactures.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

What is claimed is:

1. A hub assembly for use with an endoscopic assembly of a reposable surgical clip applier, the hub assembly comprising:

an outer housing; and a drive assembly supported within the outer housing, the drive assembly including:
- a cartridge cylinder slidably supported in the outer housing;
- a plunger translatably supported within the outer housing, the plunger slidably coupled to the cartridge cylinder at a proximal end thereof;
- a first biasing element interposed between the cartridge cylinder and the outer housing, the first biasing element having a first threshold; and
- a second biasing element interposed between the cartridge cylinder and the plunger, the second biasing element having a second threshold that is greater than the first threshold,
- wherein when a force applied to the cartridge cylinder exceeds the first threshold, the cartridge cylinder and plunger translate simultaneously within the outer housing, and
- wherein when the force applied to the cartridge cylinder exceeds the second threshold, the cartridge cylinder translates relative to the plunger.

2. The hub assembly of claim 1, wherein the first biasing element is slidably retained within a cavity defined through a distal portion of the cartridge cylinder.

3. The hub assembly of claim 2, wherein the cartridge cylinder further includes a longitudinally extending boss disposed within the cavity.

4. The hub assembly of claim 3, wherein a bore is defined through a distal portion of the longitudinally extending boss.

5. The hub assembly of claim 4, further comprising a pin fixedly retained within the bore of the longitudinally extending boss and slidably retained within a slot defined through a proximal portion of the plunger, wherein the pin is configured to slidably couple the plunger to the cartridge cylinder.

6. The hub assembly of claim 1, wherein the proximal portion of the plunger defines a pair of wings on opposed side surfaces thereof, the pair of wings configured to engage the first biasing element.

7. The hub assembly of claim 1, wherein an inner portion of the outer housing defines an annular groove, the annular groove defining proximal and distal facing surfaces.

8. The hub assembly of claim 7, wherein the proximal facing surface of the annular groove is configured to engage a distal portion of the second biasing element.

9. The hub assembly of claim 8, wherein a radially extending flange is disposed on a proximal portion of the cartridge cylinder, wherein a distal portion of the radially extending flange is configured to engage a proximal portion of the second biasing element.

10. The hub assembly of claim 9, wherein a proximal portion of the radially extending flange is configured to abut the distal facing surface of the annular groove of the outer housing.

11. An endoscopic assembly for use with a reposable surgical clip applier, the endoscopic assembly comprising:
- a shaft assembly having an outer tube and a pair of jaws fixedly supported in, and extending from, a distal end thereof; and
- a hub assembly configured for selective connection to an actuation assembly of the reposable surgical clip applier, the hub assembly including:
- an outer housing; and
- a drive assembly supported within the outer housing, the drive assembly including:
  - a cartridge cylinder slidably supported in the outer housing;
  - a plunger translatably supported within the outer housing, the plunger slidably coupled to the cartridge cylinder at a proximal end thereof;
  - a first biasing element interposed between the cartridge cylinder and the outer housing, the first biasing element having a first threshold; and
  - a second biasing element interposed between the cartridge cylinder and the plunger, the second biasing element having a second threshold that is greater than the first threshold,
  - wherein when a force applied to the cartridge cylinder exceeds the first threshold, the cartridge cylinder and plunger translate simultaneously within the outer housing, and
  - wherein when the force applied to the cartridge cylinder exceeds the second threshold, the cartridge cylinder translates relative to the plunger.

12. The endoscopic assembly of claim 11, wherein the first biasing element is slidably retained within a cavity defined through a distal portion of the cartridge cylinder.

13. The endoscopic assembly of claim 12, wherein the cartridge cylinder further includes a longitudinally extending boss disposed within the cavity.

14. The endoscopic assembly of claim 13, wherein a bore is defined through a distal portion of the longitudinally extending boss.

15. The endoscopic assembly of claim 14, wherein the drive assembly further includes a pin fixedly retained within the bore of the longitudinally extending boss and slidably retained within a slot defined through a proximal portion of the plunger, wherein the pin is configured to slidably couple the plunger to the cartridge cylinder.

16. The endoscopic assembly of claim 11, wherein the proximal portion of the plunger defines a pair of wings on opposed side surfaces thereof, the pair of wings configured to engage the first biasing element.

17. The endoscopic assembly of claim 11, wherein an inner portion of the outer housing defines an annular groove, the annular groove defining proximal and distal facing surfaces.

18. The endoscopic assembly of claim 17, wherein the proximal facing surface of the annular groove is configured to engage a distal portion of the second biasing element.

19. The endoscopic assembly of claim 18, wherein a radially extending flange is disposed on a proximal portion of the cartridge cylinder, wherein a distal portion of the radially extending flange is configured to engage a proximal portion of the second biasing element.

20. The endoscopic assembly of claim 19, wherein a proximal portion of the radially extending flange is configured to abut the distal facing surface of the annular groove of the outer housing.

* * * * *